(12) United States Patent
Jung et al.

(10) Patent No.: US 8,618,311 B2
(45) Date of Patent: Dec. 31, 2013

(54) SYNTHETIC PROCESSES FOR THE PREPARATION OF AMINOCYCLOHEXYL ETHER COMPOUNDS

(75) Inventors: Grace Jung, New Westminster (CA); James Gee Ken Yee, Vancouver (CA); Doug Ta Hung Chou, Vancouver (CA); Bertrand M. C. Plouvier, Vancouver (CA)

(73) Assignee: Cardiome Pharma Corp., Vancouver, BC (CA)

( * ) Notice: Subject to any disclaimer, the term of this patent is extended or adjusted under 35 U.S.C. 154(b) by 0 days.

(21) Appl. No.: 13/612,539

(22) Filed: Sep. 12, 2012

(65) Prior Publication Data

US 2013/0090483 A1 Apr. 11, 2013

Related U.S. Application Data

(62) Division of application No. 13/297,846, filed on Nov. 16, 2011, now Pat. No. 8,344,162, which is a division of application No. 12/709,355, filed on Feb. 19, 2010, now Pat. No. 8,080,673, which is a division of application No. 11/455,280, filed on Jun. 15, 2006, now Pat. No. 7,754,897.

(60) Provisional application No. 60/748,248, filed on Dec. 7, 2005, provisional application No. 60/690,989, filed on Jun. 15, 2005.

(51) Int. Cl.
*C07D 207/40* (2006.01)
*C07D 207/416* (2006.01)

(52) U.S. Cl.
USPC .......................................... 548/544; 548/556

(58) Field of Classification Search
USPC ................................................ 548/544, 556
See application file for complete search history.

(56) References Cited

U.S. PATENT DOCUMENTS

| | | | |
|---|---|---|---|
| 4,282,388 A | 8/1981 | Draber et al. | |
| 4,684,728 A | 8/1987 | Möhring et al. | |
| 5,032,687 A | 7/1991 | Diehl et al. | |
| 5,215,919 A | 6/1993 | Miya et al. | |
| 5,728,873 A | 3/1998 | Kleemiss et al. | |
| 5,846,514 A | 12/1998 | Foster et al. | |
| 6,503,921 B2 | 1/2003 | Naicker et al. | |
| 6,613,739 B1 | 9/2003 | Naicker et al. | |
| 6,617,475 B2 | 9/2003 | Studer et al. | |
| 6,939,878 B2 | 9/2005 | Naicker et al. | |
| 7,053,087 B1 | 5/2006 | Beatch et al. | |
| 7,056,942 B2 | 6/2006 | Hildesheim et al. | |
| 7,057,053 B2 | 6/2006 | Beatch et al. | |
| 7,101,877 B2 | 9/2006 | Bain et al. | |
| 7,259,184 B2 | 8/2007 | Beatch et al. | |
| 7,345,087 B2 | 3/2008 | Beatch et al. | |
| 7,524,879 B2 | 4/2009 | Beatch et al. | |
| 7,534,790 B2 | 5/2009 | Bain et al. | |
| 7,705,036 B2 | 4/2010 | Chou et al. | |
| 7,754,897 B2 | 7/2010 | Jung et al. | |
| 7,786,119 B2 | 8/2010 | Cheu et al. | |
| 7,875,611 B2 | 1/2011 | Bain et al. | |
| 7,977,373 B2 | 7/2011 | Choi et al. | |
| 8,008,342 B2 | 8/2011 | Beatch et al. | |
| 8,022,098 B2 | 9/2011 | Chou et al. | |
| 8,058,304 B2 | 11/2011 | Choi et al. | |
| 2003/0073617 A1 | 4/2003 | Li et al. | |
| 2003/0130170 A1 | 7/2003 | Li et al. | |
| 2003/0186400 A1 | 10/2003 | Asako et al. | |

(Continued)

FOREIGN PATENT DOCUMENTS

CA 710830 A 6/1965
DE 27 53 556 A1 6/1979

(Continued)

OTHER PUBLICATIONS

Adam et al., "Spectral and Chemical Properties of Dimethyldioxirane as Determined by Experiment and ab Initio Calculations," *J. Org. Chem.* 52(13): 2800-2803, 1987.
Alimardanov et al., "Use of DOE for Rapid Development of a Red-Al Reduction Process for the Synthesis of 3,4-Isopropylidenedioxypyrrolidine Hydrotosylate," *Organic Process Research & Development* 8(6): 834-837, 2004.
Anderson et al., "Sulfonation with Inversion by Mitsunobu Reaction: An Improvement on the Original Conditions," *J. Org. Chem.* 61(22): 7955-7958, 1996.
Anderson et al., "The preparation of β-substituted amines from mixtures of epoxide opening products via a common aziridinium ion intermediate," *Tetrahedron*: Asymmetry 10: 2655-2663,1999.

(Continued)

*Primary Examiner* — Joseph Kosack
(74) *Attorney, Agent, or Firm* — Seed IP Law Group PLLC

(57) ABSTRACT

This invention is directed to stereoselective synthesis of compounds of formula (I) or formula (II):

or a pharmaceutically acceptable salt, ester, amide, complex, chelate, clathrate, solvate, polymorph, stereoisomer, metabolite or prodrug thereof; wherein $R^3$, $R^4$ and $R^5$ are defined herein. Compounds of formula (I) and formula (II) are known to be useful in treating arrhythmias.

9 Claims, No Drawings

(56) References Cited

U.S. PATENT DOCUMENTS

| | | |
|---|---|---|
| 2004/0049049 A1 | 3/2004 | Jurayj et al. |
| 2004/0082043 A1 | 4/2004 | Yadav et al. |
| 2006/0094880 A9 | 5/2006 | Barrett et al. |
| 2007/0190156 A1 | 8/2007 | Beatch et al. |
| 2009/0069404 A1 | 3/2009 | Czarnik |
| 2010/0152464 A1* | 6/2010 | Plouvier et al. ............... 548/544 |
| 2010/0273724 A1 | 10/2010 | Cheu et al. |
| 2011/0207730 A1 | 8/2011 | Bain et al. |
| 2012/0271057 A9 | 10/2012 | Jung et al. |
| 2013/0102791 A1 | 4/2013 | Plouvier et al. |
| 2013/0171077 A1 | 7/2013 | Beatch et al. |

FOREIGN PATENT DOCUMENTS

| | | |
|---|---|---|
| EP | 0 014 263 B1 | 8/1980 |
| EP | 0 317 780 B1 | 5/1989 |
| ES | 475575 A1 | 2/1979 |
| WO | WO 96/23894 A1 | 8/1996 |
| WO | WO 97/33552 A1 | 9/1997 |
| WO | WO 99/50225 A1 | 10/1999 |
| WO | WO 00/23023 A1 | 4/2000 |
| WO | WO 01/96335 A1 | 12/2001 |
| WO | WO 03/105756 A2 | 12/2003 |
| WO | WO 2004/014973 A2 | 2/2004 |
| WO | WO 2004/098525 A2 | 11/2004 |
| WO | WO 2004/099137 A1 | 11/2004 |
| WO | WO 2005/016242 A2 | 2/2005 |
| WO | WO 2005/094897 A2 | 10/2005 |
| WO | WO 2005/097087 A2 | 10/2005 |
| WO | WO 2005/113011 A2 | 12/2005 |
| WO | WO 2006/088525 * | 8/2006 |
| WO | WO 2006/088525 A1 | 8/2006 |
| WO | WO 2006/138673 A2 | 12/2006 |

OTHER PUBLICATIONS

Asunskis and Shechter, "Reactions of Conjugated Nitro Olefins with Phosphoranes and with Dimethylsulfoxonium Methylide to Give Ylides and Nitrocyclopropanes, Respectively," *J. Org. Chem.* 33(3): 1164-1168, 1968.

Augy-Dorey et al., "Synthesis of Carbocyclic Analogues of Lipid X," *Tetrahedron* 49(36): 7997-8006, 1993.

Bodenan et al., "Acid-Catalyzed Ring Opening of 2-Substituted Aziridines with Alcohols," *Synthesis*: 288-292, Mar. 1992.

Bogatskii et al., "Effect of Polymethylene- and Polyhydroxyethylene-bis-(2-Amino-1,3-Diazepinium) Iodides on Cell and Model Membranes," *Byulleten' Eksperimental'noi Biologii i Meditsiny* 94(8): 52-54, Aug. 1982 [English translation included from the Department of Chemistry of Macrocyclic Complexones, Physicochemical Institute, Academy of Sciences of the Ukrainian SSSR, Odessa, pp. 1071-1074.].

Brown and Krishnamurthy, "Forty Years of Hydride Reductions," *Tetrahedron* 35(64): 567-607, 1979.

Brown et al., "The Direct and Enantioselective Organocatalytic α-Oxidation of Aldehydes," *J. Am. Chem. Soc.* 125(36): 10808-10809, 2003.

Bryce and Gardiner, "Stereospecific Synthesis of the Cyclopenta[e]phenanthridine Ring System: Tetracyclic and Pentacyclic Analogues of Cephalotaxus Alkaloids," *Tetradedron* 44(2): 599-612, 1988.

Carter et al., "Towards phase-transfer catalysts with a chiral anion: inducing asymmetry in the reactions of cations," *Tetrahedron*: Asymmetry 14: 1995-2004, 2003.

Cassidei et al., "Oxygen-17 and Carbon-13 Identification of the Dimethyldioxirane Intermediate Arising in the Reaction of Potassium Caroate with Acetone," *J. Org. Chem.* 52(4): 699-700, 1987.

Chelucci et al., "Synthesis of 1-Substituted 2-[(2S)-2-Pyrrolidinyl]pyridine from L-Proline," *Synthesis*: 1121-1122, Dec. 1990.

Chiu et al., "Molecular dynamics computations and solid state nuclear magnetic resonance of the gramicidin cation channel," *Biophys. J.* 60: 974-978, Oct. 1991.

Christoffers et al., "Synthesis, resolution, and absolute configuration of *trans*-1-amino-2-dimethylaminocyclohexane," *Tetrahedron* 57: 1765-1769, 2001.

Curci et al., "Selective Oxidation of O-Isopropylidene Derivatives of Diols to 2-Hydroxy Ketones Employing Dioxiranes," *Tetrahedron Letters* 37(1): 115-118, 1996.

Curtis and Walker, "Quantification of arrhythmias using scoring systems: an examination of seven scores in an in vivo model of regional myocardial ischaemia," *Cardiovascular Research* 22: 656-665, 1988.

D'Accolti et al., "Selective Oxidation of Optically Active *sec,sec*-1,2-Diols by Dioxiranes. A Practical Method for the Synthesis of Homochiral α-Hydroxy Ketones in High Optical Purity," *J. Org. Chem.* 58(14): 3600-3601, 1993.

Daverio and Zanda, "Enantioselective reductions by chirally modified alumino- and borohydrides," *Tetradron: Asymmetry* 12: 2225-2259, 2001.

Engman and Cava, "BIS(p-Methoxyphenyl)telluroxide, a Novel Organotellurium Aldol Catalyst," *Tetrahedron Letters* 22(52): 5251-5252, 1981.

Fráter et al., "Regioselective Synthesis of (±)-Gabaculine Hydrochloride," *Tetrahedron Letters* 25(3): 281-284, 1984.

Godchot and Mousseron, "Sur le dédoublement du 2-aminocyclohexanol en ses antipodes optiques," *Bull. Soc. Chim. Fr.* 51: 1277-1282, 1932.

Gonzaléz-Sabín et al., "Chemoenzymatic preparation of optically active β-amino-cyclohexanols and their application in the enantioselective addition of diethylzinc to benzaldehyde," *Tetrahedron*: Asymmetry 15: 1335-1341, 2004.

Greenwald, "PEG drugs: an overview," *Journal of Controlled Release* 74: 159-171, 2001.

Hamon and Tuck, "Asymmetric Synthesis of (S)-1-Methyl-2-cylohexen-1-ol, a Constituent of the Aggregation Pheromone of *Dendroctonus pseudotsugae*," *Tetrahedron* 56: 4829-4835, 2000.

Hayashi et al., "Asymmetric Ring Opening Reactions of Symmetrical N-Acylaziridines with Thiols Catalyzed by Chiral Dialkyl Tartrate—Diethylzinc Complexes," *Tetrahedron* 52(23): 7817-7832, 1996.

Henrot et al., "Aminoacids as Chiral Synthons: Preparation of Enantiomerically Pure (R) and (S) Malic Acids and Its Application to the Synthesis of 3-Hydroxy 4-Butanolide," *Synthetic Communications* 16(2): 183-190, 1986.

Higuchi and Shiobara, "Quantitative Determination of Nifedipine in Human Plasma by Selected Ion Monitoring," *Biomedical Mass Spectrometry* 5(3): 220-223, 1978.

Howard and Walker, "Electrical Stimulation Studies with Quinacainol, a Putative 1C Agent, in the Anaesthetised Rat," *Proc. West. Pharmacol. Soc.* 33: 123-127, 1990.

Iida et al., "Synthesis of $^{13}$C-Labelled Compounds having a Urea Unit, and Observation of $^{13}$C-Isotope Effect in Their Infrared Spectra," *J. Labelled Cpd. Radiopharm.* XXXIX(1): 69-77, 1997.

Jacobsen, "Asymmetric Catalysis of Epoxide Ring-Opening Reactions," *Acc. Chem. Res.* 33(6): 421-431, 2000.

Johansen et al., "Synthesis of carbon-14 and stable isotope labelled NN414: a potent potassium channel opener," *J. Labelled Cpd. Radiopharm.* 47: 127-138, 2004.

Joshi et al., "Enantioselective Ring Cleavage of *meso*-Epoxides with B-Halodiisopinocampheylboranes," *J. Am. Chem. Soc.* 110: 6246-6248, 1988.

Kahl et al., "Radioimmunoassay for the Calcium Release Channel Agonist Ryanodine," *Analytical Biochemistry* 218: 55-62, 1994.

Kepler et al., "Synthesis of 5,5-Diphenylhydantoin-2,4,5-$^{13}$C$_3$," *Journal of Labelled Compounds* 10(4): 683-687, Oct.-Dec. 1974.

Kinugasa et al., "Desymmetrization of *meso*-1,2-Diols via Chiral Lewis Acid-Mediated Ring-Cleavage of 1,3-Dioxolane Derivatives," *J. Am. Chem. Soc.* 119(38): 9067-9068, 1997.

Kodukulla et al., "Synthesis, Chemical Transformation and Antimicrobial Activity of a Novel Class of Nitroolefins: 1,3-Diaryl-2-nitroprop-1-enes," *Synthetic Communications* 24(6): 819-832, 1994.

Kubo et al., "A Facile Synthesis of 1,2,3,4-Tetrahydroisoquinolines Through Cyclization of O-N-Acetals," *Synthesis*: 824-827, Sep. 1987.

(56) References Cited

OTHER PUBLICATIONS

Liu and Yao, "One-pot synthesis of *trans*-β-alkylstyrenes," *Tetrahedron Letters 42*: 6147-6150, 2001.

Luurtsema et al., "Synthesis and PET-Studies of (R)- and (S)-[$^{11}$C]Verapamil for Measuring PGP Function in MDR1A(+/+)/B(+/+) and MDR1A(-/-)/B(-/-) Mice," *J. Labelled Cpd. Radiopharm. 44*(Suppl. I): S313-S315, 2001.

Maestro et al., "Enzymatic resolution of (±)-trans-2-aminocyclohexanol and (±)-*trans*-2-aminocyclopentanol," *Tetrahedron: Asymmetry 8*(18): 3153-3159, 1997.

Martichonok and Whitesides, "Stereoselective α-Sialylation with Sialyl Xanthate and Phenylsulfenyl Triflate as a Promotor," *J. Org. Chem. 61*(5): 1702-1706, 1996.

Martinelli et al., "Selective monosulfonylation of internal 1,2-diols catalyzed by di-*n*-butyltin oxide," *Tetrahedron Letters 41*: 3773-3776, 2000.

Martínez et al., "Highly Enantioselective Ring Opening of Epoxides Catalyzed by (salen)Cr(III) Complexes," *J. Am. Chem. Soc. 117*(21): 5897-5898, 1995.

Matsumoto et al., "Diastereoselective Synthesis of a Key Intermediate for the Preparation of Tricyclic β-Lactam Antibiotics," *Tetrahedron Letters 40*: 5043-5046, 1999.

Matsunaga et al., "Catalytic Enantioselective *meso*-Epoxide Ring Opening Reaction with Phenolic Oxygen Nucleophile Promoted by Gallium Heterobimetallic Multifunctional Complexes," *J. Am. Chem. Soc. 122*(10): 2252-2260, 2000.

McCleland et al., "Mechanistic Studies of the Zirconium—Triisopropanolamine-Catalyzed Enantioselective Addition of Azide to Cyclohexene Oxide," *J. Org. Chem. 63*(19): 6656-6666, 1998.

McGraw-Hill, Notes for Chapter 15: Alcohols, Biols and Thiols, obtained from the WayBackMachine with an archive date of Oct. 30, 2002, 4 pages.

Mello et al., "Enzymic Regioselectivity in the Hydroxylation of Cholesterol Catalyzed by a Membrane-Spanning Metalloporphyrin," *J. Org. Chem. 53*(16): 3891-3893, 1988.

Mello et al., "Oxidations by Methyl(trifluoromethyl)dioxirane. 2. Oxyfunctionalization of Saturated Hydrocarbons," *J. Am. Chem. Soc. 111*(17): 6749-6757, 1989.

Momiyama and Yamamoto, "Catalytic Enantioselective Synthesis of α-Aminooxy and α-Hydroxy Ketone Using Nitrosobenzene," *J. Am. Chem. Soc. 125*(20): 6038-6039, 2003.

Mottet et al., "A Simple and Efficient Preparation of Propargylic β-Keto Esters through Transesterification," *J. Org. Chem. 64*(4): 1380-1382, 1999.

Moustafa et al., "Comparative Study on the para-Metabolic Oxidation of Phenytoin and Decadeuteriophenytoin," *Arzneim.-Forsch/Drug Res. 40*(II, 10): 1076-1078, 1990.

Mowry and Butler, "Fumaronitrile," *Organic Syntheses, Coll. 4*: 486, 1963, 3 pages.

Murray and Jeyaraman, "Dioxiranes: Synthesis and Reactions of Methyldioxiranes," *J. Org. Chem. 50*(16) 2847-2853, 1985.

Nachtsheim and Kaiser, "Die asymmetrische Synthese von cis-1R,2R- und cis-1S,2S-2-Arylcyclohexanaminen," *Arch. Pharm. (Weinheim) 322*(4): 187-197, Apr. 1989.

Nagai, "Optical Rotatory Dispersion of Nitrobenzene Derivatives. VII. Application of Modified Curtius Rearrangement for Determining the Free Carboxylic Position in Some Partial Esters of 3-Nitrophthalic and 4-Nitrohemimellitic Acid," *Chem. Pharm. Bull. 23*(8): 1841-1844, 1975.

Nagel and Nedden, "Preparative and Structural Chemistry of Chiral 3-(Diphenylphosphanyl)-pyrrolidines and Their Palladium(II) Complexes," *Chem. Ber./Recueil 130*: 385-397, 1997.

Nakamura et al., "Recent developments in asymmetric reduction of ketones with biocatalysts," *Tetrahedron: Asymmetry 14*(60): 2659-2681, 2003.

Nakamura et al., "Chemistry and biology of khafrefungin. Large-scale synthesis, design, and structure-activity relationship of khafrefungin, an antifungal agent," *Org. Biomol. Chem. 1*: 3362-3376, 2003.

Nakane et al., "7-Oxabicyclo[2.2.1]heptyl Carboxylic Acids as Thromboxane A$_2$ Antagonists: Aza ω-Chain Analogues," *J. Med. Chem. 33*(9) 2465-2476, 1990.

Naylor et al., "4-[(Alkylylamino)methyl]furo[3,2-*c*]pyridines: A New Series of Selective κ-Receptor Agonists," *Journal of Medicinal Chemistry 37*(14): 2138-2144, 1994.

Ohkuma et al., "Stereoselective Hydogenation of Simple Ketones Catalyzed by Ruthenium(II) Complexes," *Journal of Organic Chemistry 61*(15): 4872-4873, 1996.

Ohtaka and Kajiwara, "Synthesis of [$^{13}$C$_2$]nifedipine," *J. Labelled Cpd. Radiopharm. 46*: 1177-1179, 2003.

Pallavicini et al., "Resolution of 5-hydroxymethyl-2-oxazolidinone by preferential crystallization and investigations on the nature of the racemates of some 2-oxazolidinone derivatives," *Tetrahedron: Asymmetry 15*: 1659-1665, 2004.

Paquette et al., "Systematic Analysis of the Intramolecular Competition Associated with the Ring Closing Metathesis of Ene-Diene Systems of Differing Chain Length with a Pair of Ruthenium Catalysts," *Helvetica Chimica Acta 85*: 3033-3051, 2002.

Pasumansky and Singaram, "Recent Advances in the Chemistry of Lithium Aminoborohydrides," *Aldrichimica Acta 38*(2): 61-65, 2005.

Paterson et al., "Total Synthesis of the Microtubule-Stabilizing Agent (—)-Laulimalide," *Organic Letters 3*(20): 3149-3152, 2001.

Raiford and Fox, "Condensation of Vanillin Substitution Products with Nitromethane," *J. Org. Chem. 9*: 170-174, 1944.

Rampe et al., "Deuterated analogs of verapamil and nifedipine. Synthesis and biological activity," *Eur. J. Med. Chem. 28*: 259-263, 1993.

Rao et al., "Cycloaddition of citral dienamines to β-nitrostyrenes: A stereochemical consideration," *Indian Journal of Chemistry 29B*: 207-214, Mar. 1990.

Schaus et al., "Practical Synthesis of Enantiopure Cyclic 1,2-Amino Alcohols via Catalytic Asymmetric Ring Opening of Meso Epoxides," *J. Org. Chem. 62*(12): 4197-4199, 1997.

Schlichter and Frahm, "Asymmetric Reductive Amination of Cycloalkanones, XIII: Enantioselective Amidoamination: A New Regiospecific Strategy for the Synthesis of Chiral Cyclohexane-1,2-diamino-Derivatives," *Arch. Pharm. (Weinheim) 326*: 429-436, 1993.

Srebnik et al., "Chiral Synthesis via Organoboranes 23. Enantioselective Ring Opening of *meso*-Epoxides with *B*-Halodiisopinocampheylboranes. The First General Synthesis of Optically Active 1,2-Halohydrins," *Israel Journal of Chemistry 29*: 229-237, 1989.

Tasker et al., "Potent and Selective Non-Benzodioxole-Containing Endothelin-A Receptor Antagonists," *J. Med. Chem 40*(3): 322-330, 1997.

Toshima and Tatsuta, "Recent Progress in *O*-Glycosylation Methods and Its Application to Natural Products Synthesis," *Chem. Rev. 93*(4): 1503-1531, 1993.

Tsuda et al., "A stereocontrolled construction of 2-azido-2-deoxy-1,2-*trans*-β-glycosidic linkages utilizing 2-azido-2-deoxyglycopyranosyl diphenyl phosphates," *Tetrahedron Letters 44*: 6453-6457, 2003.

Tuck et al., "A Simple Procedure for the Deuteriation of Phenols," *J. Labelled Cpd. Radiopharm. 43*: 817-823, 2000.

Urban et al., "Process Research and Large-Scale Synthesis of a Novel 5,6-Dihydro-(9H)-pyrazolo[3,4-*c*]-1,2,4-triazolo[4,3-*a*]pyridine PDE-IV Inhibitor," *Organic Process Research & Development 5*(6): 575-580, 2001.

Ursini et al., "Enzymatic Method of Preparation of Optically Active *trans*-2-Amino Cyclohexanol Derivatives," *Synthetic Communications 29*(8): 1369-1377, 1999.

Varma et al., "Microwave-Assisted Henry Reaction: Solventless Synthesis of Conjugated Nitroalkenes," *Tetrahedron Letters 38*(29): 5131-5134, 1997.

Ward, "Chiral Separations," *Anal. Chem. 74*(12): 2863-2872, Jun. 15, 2002.

Wimalasena and May, "Mechanistic Studies on Dopamine β-Monooxygenase Catalysis: N-Dealkylation and Mechanism-Based Inhibition by Benzylic-Nitrogen-Containing Compounds. Evidence for a Single-Electron-Transfer Mechanism," *J. Am. Chem. Soc. 109*(13): 4036-4046, 1987.

Yadav et al., "Efficient Enantioselective Reduction of Ketones with *Daucus carota* Root," *J. Org. Chem. 67*(11): 3900-3903, 2002.

\* cited by examiner

SYNTHETIC PROCESSES FOR THE PREPARATION OF AMINOCYCLOHEXYL ETHER COMPOUNDS

CROSS-REFERENCE TO RELATED APPLICATIONS

This application is a divisional of U.S. patent application Ser. No. 13/297,846, filed Nov. 16, 2011 (now allowed); which is a divisional of U.S. patent application Ser. No. 12/709,355, filed Feb. 19, 2010 (now U.S. Pat. No. 8,080,673); which is a divisional of U.S. patent application Ser. No. 11/455,280, filed Jun. 15, 2006 (now U.S. Pat. No. 7,754,897); which claims the benefit under 35 U.S.C. §119(e) of U.S. Provisional Patent Application No. 60/748,248, filed Dec. 7, 2005, and U.S. Provisional Patent Application No. 60/690,989, filed Jun. 15, 2005. These applications are incorporated herein by reference in their entireties.

FIELD OF INVENTION

The present invention is generally directed toward a method for the stereoselective preparation of aminocyclohexyl ether compounds such as trans-(1R,2R)-aminocyclohexyl ether compounds and/or trans-(1S,2S)-aminocyclohexyl ether compounds as well as various intermediates, substrates and stereoisomers involved. In addition, the present invention is directed toward a method for the stereoselective preparation of aminocyclohexyl ether compounds such as cis-(1R,2S)-aminocyclohexyl ether compounds and/or cis-(1S,2R)-aminocyclohexyl ether compounds The compounds prepared by methods of the present invention are useful for treating medical conditions or disorders, including for example, cardiac arrhythmia, such as atrial arrhythmia and ventricular arrhythmia.

BACKGROUND OF THE INVENTION

Arrhythmia is a variation from the normal rhythm of the heart beat and generally represents the end product of abnormal ion-channel structure, number or function. Both atrial arrhythmias and ventricular arrhythmias are known. The major cause of fatalities resulting from cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these individuals will be first heart attacks and 450,000 of these will be recurrent attacks. About one-third of the people experiencing these attacks will die as a result. At least 250,000 individuals a year die of coronary heart disease within 1 hour of the onset of symptoms and before they reach adequate medical aid. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., N. Engl. J. Med. 327(14):1031 Oct. 1, 1992, discussion 1031-2; Kannel and Wolf, Am. Heart J. 123(1):264-7 Jan. 1992). Its prevalence is likely to increase as the population ages and it is estimated that 3-5% of patients over the age of 60 years have AF (Kannel W. B., Abbot R. D., Savage D. D., McNamara P. M., N. Engl. J. Med. 306(17): 1018-22, 1982; Wolf P. A., Abbot R. D., Kannel W. B. Stroke. 22(8):983-8, 1991). While AF is rarely fatal, it can impair cardiac function and is a major cause of stroke (Hinton R. C., Kistler J. P., Fallon J. T., Friedlich A. L., Fisher C. M., American Journal of Cardiology 40(4):509-13, 1977; Wolf P. A., Abbot R. D., Kannel W. B., Archives of Internal Medicine 147(9):1561-4, 1987; Wolf P. A., Abbot R. D., Kannel W. B. Stroke. 22(8):983-8, 1991; Cabin H. S., Clubb K. S., Hall C., Perlmutter R. A., Feinstein A. R., American Journal of Cardiology 65(16):1112-6, 1990).

PCT Published Patent Applications WO 99/50225 and WO 2004/099137 and U.S. Pat. No. 7,057,053 disclose aminocyclohexylether compounds as being useful in the treatment of arrhythmias. Some of the compounds disclosed therein have been found to be particularly effective in the treatment and/or prevention of AF. However, the synthetic methods described in these patent applications and patent and elsewhere were non-stereoselective and led to mixture of stereoisomers. As active pharmaceutical compounds, it is often desirable that drug molecules are in stereoisomerically substantially pure form. It may not be feasible or cost effective if the correct stereoisomer has to be isolated from a mixture of stereoisomers after a multi-step synthesis. Therefore, there remains a need in the art to develop method for the preparation of stereoisomerically substantially pure trans-aminocyclohexyl ether compounds.

SUMMARY OF THE INVENTION

The present invention is directed to stereoselective syntheses of certain aminocyclohexyl ether compounds and novel intermediates prepared therein. The present invention is also directed to specific aminocyclohexylether compounds.

Accordingly, in one aspect, this invention is directed to a method of making compounds of formula (I):

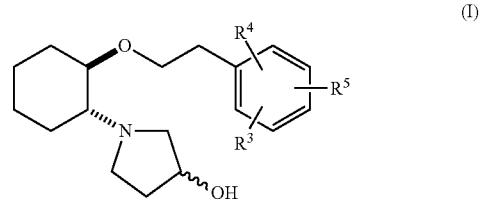

(I)

or a pharmaceutically acceptable salt, ester, amide, complex, chelate, clathrate, solvate, polymorph, stereoisomer, metabolite or prodrug thereof; as a single stereoisomer or as a mixture thereof;

wherein:

$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$ (preferably $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time); and $R^6$, $R^7$, $R^8$, and $R^9$ are each independently selected from hydrogen, acetyl, methanesulfonyl or $C_1$-$C_6$alkyl;

which method comprises:

a) reacting a compound of formula (4):

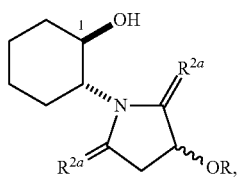

(4)

wherein each $R^{2a}$ is O or $H_2$ where at least one $R^{2a}$ in the compound of formula (4) is O, and R is H, $C_2$-$C_5$acyl or an oxygen-protecting group, with a compound of formula (5):

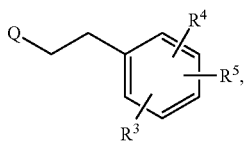

(5)

wherein $R^3$, $R^4$ and $R^5$ are as defined above and Q is a leaving group, to form a compound of formula (6):

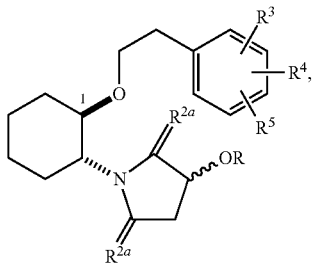

(6)

wherein each $R^{2a}$ is O or $H_2$ where at least one $R^{2a}$ is O, R is H, $C_2$-$C_5$acyl or an oxygen-protecting group and $R^3$, $R^4$ and $R^5$ are as defined above, under suitable conditions such that upon reaction of the compound of formula (4) with the compound of formula (5), the trans relative configuration of the hydroxyl group on the carbon at the 1-position of the compound of formula (4) is retained in the carbon at the 1-position of the compound of formula (6);

b) reducing the compound of formula (6) under suitable conditions to form a compound of formula (I).

This method can further comprise a deprotection step prior to the reaction of a compound of formula (4) with a compound of formula (5), wherein the deprotection step comprises treating a compound of formula (3):

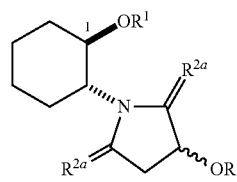

(3)

wherein each $R^{2a}$ is O or $H_2$ where at least one $R^{2a}$ is O, $R^1$ is an oxygen-protecting group (preferably an optionally substituted benzyl group) and R is H, $C_2$-$C_5$acyl or an oxygen-protecting group (preferably $C_2$-$C_5$acyl), to suitable deprotecting conditions to form a compound of formula (4) as set forth above.

This method can further comprise a cyclization step to form a compound of formula (3), wherein the cyclization step comprises reacting a compound of formula (7) or a compound of formula (8) or a mixture of a compound of formula (7) and a compound of formula (8):

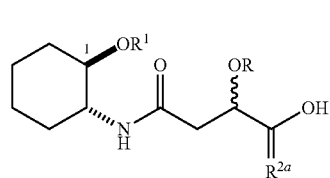

(7)

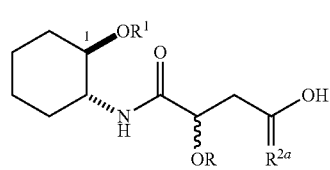

(8)

wherein each $R^1$ is independently an oxygen-protecting group (preferably an optionally substituted benzyl group), each $R^{2a}$ is O or $H_2$, and R is H, $C_2$-$C_5$acyl or an oxygen-protecting group (preferably $C_2$-$C_5$acyl), under suitable conditions to form a compound of formula (3) as set forth above.

This method can further comprise a condensation step to form a compound of formula (7) or a compound of formula (8) or a mixture of a compound of formula (7) and a compound of formula (8), wherein the condensation step comprises reacting a compound of formula (1):

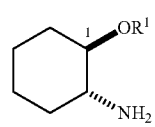

(1)

where $R^1$ is an oxygen-protecting group (preferably an optionally substituted benzyl group), with a compound of formula (2a):

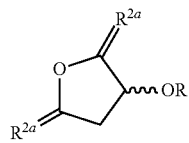

(2a)

wherein each $R^{2a}$ is O or $H_2$ where at least one $R^{2a}$ in the compound of formula (2a) is O, R is H, $C_2$-$C_5$acyl or an oxygen-protecting group (preferably $C_2$-$C_5$acyl), under suitable conditions to form the compound of formula (7) or the compound of formula (8) or the mixture of a compound of formula (7) and a compound of formula (8) as set forth above.

In another aspect, this invention is directed to a method of making compounds of formula (I):

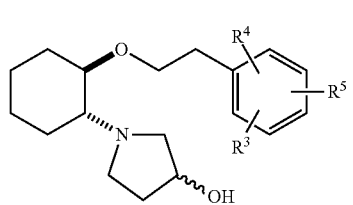

(I)

or a pharmaceutically acceptable salt, ester, amide, complex, chelate, clathrate, solvate, polymorph, stereoisomer, metabolite or prodrug thereof; as a single stereoisomer or as a mixture thereof;
wherein:
$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$ (preferably $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time); and
$R^6$, $R^7$, $R^8$, and $R^9$ are each independently selected from hydrogen, acetyl, methanesulfonyl or $C_1$-$C_6$alkyl;
which method comprises the following:
a) reacting a compound of formula (Ia):

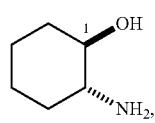

(1a)

with a compound of formula (2a):

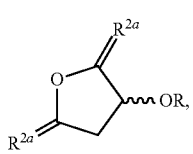

(2a)

under suitable condensation conditions to form a product;
b) reacting the product of a) with a compound of formula (5):

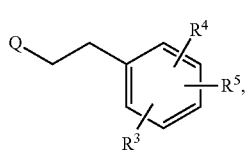

(5)

wherein Q is a leaving group and $R^3$, $R^4$ and $R^5$ are as defined above, under suitable ether coupling conditions to form a product;
c) reacting the product of b) under suitable cyclization conditions to form a compound of formula (6):

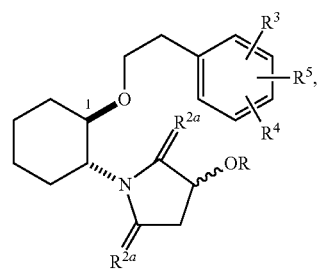

(6)

wherein each $R^{2a}$ is O or $H_2$ where at least one $R^{2a}$ is O, R is H, $C_2$-$C_5$acyl or an oxygen-protecting group (preferably $C_2$-$C_5$acyl) and $R^3$, $R^4$ and $R^5$ are as defined above; and d) reducing the compound of formula (6) under suitable conditions to form a compound of formula (I), as set forth above.

The product of step a) above can comprise a compound of formula (9), a compound of formula (10) or a mixture of a compound of formula (9) and a compound of formula (10):

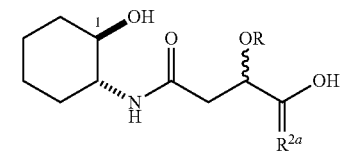

(9)

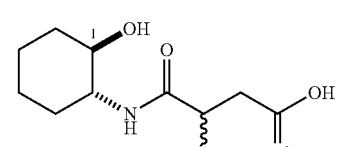

(10)

where each $R^{2a}$ is O or $H_2$ and R is H, $C_2$-$C_5$acyl or an oxygen-protecting group (preferably $C_2$-$C_5$acyl).

The product of step b) above can comprise a compound of formula (11), a compound of formula (12) or a mixture of a compound of formula (11) and a compound of formula (12):

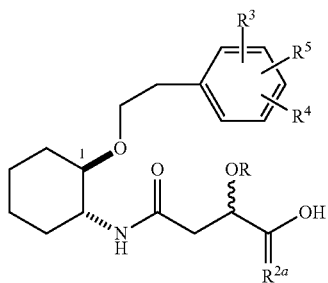

(11)

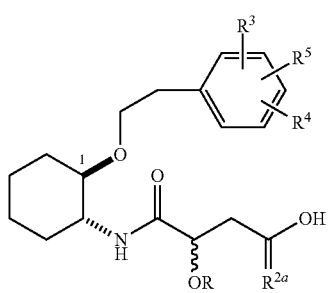

(12)

where each $R^{2a}$ is O or $H_2$, R is H, $C_2$-$C_5$acyl or an oxygen-protecting group (preferably $C_2$-$C_5$acyl) and $R^3$, $R^4$ and $R^5$ are as defined above.

In another aspect, this invention is directed to a method of making compounds of formula (I):

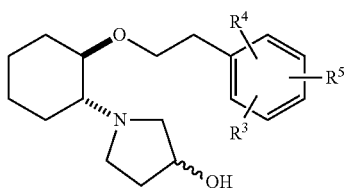

(I)

or a pharmaceutically acceptable salt, ester, amide, complex, chelate, clathrate, solvate, polymorph, stereoisomer, metabolite or prodrug thereof, as a single stereoisomer or as a mixture thereof;

wherein:

$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$ (preferably $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time); and $R^6$, $R^7$, $R^8$, and $R^9$ are each independently selected from hydrogen, acetyl, methanesulfonyl or $C_1$-$C_6$alkyl;

which method comprises:

a) reacting a compound of formula (17):

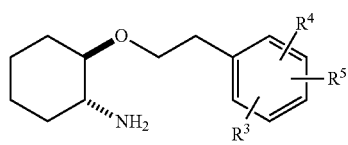

(17)

wherein $R^3$, $R^4$ and $R^5$ are as defined above, with a compound of formula (2a2):

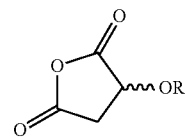

(2a2)

wherein R is H, $C_2$-$C_5$acyl or an oxygen-protecting group (preferably $C_2$-$C_5$acyl), under suitable condensation conditions to form a compound of formula (6b):

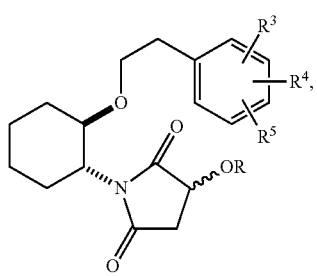

(6b)

wherein R is H, $C_2$-$C_5$acyl or an oxygen-protecting group (preferably an optionally substituted benzyl group) and $R^3$, $R^4$ and $R^5$ are as defined above; and b) reducing the compound of formula (6b) under suitable conditions to form a compound of formula (I), as set forth above.

This method can further comprise a nucleophilic displacement step to form the compound of formula (17), wherein the nucleophilic displacement step comprises treating a compound of formula (16):

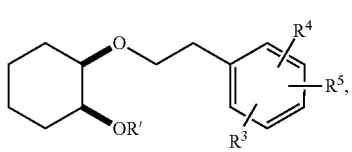

(16)

wherein —OR' is an activated leaving group (preferably optionally substituted alkysulfonate or optionally substituted arylsulfonate) and $R^3$, $R^4$ and $R^5$ are as defined above, with an azide under suitable nucleophilic displacement and subsequent reduction conditions to form a compound of formula (17) as set forth above.

This method con further comprise a preparation step to form the compound of formula (16), wherein the preparation step comprises reacting a compound of formula (15):

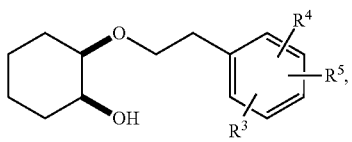
(15)

wherein $R^3$, $R^4$ and $R^5$ are as described above, with an activating agent (preferably an optionally substituted alkylsulfonyl halide or an optionally substituted arylsulfonyl halide) under suitable conditions to form the compound of formula (16) as set forth above.

This method can further comprise an asymmetric reduction step to form a compound (15), wherein the asymmetric reduction step comprises treating a compound of formula (14):

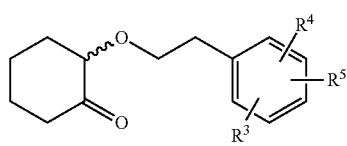
(14)

wherein $R^3$, $R^4$ and $R^5$ are as defined above, under asymmetric reduction/hydrogenation conditions to form the compound of formula (15) as set forth above.

This method can further comprise an etherification step to form a compound of formula (14), wherein the etherification step comprises treating a compound of formula (13):

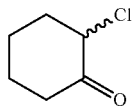
(13)

with a compound of formula (5b):

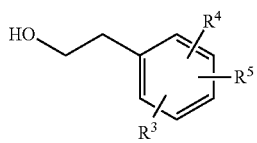
(5b)

wherein $R^3$, $R^4$ and $R^5$ are as defined above, under suitable conditions to form the compound of formula (14), as set forth above.

In another aspect, this invention is directed to a method of making compounds of formula (II):

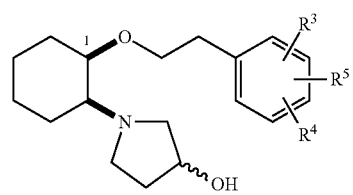
(II)

or a pharmaceutically acceptable salt, ester, amide, complex, chelate, clathrate, solvate, polymorph, stereoisomer, metabolite or prodrug thereof; as a single stereoisomer or as a mixture thereof;

wherein:
$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$ (preferably $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time); and $R^6$, $R^7$, $R^8$, and $R^9$ are each independently selected from hydrogen, acetyl, methanesulfonyl or $C_1$-$C_6$alkyl;

which method comprises:
a) reacting a compound of formula (20):

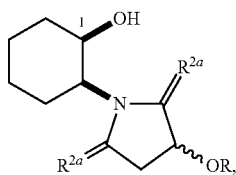
(20)

wherein each $R^{2a}$ is O or $H_2$ where at least one $R^{2a}$ in the compound of formula (20) is O, and R is H, $C_2$-$C_5$acyl or an oxygen-protecting group (preferably $C_2$-$C_5$acyl), with a compound of formula (5):

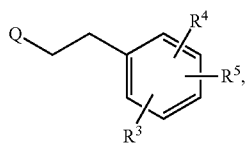
(5)

wherein $R^3$, $R^4$ and $R^5$ are as defined above and Q is a leaving group, to form a compound of formula (21):

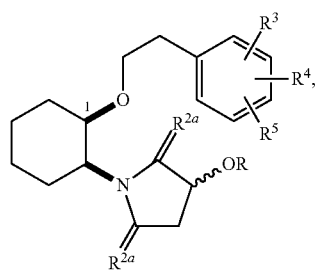
(21)

wherein each $R^{2a}$ is O or $H_2$ where at least one $R^{2a}$ is O, R is H, $C_2$-$C_5$acyl or an oxygen-protecting group and $R^3$, $R^4$ and $R^5$ are as defined above, under suitable conditions such that upon reaction of the compound of formula (20) with the compound of formula (5), the cis relative configuration of the hydroxyl group on the carbon at the 1-position of the compound of formula (20) is retained in the carbon at the 1-position of the compound of formula (21);

b) reducing the compound of formula (21) under suitable conditions to form a compound of formula (II).

This method can further comprise a deprotection step prior to the reaction of a compound of formula (20) with a compound of formula (5), wherein the deprotection step comprises treating a compound of formula (19):

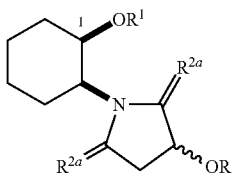
(19)

wherein each $R^{2a}$ is O or $H_2$ where at least one $R^{2a}$ is O, $R^1$ is an oxygen-protecting group (preferably an optionally substituted benzyl group) and R is H, $C_2$-$C_5$acyl or an oxygen-protecting group (preferably $C_2$-$C_5$acyl), to suitable deprotecting conditions to form a compound of formula (20) as set forth above.

This method can further comprise a cyclization step to form a compound of formula (19), wherein the cyclization step comprises reacting a compound of formula (23) or a compound of formula (24) or a mixture of a compound of formula (23) and a compound of formula (24):

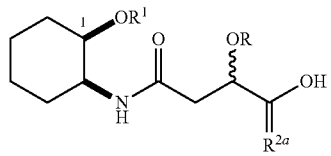
(23)

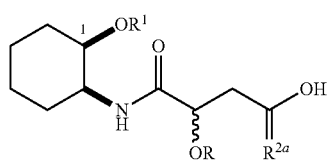
(24)

wherein each $R^1$ is independently an oxygen-protecting group (preferably an optionally substituted benzyl group), each $R^{2a}$ is O or $H_2$, and R is H, $C_2$-$C_5$acyl or an oxygen-protecting group (preferably $C_2$-$C_5$acyl), under suitable conditions to form a compound of formula (19) as set forth above.

This method can further comprise a condensation step to form a compound of formula (23) or a compound of formula (24) or a mixture of a compound of formula (23) and a compound of formula (24), wherein the condensation step comprises reacting a compound of formula (18):

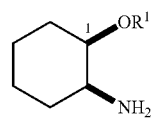
(18)

where $R^1$ is an oxygen-protecting group (preferably an optionally substituted benzyl group), with a compound of formula (2a):

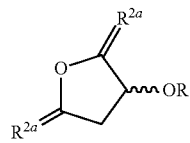
(2a)

wherein each $R^{2a}$ is O or $H_2$ where at least one $R^{2a}$ is O, R is H, $C_2$-$C_5$acyl or an oxygen-protecting group (preferably $C_2$-$C_5$acyl), under suitable conditions to form the compound of formula (23) or the compound of formula (24) or the mixture of a compound of formula (23) and a compound of formula (24) as set forth above.

In another aspect, this invention is directed to a method of making compounds of formula (II):

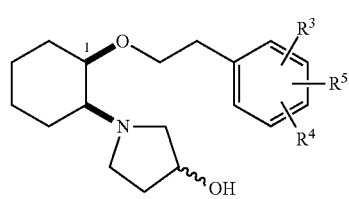
(II)

or a pharmaceutically acceptable salt, ester, amide, complex, chelate, clathrate, solvate, polymorph, stereoisomer, metabolite or prodrug thereof; as a single stereoisomer or as a mixture thereof;
wherein:
$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$ (preferably $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time); and
$R^6$, $R^7$, $R^8$, and $R^9$ are each independently selected from hydrogen, acetyl, methanesulfonyl or $C_1$-$C_6$alkyl;
which method comprises the following:
a) reacting a compound of formula (22):

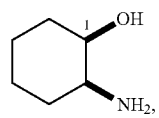
(22)

with a compound of formula (2a):

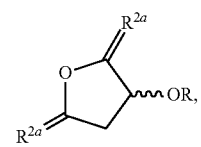
(2a)

under suitable condensation conditions to form a product;
b) reacting the product of a) with a compound of formula (5):

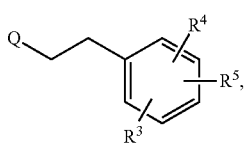

(5)

wherein Q is a leaving group and $R^3$, $R^4$ and $R^5$ are as defined above, under suitable ether coupling conditions to form a product;

c) reacting the product of b) under suitable cyclization conditions to form a compound of formula (21):

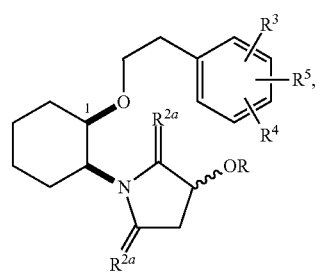

(21)

wherein each $R^{2a}$ is O or $H_2$, R is H, $C_2$-$C_5$acyl or an oxygen-protecting group (preferably $C_2$-$C_5$acyl) and $R^3$, $R^4$ and $R^5$ are as defined above; and d) reducing the compound of formula (21) under suitable conditions to form a compound of formula (II), as set forth above.

The product of step a) above can comprise a compound of formula (25), a compound of formula (26) or a mixture of a compound of formula (25) and a compound of formula (26):

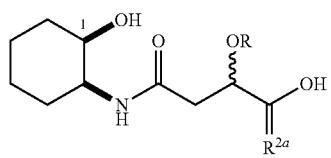

(25)

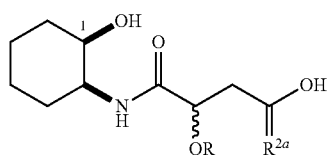

(26)

where each $R^{2a}$ is O or $H_2$ and R is H, $C_2$-$C_5$acyl or an oxygen-protecting group.

The product of step b) above can comprise a compound of formula (27), a compound of formula (28) or a mixture of a compound of formula (27) and a compound of formula (28):

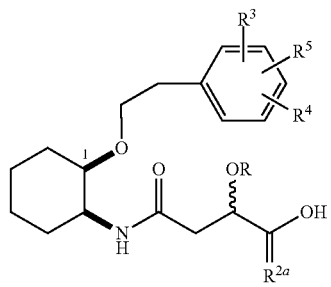

(27)

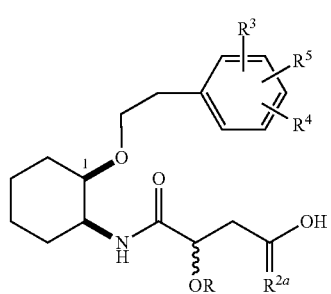

(28)

where each $R^{2a}$ is O or $H_2$, R is H, $C_2$-$C_5$acyl or an oxygen-protecting group and $R^3$, $R^4$ and $R^5$ are as defined above.

In another aspect, this invention is directed to a method of making compounds of formula (II):

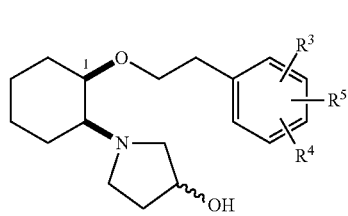

(II)

or a pharmaceutically acceptable salt, ester, amide, complex, chelate, clathrate, solvate, polymorph, stereoisomer, metabolite or prodrug thereof, as a single stereoisomer or as a mixture thereof;

wherein:

$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$ (preferably $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time); and $R^6$, $R^7$, $R^8$, and $R^9$ are each independently selected from hydrogen, acetyl, methanesulfonyl or $C_1$-$C_6$alkyl;

which method comprises:
a) reacting a compound of formula (33):

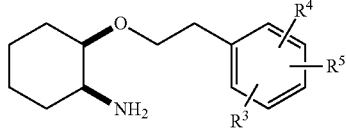

(33)

wherein $R^3$, $R^4$ and $R^5$ are as defined above, with a compound of formula (2a2):

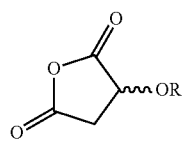

(2a2)

wherein R is H, $C_2$-$C_5$acyl or an oxygen-protecting group (preferably $C_2$-$C_5$acyl), under suitable condensation conditions to form a compound of formula (21b):

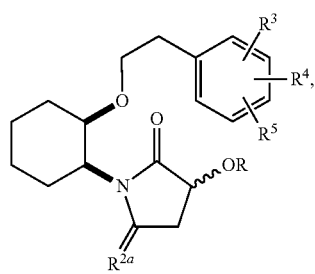

(21b)

wherein R is H, $C_2$-$C_5$acyl or an oxygen-protecting group (preferably $C_2$-$C_5$acyl) and $R^3$, $R^4$ and $R^5$ are as defined above; and
b) reducing the compound of formula (6b) under suitable conditions to form a compound of formula (II), as set forth above.

This method can comprise a nucleophilic displacement step to form the compound of formula (33), wherein the nucleophilic displacement step comprises treating a compound of formula (32):

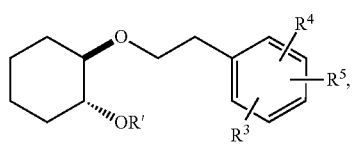

(32)

wherein —OR' is an activated leaving group (preferably an optionally substituted alkysulfonate or an optionally substituted arylsulfonate) and $R^3$, $R^4$ and $R^5$ are as defined above, with an azide under suitable nucleophilic displacement and subsequent reduction conditions to form a compound of formula (33) as set forth above.

This method can further comprise reacting a compound of formula (31):

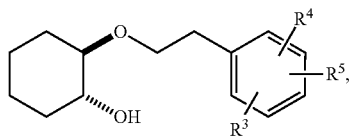

(31)

wherein $R^3$, $R^4$ and $R^5$ are as described above, with an activating agent (preferably an optionally substituted alkylsulfonyl halide or an optionally substituted arylsulfonyl halide) under suitable conditions to form the compound of formula (32) as set forth above.

This method can further comprise a reduction step to form a compound (31), wherein the reduction step comprises treating a compound of formula (14):

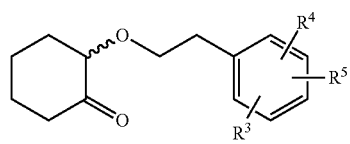

(14)

wherein $R^3$, $R^4$ and $R^5$ are as defined above, under suitable conditions to form the compound of formula (31) as set forth above.

This method can further comprise an etherification step to form a compound of formula (14), wherein the etherification step comprises treating a compound of formula (13):

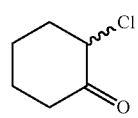

(13)

with a compound of formula (5b):

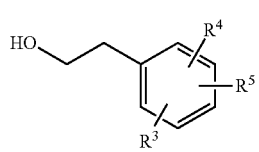

(5b)

wherein $R^3$, $R^4$ and $R^5$ are as defined above, under suitable conditions to form the compound of formula (14), as set forth above.

All of the above methods can further comprise the formation of an acid addition salt of a compound of formula (I) or a compound of formula (II).

In another aspect, this invention is directed to intermediates and compounds prepared by the methods disclosed herein.

In another aspect, this invention is directed to compounds of formula (I).

DETAILED DESCRIPTION OF THE INVENTION

As noted above, the present invention is directed to methods of stereoselectively making compounds of formula (I) and formula (II), as set forth above in the Summary of the Invention.

An understanding of the present invention may be aided by reference to the following definitions and explanation of conventions used herein:

The compounds of formula (I) have an ether oxygen atom at position 1 of a cyclohexane ring, and an amine nitrogen atom at position 2 of the cyclohexane ring, with other positions numbered in corresponding order as shown below in Structure (A):

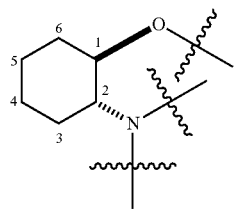

(A)

The bonds from the cyclohexane ring to the 1-oxygen and 2-nitrogen atoms in the above formula are disposed in the trans relationship. Therefore, the stereochemistry of the amine and ether substituents of the cyclohexane ring is (R,R)-trans or (S,S)-trans for the trans-stereoisomers of the compounds of formula (I).

Following the standard chemical literature description practice and as used in this specification, a solid full bond, as illustrated above in Structure (A) and a dashed full bond, as illustrated above in Structure (A), means that the substituents, in this case the amine and ether substituents, are in a trans-configuration with respect to the plane of the cyclohexane ring.

Following the standard chemical literature description practice and as used in this specification, a full wedge bond, as illustrated below in Structure (Aa), means that the substituent bonded to the cyclohexane ring by this bond, in this case the ether substituent, is above the cyclohexane ring plane as illustrated on the page in a two dimensional representation, and a dashed wedge bond, as illustrated below in Structure (Aa), means that the substituent bonded to the cyclohexane ring by this bond, in this case the amine substituent, is below the cyclohexane ring plane as shown on the page in a two dimensional representation;

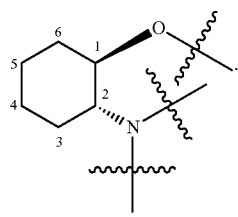

(Aa)

The compounds of formula (II) have an ether oxygen atom at position 1 of a cyclohexane ring, and an amine nitrogen atom at position 2 of the cyclohexane ring, with other positions numbered in corresponding order as shown below in Structure (B):

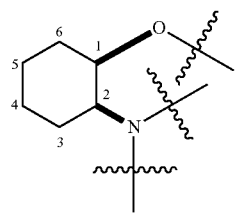

(B)

The bonds from the cyclohexane ring to the 1-oxygen and 2-nitrogen atoms in the above formula are disposed in the cis relationship. Therefore, the stereochemistry of the amine and ether substituents of the cyclohexane ring is (R,S)-cis or (S,R)-cis for the cis-stereoisomers of the compounds of formula (II).

Following the standard chemical literature description practice and as used in this specification, two solid full bonds, as illustrated above in Structure (B) means that the substituents, in this case the amine and ether substituents, are in a cis-configuration with respect to the plane of the cyclohexane ring.

Following the standard chemical literature description practice and as used in this specification, a full wedge bond, as illustrated below in Structure (Ba), means that the substituent bonded to the cyclohexane ring by this bond, in this case the ether and the amine substituent, is above the cyclohexane ring plane as illustrated on the page in a two dimensional representation, and a dashed wedge bond, as illustrated below in Structure (Bb), means that the substituent bonded to the cyclohexane ring by this bond, in this case the ether and the amine substituent, is below the cyclohexane ring plane as shown on the page in a two dimensional representation;

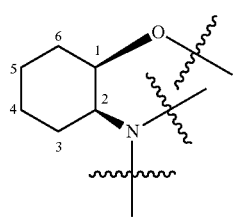

(Ba)

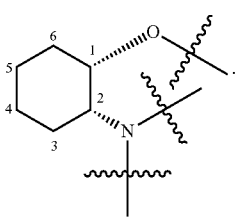

(Bb)

Following the standard chemical literature description practice and as used in this specification, a wavy bond, as illustrated below in the compound of formula (2a2), indicates that the substituent, in this case the —OR substituent, is either below the plane of the cyclohexane ring or above the plane of the cyclohexane ring:

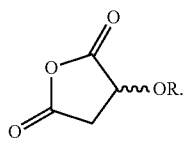

(2a2)

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of formula (I) contain the group (C):

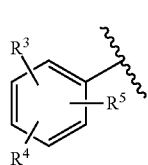

(C)

where the group (C) is intended to encompass groups wherein any ring atom that could otherwise be substituted with hydrogen, may instead be substituted with either $R^3$, $R^4$ or $R^5$, with the proviso that each of $R^3$, $R^4$ and $R^5$ appears once and only once on the ring. Ring atoms that are not substituted with any of $R^3$, $R^4$ or $R^5$ are substituted with hydrogen.

The compounds of the present invention contain at least two asymmetric carbon atoms and thus exist as enantiomers and diastereoisomers. For the present invention, the words diastereomer and diastereoisomer and related terms are equivalent and interchangeable. Unless otherwise indicated, the present invention includes all enantiomeric and diastereoisomeric forms of the aminocyclohexyl ether compounds of formula (I) and compounds of formula (II). Pure stereoisomers, mixtures of enantiomers and/or diastereoisomers, and mixtures of different compounds of the invention are included within the present invention. Thus, compounds of formula (I) and compounds of formula (II) may occur as racemates, racemic or diastereoisomeric mixtures and as individual diastereoisomers, or enantiomers, unless a specific stereoisomer enantiomer or diastereoisomer is identified, with all isomeric forms being included in the present invention. For the present invention, a racemate, diastereoisomeric or racemic mixture does not imply a 50:50 mixture of stereoisomers only. Other enantiomerically or diastereomerically enriched mixtures of varying ratios of stereoisomers are also contemplated. Unless otherwise noted, the phrase "stereoisomerically substantially pure" generally refers to those asymmetric carbon atoms that are described or illustrated in the structural formulae for that compound.

The definition of stereoisomeric purity (or optical purity or chiral purity) and related terminology and their methods of determination (e.g., Optical rotation, circular dichroism etc.) are well known in the art (see e.g., E. L. Eliel and S. H. Wilen, in Stereochemistry of Organic Compounds; John Wiley & Sons: New York, 1994; and references cited therein). The phrase "stereoisomerically substantially pure" generally refers to the enrichment of one of the stereoisomers (e.g., enantiomers or diastereoisomers) over the other stereoisomers in a sample, leading to chiral enrichment and increase in optical rotation activity of the sample. Enantiomer is one of a pair of molecular species that are mirror images of each other and not superimposable. They are "mirror-image" stereoisomers. Diastereoisomers generally refer to stereoisomers not related as mirror-images. Enantiomeric excess (ee) and diastereoisomeric excess (de) are terms generally used to refer the stereoisomeric purity (or optical purity or chiral purity) of a sample of the compound of interest. Their definition and methods of determination are well known in the art and can be found e.g., in E. L. Eliel and S. H. Wilen, in Stereochemistry of Organic Compounds; John Wiley & Sons: New York, 1994; and references cited therein. "Stereoselectively making" refers to preparing the compound having enantiomeric excess (ee) or diastereoisomeric excess (de).

For the present invention, enantiomeric excess (ee) or diastereoisomeric excess (de) in the range of about 50% to about 100% is contemplated. A preferred range of enantiomeric excess (ee) or diastereoisomeric excess (de) is about 60% to about 100%. Another preferred range of enantiomeric excess (ee) or diastereoisomeric excess (de) is about 70% to about 100%. A more preferred range of enantiomeric excess (ee) or diastereoisomeric excess (de) is about 80% to about 100%. Another more preferred range of enantiomeric excess (ee) or diastereoisomeric excess (de) is about 85% to about 100%. An even more preferred range of enantiomeric excess (ee) or diastereoisomeric excess (de) is about 90% to about 100%. Another even more preferred range of enantiomeric excess (ee) or diastereoisomeric excess (de) is about 95% to about 100%. It is understood that the phrase "about 50% to about 100%" includes but is not limited to all the possible percentage numbers and fractions of a number from 50% to 100%. Similarly, the phrase "about 60% to about 100%" includes but is not limited to all the possible percentage numbers and fractions of a number from 60% to 100%; the phrase "about 70% to about 100%" includes but is not limited to all the possible percentage numbers and fractions of a number from 70% to 100%; the phrase "about 80% to about 100%" includes but is not limited to all the possible percentage numbers and fractions of a number from 80% to 100%; the phrase "about 85% to about 100%" includes all but is not limited to the possible percentage numbers and fractions of a number from 85% to 100%; the phrase "about 90% to about 100%" includes but is not limited to all the possible percentage numbers and fractions of a number from 90% to 100%; the phrase "about 95% to about 100%" includes all but is not limited to the possible percentage numbers and fractions of a number from 95% to 100%.

As an example, and in no way limiting the generality of the above, a compound designated with the following formula:'

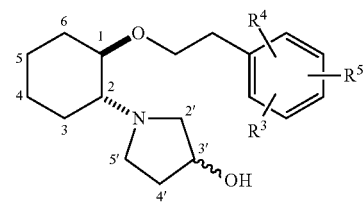

includes at least three chiral centers (the cyclohexyl carbon bonded to the oxygen at the 1 position, the cyclohexyl carbon bonded to the nitrogen at the 2 position, and the pyrrolidinyl carbon bonded to the oxygen at the 3' position) and therefore has at least four separate trans stereoisomers, which are (1R, 2R)-2-[(3R)-Hydroxypyrrolidinyl]-1-($R^3$-, $R^4$- and $R^5$-substituted phenethoxy)cyclohexane; (1R,2R)-2-[(3S)-Hydroxypyrrolidinyl]-1-($R^3$-, $R^4$- and $R^5$-substituted phenethoxy)cyclohexane; (1S,2S)-2-[(3R)-Hydroxypyrrolidinyl]-1-($R^3$-, $R^4$- and $R^5$-substituted phenethoxy)cyclohexane; and (1S,2S)-2-[(3S)-Hydroxypyrrolidinyl]-1-($R^3$-, $R^4$- and $R^5$-substituted phenethoxy)cyclohexane; and, unless the context make plain otherwise as used in this specification, a compound having the formula

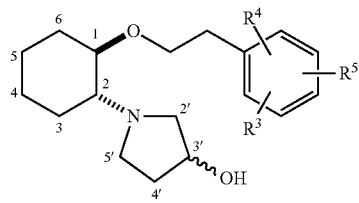

means a composition that includes a component that is either one of the possible pure enantiomeric or diastereisomeric forms of the indicated compound or is a mixture of any two or more of the pure enantiomeric or diastereisomeric forms, where the mixture can include any number of the enantiomeric or diastereisomeric forms in any ratio.

As an example, and in no way limiting the generality of the above, unless the context make plain otherwise as used in this specification, a compound designated with the compound name of (1R,2R)/(1S,2S)-2-[(3R)-hydroxypyrrolidinyl]-1-(3,4-dimethoxyphenethoxy)cyclohexane means a composition that includes a component that is either one or both of the two pure diastereomeric forms of the indicated compound (i.e., (1R,2R)-2-[(3R)-hydroxypyrrolidinyl]-1-(3,4-dimethoxyphenethoxy)cyclohexane or (1S,2S)-2-[(3R)-hydroxypyrrolidinyl]-1-(3,4-dimethoxyphenethoxy)cyclohexane) or is a mixture of the two pure diastereomeric forms, where the mixture can include any relative amount of the two diastereomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R^3$ within the set $R^3$, $R^4$ and $R^5$) is selected without regard the identity of the other member of the set. However, combinations of substituents and/or variables are permissible only if such combinations result in compounds that do not violate the standard rules of chemical valency.

Certain chemical groups named herein are preceded by the shorthand notation "$C_x$-$C_y$," where x and y indicate the lower and upper, respectively, number of carbon atoms to be found in the indicated chemical group. For example; $C_1$-$C_8$alkyl describes an alkyl group, as defined below, having a total of 1 to 8 carbon atoms, and $C_7$-$C_{12}$aralkyl describes an aralkyl group, as defined below, having a total of 7 to 12 carbon atoms. Occasionally, certain chemical groups named herein are preceded by the shorthand notation "$C_z$" where z indicates the total number of carbons to be found in the indicated chemical group. The total number of carbons in the shorthand notation does not include carbons that may exist in substituents of the group described.

In accordance with the present invention and as used herein, the following terms are defined to have following meanings, unless explicitly stated otherwise:

"Acid addition salts" generally refer to but are not limited to those salts which retain the biological effectiveness and properties of the free bases and which are not biologically or otherwise undesirable, formed with inorganic acids such as but not limited to hydrochloric acid, hydrobromic acid, sulfuric acid, nitric acid, phosphoric acid and the like, or acceptable Lewis acids, or organic acids such as but not limited to acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like, and include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

"Acyl" refers to branched or unbranched hydrocarbon fragments terminated by a carbonyl —(C=O)— group containing the specified number of carbon atoms. Examples include acetyl (Ac) [$CH_3C$(=O)—, a $C_2$acyl] and propionyl [$CH_3CH_2C$(=O)—, a $C_3$acyl].

"Alkanoyloxy" refers to an ester substituent wherein the non-carbonyl oxygen is the point of attachment to the molecule. Examples include propanoyloxy [($CH_3CH_2C$(=O)—O, a $C_3$alkanoyloxy] and ethanoyloxy [$CH_3C$(=O)—O—, a $C_2$alkanoyloxy].

"Aralkanoyloxy" refers to an ester substituent wherein the non-carbonyl oxygen is the point of attachment to the molecule and the ester substituent also comprises an alkylene group wherein one of the points of attachment is to an aryl group. An example of an aralkanoyloxy group is $C_6H_5CH_2C$(=O)—O—, a $C_8$aralkanoyloxy group.

"Alkoxy" refers to an oxygen (O)-atom substituted by an alkyl group, for example, alkoxy can include but is not limited to methoxy, which may also be denoted as —$OCH_3$, —OMe or a $C_1$alkoxy.

"Alkoxyalkyl" refers to an alkylene group substituted with an alkoxy group. For example, 2-methoxyethyl [$CH_3OCH_2CH_2$—], 1-methoxyethyl [$CH_3CH(OCH_3)$—] and ethoxymethyl ($CH_3CH_2OCH_2$—] are all $C_3$alkoxyalkyl groups.

"Aralkoxy" refers to an oxygen (O)-atom substituted by an aralkyl group. An example of an aralkoxy group is $C_6H_5CH_2O$—, a $C_7$aralkoxy group.

"Alkoxycarbonyl" refers to an ester substituent wherein the carbonyl carbon is the point of attachment to the molecule. Examples include ethoxycarbonyl [$CH_3CH_2OC$(=O)—, a $C_3$alkoxycarbonyl] and methoxycarbonyl [$CH_3C$(=O)—, a $C_2$alkoxycarbonyl].

"Aralkoxycarbonyl" refers to an ester substituent wherein the carbonyl carbon is the point of attachment to the molecule and the ester substituent also comprises an alkylene group wherein one of the points of attachment is to an aryl group. An example of an aralkoxycarbonyl group is $C_6H_5CH_2O$—C(=O)—, a $C_8$aralkoxycarbonyl group.

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl). Methyl is represented by the symbol Me or $CH_3$.

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group

[—COOH]. Examples include carboxymethyl [HOOC—CH$_2$—, a C$_2$alkylcarboxy] and carboxyethyl [HOOC—CH$_2$CH$_2$—, a C$_3$alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups.

"Aralkyl" refers to an alkylene group wherein one of the points of attachment is to an aryl group. An example of an aralkyl group is the benzyl group (Bn) [C$_6$H$_5$CH$_2$—, a C$_7$aralkyl group].

"Alkylsulfonyl" refers to a radical of the formula —S(O)$_2$R$_a$ where R$_a$ is an alkyl group as defined herein. The alkylsulfonyl group may be optionally substituted by halo or optionally substituted aryl groups, or by other suitable substituents known to one skilled in the art.

"Arylsulfonyl" refers to a radical of the formula —S(O)$_2$R$_b$ where R$_b$ is an optionally substituted aryl group as defined herein. Arylsulfonate groups include, but are not limited to, benzenesulfonate groups, mono- or poly-substituted benzenesulfonate groups, a mono- or poly-halobenzenesulfonate groups, 2-bromobenzenesulfonate group, 2,6-dichlorobenzenesulfonate group, pentafluorobenzenesulfonate group, and a 2,6-dimethylbenzenesulfonate group. The arylsulfonyl group may be optionally substituted by halo or alkyl, or other suitable substituents known to one skilled in the art.

"Cycloalkyl" refers to a ring, which may be saturated or unsaturated and monocyclic, bicyclic, or tricyclic formed entirely from carbon atoms. An example of a cycloalkyl group is the cyclopentenyl group (C$_5$H$_7$—), which is a five carbon (C$_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Halide" or "halo" refers to —Cl, —Br, —F or —I.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include but not limited to furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—CH$_2$OH, a C$_1$hydroxyalkyl) and 1-hydroxyethyl (—CHOHCH$_3$, a C$_2$hydroxyalkyl).

"Thioalkyl" refers to a sulfur atom substituted by an alkyl group, for example thiomethyl (CH$_3$S—, a C$_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be blocked, so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and a pharmaceutically acceptable organic or inorganic acid (acid addition salts) or a pharmaceutically acceptable organic or inorganic base (base addition salts) which retain the biological effectiveness and properties of the compounds of the present invention and which are not biologically or otherwise undesirable. Examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of the present invention" encompass compositions that may contain more than one compound of the present invention formula.

"Clathrates" as used herein refers to substances which fix gases, liquids or compounds as inclusion complexes so that the complex may be handled in solid form and the included constituent (or "guest" molecule) subsequently releases by the action of a solvent or by melting. Clathrates used in the instant invention may be prepared from cyclodextrins. Cyclodextrins are widely known as having the ability to form clathrates with a variety of molecules. See, for example, *Inclusion Compounds*, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2-44; Weber, E. et al., "Functional Group Assisted Clathrate Formation—Scissor-Like and Roof-Shaped Host Molecules", *Topics in Current Chemistry* (1988), Vol. 149, pp. 45-135; and MacNicol, D. D. et al., "Clathrates and Molecular Inclusion Phenomena", Chemical Society Reviews (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344-362; U.S. Pat. No. 4,886,788 (Schering AG); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cyclodextrin" refers to cyclic oligosaccharides consisting of at least six glucopyranose units which are joined together by α(1-4) linkages. The oligosaccharide ring forms a torus with the primary hydroxyl groups of the glucose residues lying on the narrow end of the torus. The secondary glucopyranose hydroxyl groups are located on the wider end. Cyclodextrins have been shown to form inclusion complexes with hydrophobic molecules in aqueous solutions by binding the molecules into their cavities. The formation of such complexes protects the "guest" molecule from loss of evaporation, from attack by oxygen, visible and ultraviolet light and from intra- and intermolecular reactions. Such complexes also serve to "fix" a volatile material until the complex encounters a warm moist environment, at which point the complex will dissolve and dissociate into the guest molecule and the cyclodextrin. For purposes of this invention, the six-glucose unit containing cyclodextrin is specified as α-cyclodextrin, while the cyclodextrins with seven and eight glucose residues are designated as β-cyclodextrin and γ-cyclodextrin, respectively. The most common alternative to the cyclodextrin nomenclature is the naming of these compounds as cycloamyloses.

The synthetic methods/procedures described herein, especially when taken with the general knowledge in the art, provide sufficient guidance to perform the synthesis, isolation, and purification of the compounds of the present invention.

Compounds of the Invention

The compounds of formula (I) and (II), as set forth above in the Summary of the Invention and prepared by the methods disclosed herein, are useful in treating arrhythmias, particularly atrial fibrillation, as disclosed in detail in U.S. Pat. No. 7,057,053 and PCT Published Patent Applications 99/50225 and 2004/099137.

Accordingly, in one embodiment of the invention, the compound of formula (I) prepared by the methods disclosed herein is a compound of the following formula (Ia):

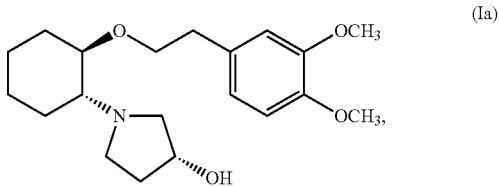 [SMILES: COc1ccc(CCO[C@@H]2CCCC[C@H]2N2CC[C@@H](O)C2)cc1OC]

or a pharmaceutically acceptable salt, ester, amide, complex, chelate, clathrate, solvate, polymorph, metabolite or prodrug thereof, as a single stereoisomer or as a mixture thereof.

This compound is a compound of formula (I) wherein the hydroxy substituent on the pyrrolidinyl ring is in the 3-position, at least one of $R^3$, $R^4$ and $R^5$ is hydrogen and one of the remaining $R^3$, $R^4$ and $R^5$ is methoxy in 3-position of the phenyl ring to which they are attached and the remaining $R^3$, $R^4$ and $R^5$ is methoxy in the 4-position of the phenyl ring to which they are attached, and is named herein as (3R)-1-[(1R,2R)-2-[2-(3,4-dimethoxyphenyl)ethoxy]cyclohexyl]-3-pyrrolidinol.

In another embodiment of the invention, the compound of formula (I) prepared by the methods disclosed herein is a compound selected from the group consisting of the following:

| Structure | Chemical name |
|---|---|
| | (3R)-1-[(1R,2R)-2-[2-(3,4-dimethoxyphenyl)ethoxy]cyclohexyl]-3-pyrrolidinol (Compound of formula (Ia)) |
| | (3R)-1-[(1S,2S)-2-[2-(3,4-dimethoxyphenyl)ethoxy]cyclohexyl]-3-pyrrolidinol (Compound of formula (Ib)) |
| | (3S)-1-[(1R,2R)-2-[2-(3,4-dimethoxyphenyl)ethoxy]cyclohexyl]-3-pyrrolidinol (Compound of formula (Ic)) |

| Structure | Chemical name |
|---|---|
| 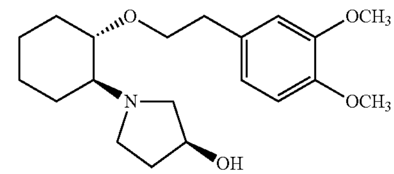 [SMILES: COc1ccc(CCO[C@H]2CCCC[C@@H]2N2CC[C@H](O)C2)cc1OC] | (3S)-1-[(1S,2S)-2-[2-(3,4-dimethoxy-phenyl)ethoxy]cyclohexyl]-3-pyrrolidinol (Compound of formula (Id)) |
| 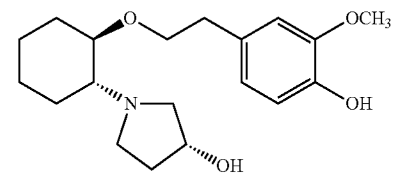 [SMILES: COc1cc(CCO[C@@H]2CCCC[C@H]2N2CC[C@@H](O)C2)ccc1O] | (3R)-1-[(1R,2R)-2-[2-(4-hydroxy-3-methoxy-phenyl)ethoxy]cyclohexyl]-3-pyrrolidinol (Compound of formula (Ie)) |
| 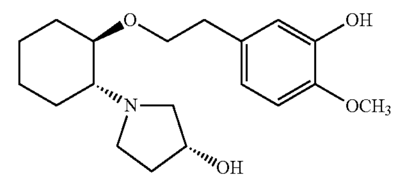 [SMILES: COc1ccc(CCO[C@@H]2CCCC[C@H]2N2CC[C@@H](O)C2)cc1O] | (3R)-1-[(1R,2R)-2-[2-(3-hydroxy-4-methoxy-phenyl)ethoxy]cyclohexyl]-3-pyrrolidinol (Compound of formula (If)) |
| 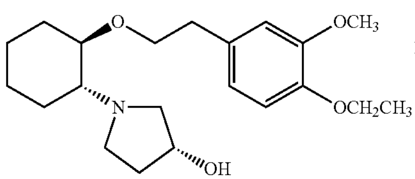 [SMILES: CCOc1ccc(CCO[C@@H]2CCCC[C@H]2N2CC[C@@H](O)C2)cc1OC] | (3R)-1-[(1R,2R)-2-[2-(4-ethoxy-3-methoxy-phenyl)ethoxy]cyclohexyl]-3-pyrrolidinol (Compound of formula (Ig)) |
| | (3R)-1-[(1R,2R)-2-[2-(3-ethoxy-4-methoxy-phenyl)ethoxy]cyclohexyl]-3-pyrrolidinol (Compound of formula (Ih)) | or pharmaceutically acceptable salts, esters, amides, complexes, chelates, clathrates, solvates, polymorphs, metabolites or prodrugs thereof, as a single stereoisomer or mixtures thereof.

In another embodiment of the invention, the compound of formula (I) prepared by the methods disclosed herein is selected from the group consisting of the following:
(3R)-1-[(1R,2R)-2-[2-(3,4-dimethoxy-phenyl)ethoxy]cyclohexyl]-3-pyrrolidinol monohydrochloride;
(3R)-1-[(1S,2S)-2-[2-(3,4-dimethoxy-phenyl)ethoxy]cyclohexyl]-3-pyrrolidinol monohydrochloride;
(3S)-1-[(1R,2R)-2-[2-(3,4-dimethoxy-phenyl)ethoxy]cyclohexyl]-3-pyrrolidinol monohydrochloride;
(3S)-1-[(1S,2S)-2-[2-(3,4-dimethoxy-phenyl)ethoxy]cyclohexyl]-3-pyrrolidinol monohydrochloride;
(3R)-1-[(1R,2R)-2-[2-(4-hydroxy-3-methoxyphenyl) ethoxy]cyclohexyl]-3-pyrrolidinol monohydrochloride;
(3R)-1-[(1R,2R)-2-[2-(3-hydroxy-4-methoxyphenyl) ethoxy]cyclohexyl]-3-pyrrolidinol monohydrochloride;
(3R)-1-[(1R,2R)-2-[2-(4-ethoxy-3-methoxyphenyl)ethoxy] cyclohexyl]-3-pyrrolidinol monohydrochloride; and
(3R)-1-[(1R,2R)-2-[2-(3-ethoxy-4-methoxyphenyl)ethoxy] cyclohexyl]-3-pyrrolidinol monohydrochloride.

Of the above embodiments, a preferred embodiment is (3R)-1-[(1R,2R)-2-[2-(3,4-dimethoxy-phenyl)ethoxy]cyclohexyl]-3-pyrrolidinol monohydrochloride, i.e., the compound of the following formula:

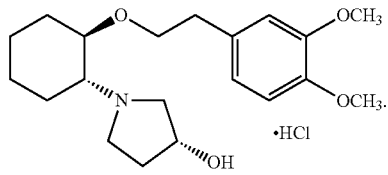 [SMILES: COc1ccc(CCO[C@@H]2CCCC[C@H]2N2CC[C@@H](O)C2)cc1OC ; Cl]

In another embodiment of the invention, a compound of formula (II) prepared by the methods disclosed herein is a compound of the following formula (IIa):

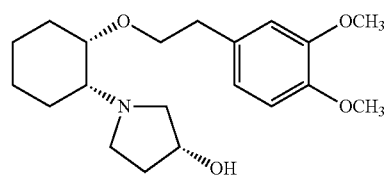 [SMILES: COc1ccc(CCO[C@H]2CCCC[C@H]2N2CC[C@@H](O)C2)cc1OC]

or pharmaceutically acceptable salts, esters, amides, complexes, chelates, clathrates, solvates, polymorphs, metabolites or prodrugs thereof, as a single stereoisomer or a mixture thereof.

This compound is a compound of formula (II) wherein the hydroxy substituent on the pyrrolidinyl ring is in the 3-position, at least one of $R^3$, $R^4$ and $R^5$ is hydrogen and one of the remaining $R^3$, $R^4$ and $R^5$ is methoxy in 3-position of the phenyl ring to which they are attached and the remaining $R^3$, $R^4$ and $R^5$ is methoxy in the 4-position of the phenyl ring to which they are attached, and is named herein as (3R)-1-[(1S,2R)-2-[2-(3,4-dimethoxyphenyl)ethoxy]cyclohexyl]-3-pyrrolidinol.

In another embodiment of the invention, the compound of formula (II) prepared by the methods disclosed herein is a compound selected from the group consisting of the following:

tion also includes the quaternary protonated amine form of the compound that may be prepared by the method of the present invention. These quaternary protonated amine form of the compounds may be present in the solid phase, for example in crystalline or amorphous form, and may be present in solution. These quaternary protonated amine form of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

In another embodiment of the invention, compounds of formula (II) are prepared by methods similar to those

| Structure | Chemical name |
|---|---|
| 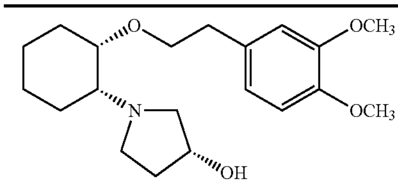 | (3R)-1-[(1S,2R)-2-[2-(3,4-dimethoxyphenyl)ethoxy]cyclohexyl]-3-pyrrolidinol (Compound of formula (IIa)) |
| 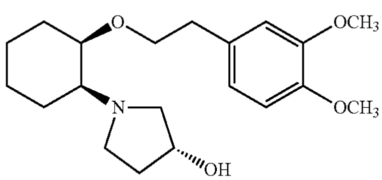 [SMILES: COc1ccc(CCO[C@@H]2CCCC[C@@H]2N2CC[C@@H](O)C2)cc1OC] | (3R)-1-[(1R,2S)-2-[2-(3,4-dimethoxyphenyl)ethoxy]cyclohexyl]-3-pyrrolidinol (Compound of formula (IIb)) |
| 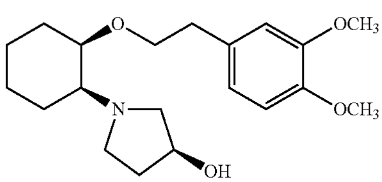 [SMILES: COc1ccc(CCO[C@@H]2CCCC[C@@H]2N2CC[C@H](O)C2)cc1OC] | (3S)-1-[(1R,2S)-2-[2-(3,4-dimethoxyphenyl)ethoxy]cyclohexyl]-3-pyrrolidinol (Compound of formula (IIc)) |
| | (3S)-1-[(1S,2R)-2-[2-(3,4-dimethoxyphenyl)ethoxy]cyclohexyl]-3-pyrrolidinol (Compound of formula (IId)) | or pharmaceutically acceptable salts, esters, amides, complexes, chelates, clathrates, solvates, polymorphs, metabolites or prodrugs thereof, as a single stereoisomer or mixtures thereof.

In another embodiment of the invention, the compound of formula (I) prepared by the methods disclosed herein is selected from the group consisting of the following:
(3R)-1-[(1S,2R)-2-[2-(3,4-dimethoxy-phenyl)ethoxy]cyclohexyl]-3-pyrrolidinol monohydrochloride;
(3R)-1-[(1R,2S)-2-[2-(3,4-dimethoxy-phenyl)ethoxy]cyclohexyl]-3-pyrrolidinol monohydrochloride;
(3S)-1-[(1R,2S)-2-[2-(3,4-dimethoxy-phenyl)ethoxy]cyclohexyl]-3-pyrrolidinol monohydrochloride; and
(3S)-1-[(1S,2R)-2-[2-(3,4-dimethoxy-phenyl)ethoxy]cyclohexyl]-3-pyrrolidinol monohydrochloride.

The present invention also provides protonated versions of all of the compounds described in this specification that may be prepared by the method of the present invention. That is, for each compound described in this specification, the invendescribed herein for the compounds of formula (I) using the appropriate chiral starting materials.

This invention also provides novel intermediates prepared by the methods disclosed herein. The intermediates prepared by the methods disclosed herein for the preparation of compounds of formula (I) are selected from the group consisting of the following:

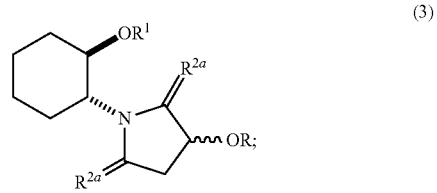

(3)

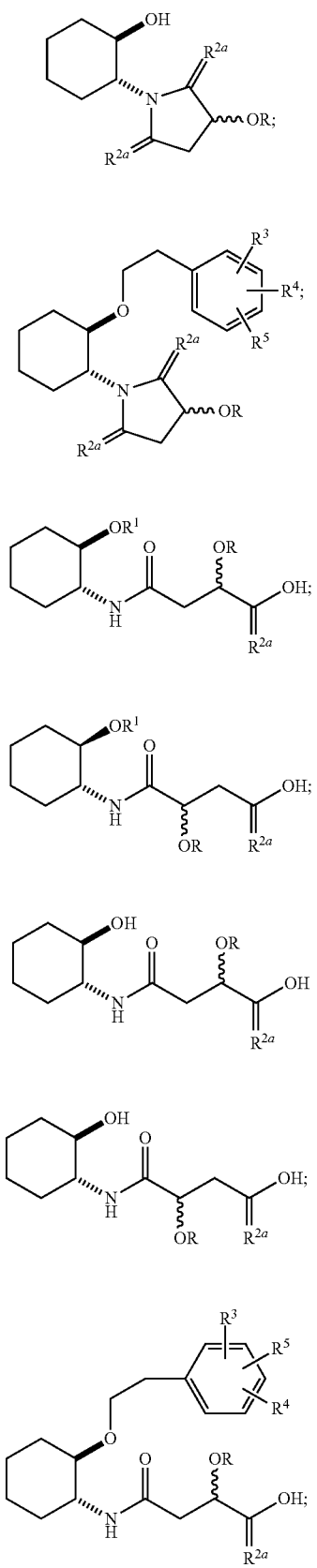

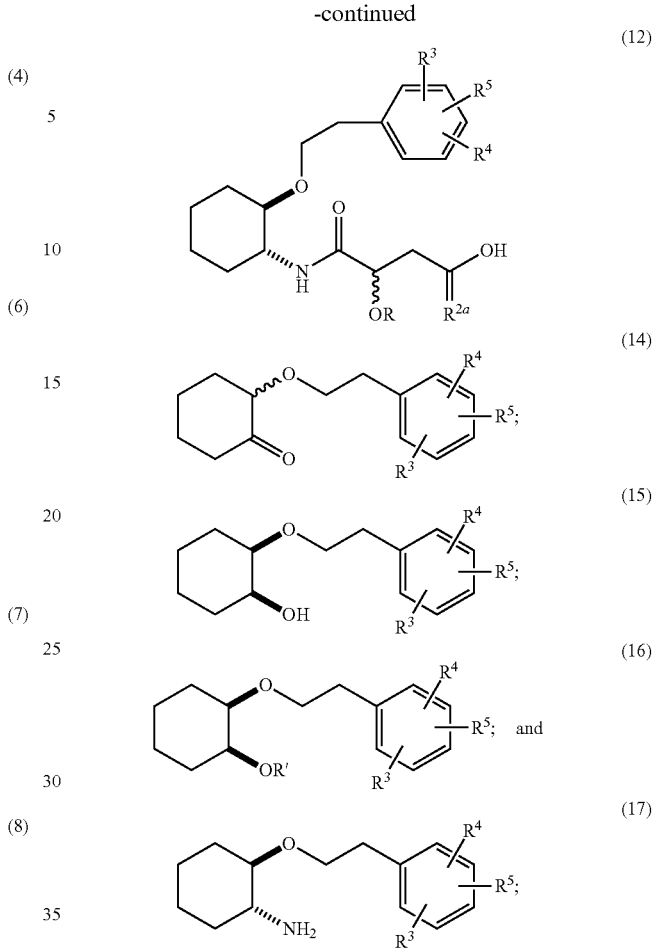

or pharmaceutically acceptable salts, esters, amides, complexes, chelates, clathrates, solvates, polymorphs, metabolites or prodrugs thereof, as a single stereoisomer or a mixture thereof;

wherein:

each $R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, $-CHF_2$, $-SO_2N(R_8)R_9$, $-OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or $N(R_6)R_7$; or each $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time;

each $R^6$, $R^7$, $R^8$, and $R^9$ are each independently selected from hydrogen, acetyl, methanesulfonyl or $C_1$-$C_6$alkyl;

each $R^{2a}$ is O or $H_2$ where at least one $R^{2a}$ in each compound is O;

each R is independently a H, $C_2$-$C_5$acyl or an oxygen-protecting group;

each R' is an optionally substituted alkylsulfonyl or an optionally substituted arylsulfonyl group; and each $R^1$ is an oxygen-protecting group.

The intermediates prepared by the methods disclosed herein for the preparation of compounds of formula (II) are selected from the group consisting of the following:

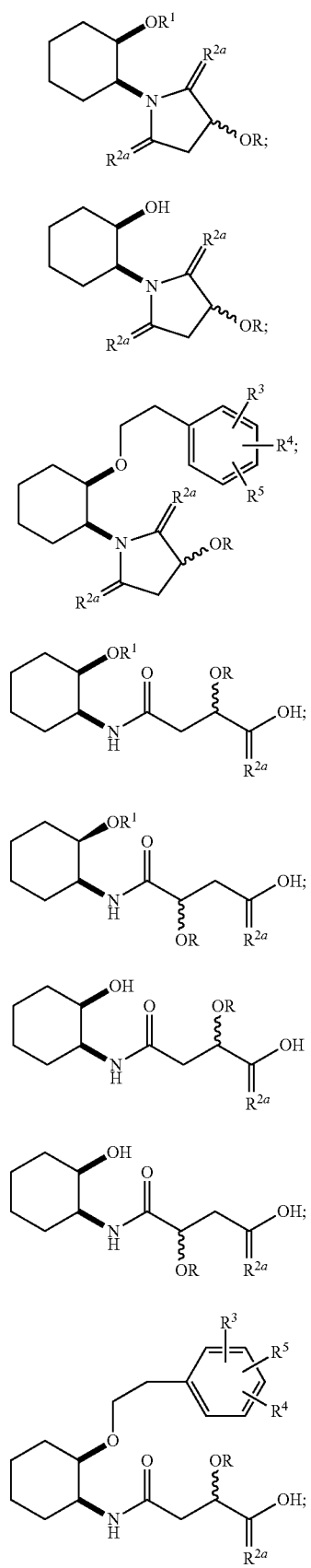

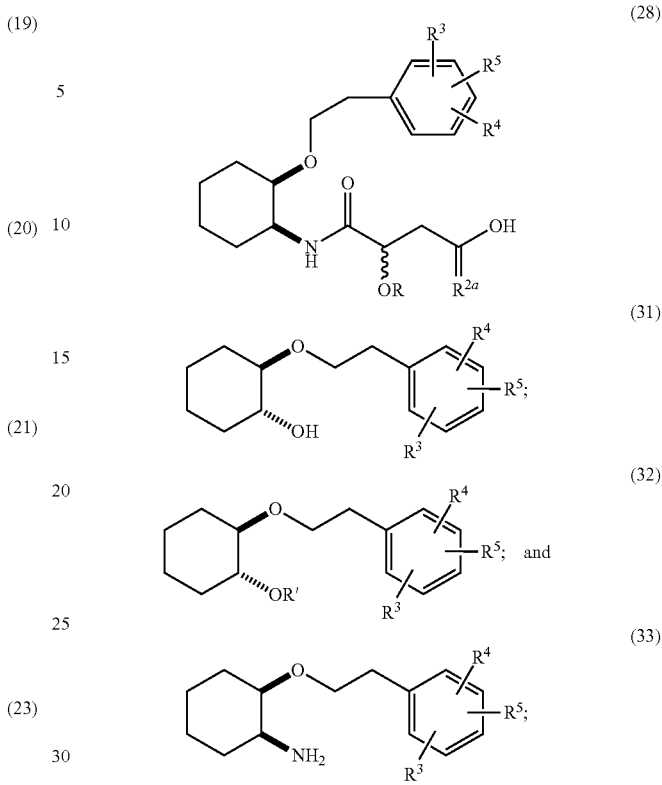

or pharmaceutically acceptable salts, esters, amides, complexes, chelates, clathrates, solvates, polymorphs, metabolites or prodrugs thereof, as a single stereoisomer or a mixture thereof;

wherein:

each $R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$; or each $R^3$, $R^4$ and $R^5$ are independently hydrogen, hydroxy or $C_1$-$C_6$alkoxy; with the proviso that $R^3$, $R^4$ and $R^5$ cannot all be hydrogen at the same time;

each $R^6$, $R^7$, $R^8$, and $R^9$ are each independently selected from hydrogen, acetyl, methanesulfonyl or $C_1$-$C_6$alkyl;

each $R^{2a}$ is O or $H_2$ where at least one $R^{2a}$ in each compound is O;

each R is independently a H, $C_2$-$C_5$acyl or an oxygen-protecting group;

each R is an optionally substituted alkylsulfonyl or an optionally substituted arylsulfonyl group; and each $R^1$ is an oxygen-protecting group.

Methods of the Invention

The compounds of formula (I) and formula (II) contain ether and amino functional groups disposed in a 1,2 arrangement on a cyclohexane ring. Accordingly, the ether and amino functional groups are disposed in either a trans relationship relative to one another or a cis relationship relative to one another and the plane of the cyclohexane ring as shown on the page in a two dimensional representation.

The present invention provides synthetic methodology for the preparation of compounds of formula (I) and compounds of formula (II) as described herein.

The compounds of formula (I) and formula (II) may be prepared from aminoalcohols and alcohols by following the general methods described below. Some general synthetic processes for aminocyclohexyl ethers have been described in WO 99/50225 and references cited therein. Other processes that may be used for preparing compounds of formula (I) and formula (II) are described in PCT Published Patent Application WO 2004/099137, PCT Published Patent Application WO 2005/016242, and U.S. Pat. No. 7,057,053 and other references disclosed therein.

Methods for resolution of diastereomisomeric mixtures or racemic mixtures of the compounds of formula (I) and formula (II) or intermediates prepared herein are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g. preferential crystallization, preferential crystallization in the presence of additives), asymmetric transformation of racemates, chemical separation (e.g. formation and separation of diastereomers such as diastereomeric salt mixtures or the use of other resolving agents; separation via complexes and inclusion compounds), kinetic resolution (e.g. with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, Analytical Chemistry, 2002, 2863-2872).

The present invention also encompasses the preparation of pharmaceutically acceptable salts, esters, amides, complexes, chelates, clathrates, solvates, crystalline or amorphous forms, metabolites, metabolic precursors or prodrugs of the compounds of the present invention. Pharmaceutically acceptable esters and amides can be prepared by reacting, respectively, a hydroxy or amino functional group with a pharmaceutically acceptable organic acid, such as identified above. A prodrug is a drug which has been chemically modified and may be biologically inactive at its site of action, but which is degraded or modified by one or more enzymatic or other in vivo processes to the parent bioactive form. Generally, a prodrug has a different pharmacokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives, which are susceptible to being cleaved by esterases or lipases; (2) terminal peptides, which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, Design of Prodrugs, (1985). Those skilled in the art are well-versed in the preparation of prodrugs and are well-aware of its meaning.

The present invention also encompasses the pharmaceutically acceptable complexes, chelates, metabolites, or metabolic precursors of the compounds of the present invention. Information about the meaning these terms and references to their preparation can be obtained by searching various databases, for example Chemical Abstracts and the U.S. Food and Drug Administration (FDA) website. Documents such as the followings are available from the FDA: Guidance for Industry, "In Vivo Drug Metabolism/Drug Interaction Studies—Study Design, Data Analysis, and Recommendations for Dosing and Labeling", U.S. Department of Health and Human Services, Food and Drug Administration, Center for Drug Evaluation and Research (CDER), Center for Biologics Evaluation and Research (CBER), November 1999. Guidance for Industry, "In Vivo Drug Metabolism/Drug Interaction Studies in the DRUG DEVELOPMENT PROCESS: STUDIES IN VITRO", U.S. Department of Health and Human Services, Food and Drug Administration, Center for Drug Evaluation and Research (CDER), Center for Biologics Evaluation and Research (CBER), April 1997.

The synthetic procedures described herein, especially when taken with the general knowledge in the art, provide sufficient guidance to those of ordinary skill in the art to perform the synthesis, isolation, and purification of the compounds of the present invention. Further, it is contemplated that the individual features of these embodiments and examples may be combined with the features of one or more other embodiments or examples.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one of ordinary skill in the art and as described herein.

The use of protecting groups is described in detail in Green, T. W. and P. G. M. Wuts, *Protective Groups in Organic Synthesis* (1999), 3rd Ed., Wiley.

Any or all of the compounds set forth in any of the Reaction Schemes herein may be converted to a pharmaceutically acceptable salt by reaction with an inorganic or organic acid under appropriate conditions known to one skilled in the art.

In addition, any or all of the compounds set forth in the Reaction Schemes herein may be subjected to standard deprotection conditions in order to arrive at the desired functional group.

In addition, at any point in any of the Reaction Schemes disclosed herein, the starting material, an intermediate or a product so formed may be subjected to a resolution process whereby individual enantiomers or diastereomers are separated into starting materials, intermediates or products that are in stereoisomerically substantially pure form. These individual enantiomers, diastereomers or mixtures thereof, can then be used in the method disclosed in any of the Reaction Schemes herein to prepare stereoisomerically substantially pure forms of the compounds of formula (I), or mixtures thereof. Methods for resolution of racemates or other stereoisomeric mixtures are well known in the art (e.g., E. L. Eliel and S. H. Wilen, in *Stereochemistry of Organic Compounds*; John Wiley & Sons: New York, 1994; Chapter 7, and references cited therein). Suitable processes may include but are not limited to separation of stereoisomers by crystallization (e.g. preferential crystallization, preferential crystallization in the presence of additives), asymmetric transformation of racemates or diastereomeric mixtures, chemical separation (e.g. formation and separation of diastereomers such as diastereomeric salt mixtures or the use of other resolving agents; separation via complexes and inclusion compounds), kinetic resolution (e.g. with titanium tartrate catalyst), enzymatic resolution (e.g., lipase mediated, carbonyl reductase mediated) and chromatographic separation (e.g., HPLC with chiral stationary phase and/or with simulated moving bed technology, or supercritical fluid chromatography and related techniques) (see e.g., T. J. Ward, Analytical Chemistry, 2002, 2863-2872).

In the following Reaction Schemes and Preparations, the following common abbreviations and acronyms are used:
Et$_2$O (diethyl ether)
MTBE (methyl tert-butyl ether)
TMSOTf (trimethylsilyl triflate)
TMS-Cl (trimethylsilyl chloride)
p-TSA (para-toluenesulfonic acid).

The following Reaction Schemes provide a de novo synthesis of the pyrrolidinol ring in the compounds of formula (I) while retaining the trans relative configuration in the starting materials.

One general method of stereoselectively preparing the compounds of formula (I) is illustrated below in Reaction not limited to, the following radicals wherein the ⁓ line in the following represents the ⁓ bond between R$^2$ and the OR group in compounds of formula (2):

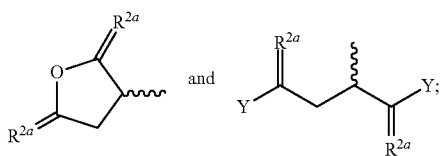

where each R$^{2a}$ is O or H$_2$ (provided that at least one R$^{2a}$ is O in each structure), and each Y is halo; R is H, C$_2$-C$_5$acyl or an oxygen-protecting group; R$^3$, R$^4$ and R$^5$ are as defined above in the Summary of the Invention for compounds of formula (I); and Q represents a good leaving group:

REACTION SCHEME 1A

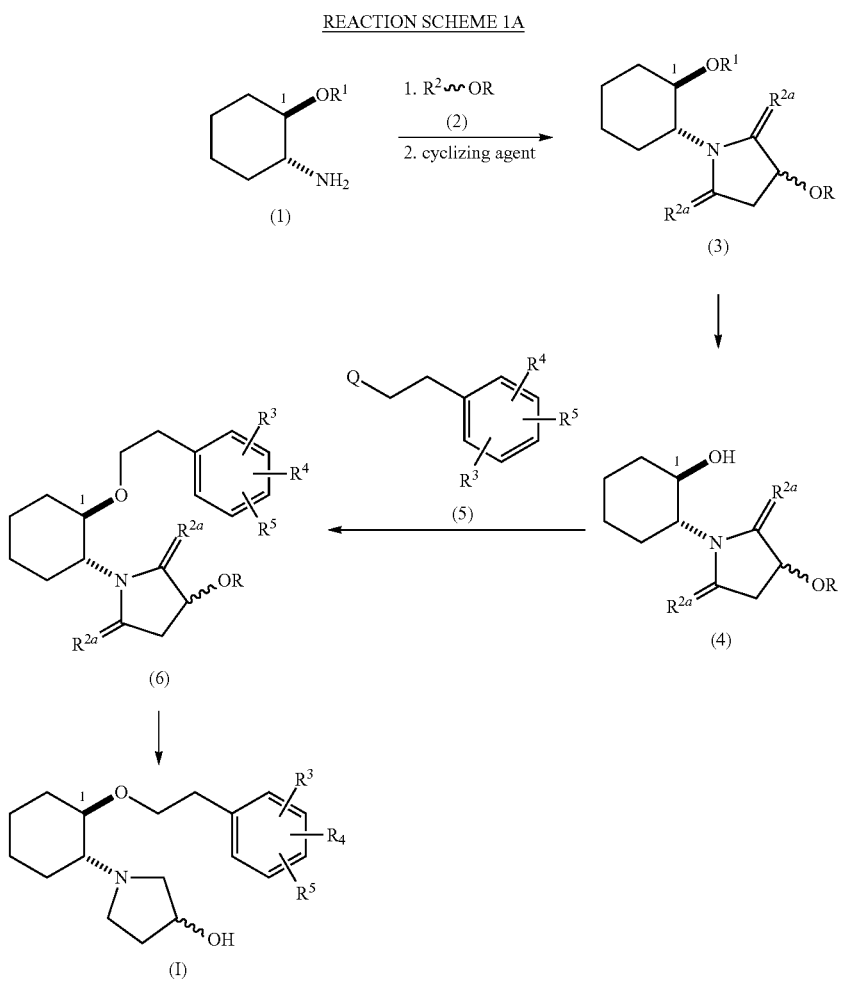

Scheme 1A wherein R$^1$ is an oxygen-protecting group, preferably optionally substituted benzyl; R$^2$ is selected to form a compound of formula (3) upon treatment with the compound of formula (1), followed by cyclization, and is selected, but is In general, the compounds of formula (I) are prepared in Reaction Scheme 1A by first treating a compound of formula (1) with a compound of formula (2) in an aprotic solvent, such as toluene, dichloromethane, or ethyl acetate, followed by the treatment with an cyclizing agent, such as a $C_2$-$C_5$ acyl halide or $C_2$-$C_5$ acyl anhydride, at temperatures of between about 0° C. to reflux temperature, preferably at reflux temperature, to form a compound of formula (3). Alternatively, a compound of formula (1) is first treated with a compound of formula (2) in an aprotic solvent to yield a corresponding intermediate, which is then treated with a cyclizing agent to form compounds of formula (3). Compounds of formula (3) are then subjected to standard deprotection conditions known to one skilled in the art, such as hydrogenation in the presence of a catalyst under appropriate conditions, to form the compound of formula (4). The compound of formula (4) is then treated with a compound of formula (5) under conditions such that the stereochemical spatial arrangement of the hydroxyl group of compound of formula (4) is retained in the resulting compound of formula (6). Such conditions include, but are not limited to, the presence of a Lewis or Brønsted acid, (for example, $HBF_4$, $BF_3.Et_2O$, TMSOTf, ZnCl, TMS-Cl, $CF_3SO_3H$, HCl, $CH_3SO_3H$, $H_2SO_4$, p-TSA, camphorsulfonic acid, $CF_3SO_3Ag$), preferably a catalytic amount of the Lewis or Brønsted acid, in an aprotic solvent. The compound of formula (5) may be optionally protected prior to the treatment with compound of formula (4). The compound of formula (6) so formed is then subjected to standard reducing conditions known to one skilled in the art to arrive at the compound of formula (I).

Alternatively, another general method of stereoselectively preparing the compounds of formula (I) is illustrated below in Reaction Scheme 1B wherein Q, R, $R^{2a}$, $R^2$, $R^3$, $R^4$ and $R^5$ are as defined above in Reaction Scheme 1A:

REACTION SCHEME 1B

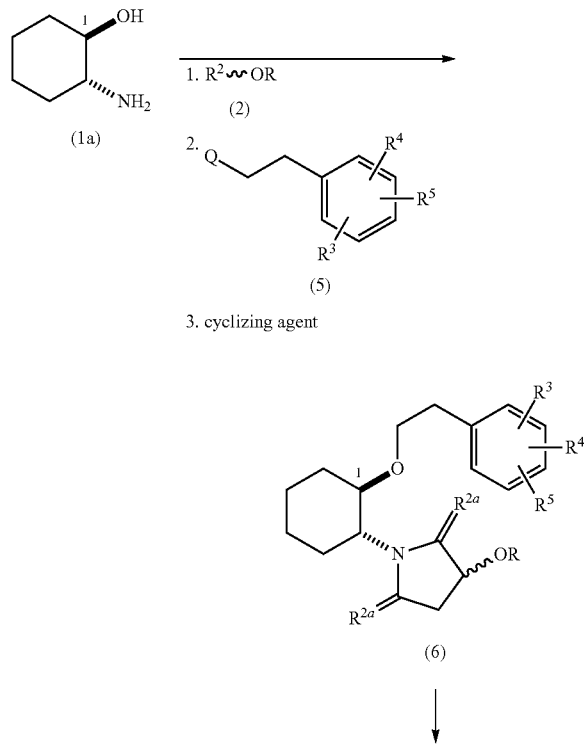

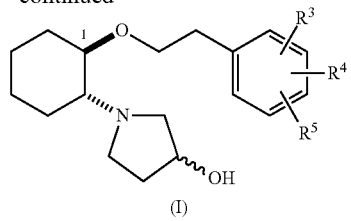

In general, the compounds of formula (I) are prepared in Reaction Scheme 1B by first treating a compound of formula (1a) with a compound of formula (2) in an aprotic solvent, such as toluene, dichloromethane, or ethyl acetate, followed by the treatment of the resulting product with a compound of formula (5) under conditions such that upon reaction with the compound of formula (5) the stereochemical spatial arrangement of the hydroxyl group at the 1-position of the compound of formula (1a) is retained in the resulting product. Such conditions include, but are not limited to, the presence of a Lewis or Bronsted acid, (for example, $HBF_4.Et_2O$, $BF_3.Et_2O$, TMSOTf, ZnCl, TMS-Cl, $CF_3SO_3H$, HCl, $CH_3SO_3H$, $H_2SO_4$, p-TSA, camphorsulfonic acid, $CF_3SO_3Ag$), preferably a catalytic amount of the Lewis or Brønsted acid, in an aprotic solvent. The resulting product is then treated with a cyclizing agent, such as a $C_2$-$C_5$ acyl chloride or acetic anhydride, at temperatures of between about 0° C. to reflux temperature, preferably at reflux temperature, to form a compound of formula (6). The compound of formula (6) so formed is then subjected to standard reducing conditions known to one skilled in the art to arrive at the compound of formula (I).

The oxygen-protecting groups for $R^1$ and R can be any oxygen-protecting group for alcohols as set forth in T. W. Green and P. G. M. Wuts, *Protective Groups in Organic Synthesis*, Wiley-Interscience, New York, N.Y. (1999) ("Green") for the protection of alcohols. Preferably the oxygen-protecting group for $R^1$ is an optionally substituted benzyl group, wherein the optional substituents on the benzyl group are as set forth in Green. Preferred oxygen-protecting groups for R are $C_2$-$C_5$ acyl groups. The compound of formula (1) wherein $R^1$ is benzyl can be obtained from BASF (Switzerland) (see, PCT Published Patent Application WO 96/23894). Compounds of formula (1) can also be obtained from ASDI (601 Interchange Blvd. Newark, Del. 19711, USA) and ABCR GmbH & Co. KG (Inn Schlehert 10, 76187 Karlsruhe, Germany) or can be prepared according to methods known to one skilled in the art.

Compounds of formula (5) can be prepared by methods known to one skilled in the art or by methods disclosed herein. The "Q" in the compounds of formula (5) represents a good leaving group which results in the formation of a compound of formula (6) such that the trans relative configuration or spatial arrangement of the hydroxyl group on the carbon at the 1-position in the compound of formula (4) or the compound of formula (1a) is retained in that of the compound of formula (6), resulting in the retention of the trans relative configuration or spatial arrangement of the amine and ether substituents on the cyclohexyl ring in the compounds of formula (I). Haloacetimidate (e.g. 2,2,2-trifluoroacetimidate or 2,2,2-trichloroacetimidate) is a preferred example of a compound of formula (5) containing a suitable Q group for the purposes of this invention. For some compounds of the formula (4) in Reaction Scheme 1A and/or the intermediates formed in Reaction Scheme 1B, it may be necessary to introduce appropriate protecting groups to the compounds of formula (5)

prior to the etherification step with the compound of formula (5) being performed. Suitable protecting groups and the corresponding deprotection conditions are set forth in, for example, T. W. Green and P. G. M. Wuts, *Protective Groups in Organic Synthesis*, Wiley-Interscience, New York, N.Y. (1999) and references cited therein.

Other examples of suitable Q groups for the compounds of formula (5) are provided below in Table A. (For a review of the application of various examples of Q in the formation of an ether compound with an alcohol see, for example, Toshima K. and Tatsuta K. Chem. Rev. 1993, 93, 1503, Tsuda T., Nakamura S, and Hashimoto S. Tetrahedron Lett. 2003, 44, 6453, Martichonok V. and Whitesides G. M. J. Org. Chem., 1996, 61, 1702 and references cited therein.). As noted below in Table A, in addition to haloacetimidate (e.g. trihaloacetimidate such as 2,2,2-trifluoroacetimidate or 2,2,2-trichloroacetimidate) and other imidate esters (e.g. pentafluorobenzimidate), other examples of suitable Q groups for the compounds of formula (5), include, but are not limited to, O-carbonates and S-carbonates, including imidazole carbonates and imidazolethiocarbonates. Phosphate examples of a Q group include a diphenyl phosphate, a diphenylphosphineimidate, a phosphoroamidate and a O-sulfonyl group.

TABLE A

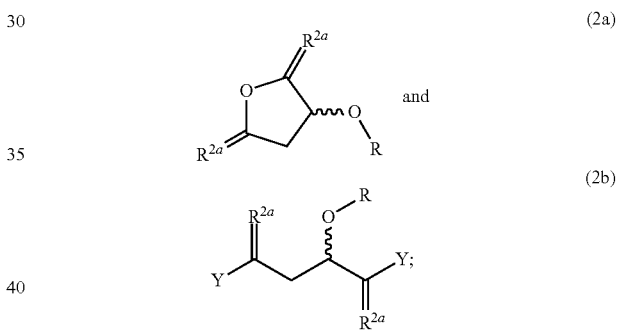

Compounds of formula (2) are chosen to yield compounds of formula (3) in Reaction Scheme 1A and compounds of formula (6) in Reaction Scheme 1B above. Examples of compounds of formula (2) include, but are not limited to, the following compounds:

wherein R is an oxygen-protecting group; each $R^{2a}$ is O or $H_2$, where at least one $R^{2a}$ group in each structure is O, and Y is halo. Compounds of formula (2a) can be prepared, for example, from malic acid and $C_2$-$C_5$ acyl chloride according to the procedures described in Henrot, S. et al., *Synthetic Communications* 1986, 16(2), 183-190, or can be prepared according to methods known to one skilled in the art. Compounds of formula (2b) are commercially available or can be prepared according to methods known to one skilled in the art. Additional protection and deprotection steps, depending on the blocking groups, may be necessary to arrive at the desired product.

Several of the steps disclosed in the above Reaction Scheme 1A or Reaction Scheme 1B may be combined without isolation of the product so formed or removal of the solvent. Specific examples of such "one-pot" synthesis are disclosed herein.

The advantages of the above Reaction Scheme 1A and Reaction Scheme 1B over published processes for preparing compounds of formula (I) are as follows:
  1. Each reaction step can be easily monitored by HPLC.
  2. The overall yield of compound of formula (I) is greater than the overall yield of compound of formula (I) in the published processes for compounds of formula (I).

3. Only a catalytic amount of acid is needed for the etherification step instead of a supra-stoichiometric amount (>1 eq), although a stoichiometric or suprastoichiometric amount of acid can be used.

4. Several steps can be combined in one reaction vessel which would reduce processing time and production plant usage.

the preparation of compounds of formula (I) wherein R is $C_2$-$C_5$acyl; each $R^{2a}$ is O or $H_2$ where at least one $R^{2a}$ in each structure is O; $R^3$, $R^4$ and $R^5$ are as defined above in the Summary of the Invention for compounds of formula (I); AcCl represents $C_2$-$C_5$acyl chloride; $R^1$ represents an oxygen-protecting group, preferably optionally substituted benzyl, and Q represents a leaving group:

REACTION SCHEME 1A1

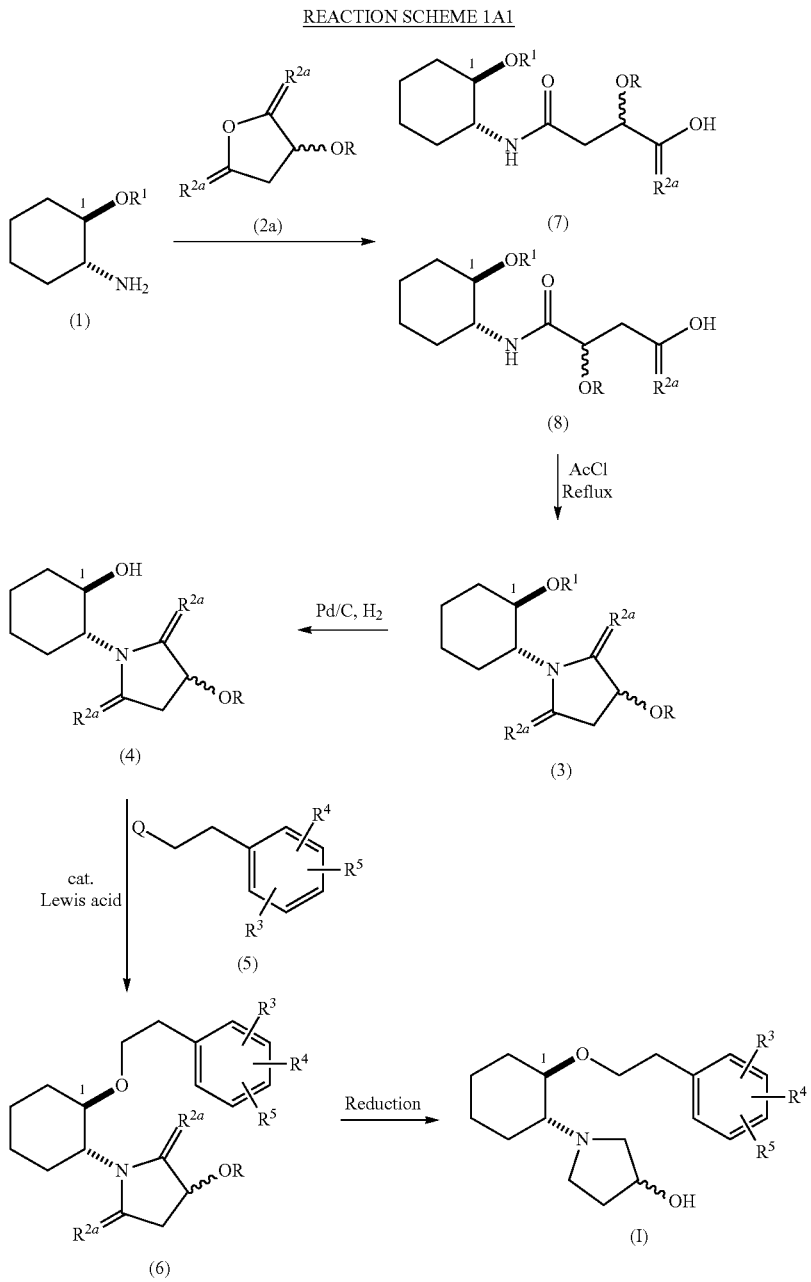

5. The process is an efficient enantioselective process in that no undesired isomers are generated, thereby avoiding costly resolution steps, or the loss of costly material in the form of undesired isomers.

A more specific method of stereoselectively preparing the compounds of formula (I) as set forth above in Reaction Scheme 1A is illustrated below in Reaction Scheme 1A1 for In general, the amine of formula (1) is first condensed with a compound of formula (2a) in a suitable solvent (such as toluene, dichloromethane, or ethyl acetate) to give compound of formula (7) or formula (8). When the N-acylation of compound of formula (1) was shown to be complete by HPLC, the solvent was removed under vacuum. The mixture of the compounds of formula (7)/(8) was refluxed in an $C_2$-$C_5$acyl halide, preferably acetyl chloride, to effect cyclization to give succinimide of formula (3) according to the procedures similar to those described in Naylor, A. et al., 4-[(Alkylamino)methyl]furo[3,2-c]pyridines: A New Series of Selective K-Receptor Agonists, *J. Med. Chem.* (1994), 37, 2138-2144. Addition of an $C_2$-$C_5$ acyl halide, preferably acetyl chloride, to the mixture of the compounds of formula (7)/(8) without first removing the solvent was shown to also be useful for cyclization.

After the removal of excess acetyl chloride, compound of formula (3) was then subjected to standard hydrogenolysis condition (Pd/C—$H_2$—in a suitable solvent, such as toluene, methanol, ethyl acetate, Ra—Ni—$H_2$, Pt/C—$H_2$) at ambient temperature to remove the oxygen-protecting group to give compound of formula (4). Etherification of compound of formula (4) with compound of formula (5) under catalytic Lewis acid conditions (e.g., $HBF_4$ etherate) gave the corresponding imido-ether of formula (6). Finally, successive reduction of compound of formula (6) with a suitable reducing agent, for example, for example, borane, $NaBH_4$/Lewis acid, $KBH_4$, Red-Al (see, e.g., Alimardanov et al., *Org. Proc. Res. & Dev.* (2004), 8, 834-837) or lithium aluminum hydride (see, e.g., Naylor, A. et al. cited above), provided the compound of formula (I) as a free base. Subsequent treatment of the compound of formula (I) with hydrogen chloride in diethyl ether and trituration in ethyl acetate gave the hydrochloride salt of the compound of formula (I).

Alternatively, the steps in the above Reaction Scheme may be performed without isolation of the intermediates and/or without removal of solvent (i.e., without solvent exchange) to form the compound of formula (6), which can then be treated as set forth above to form the compound of formula (I). An example of this alternative preparation of a compound of formula (I) is described in more detail below in the Preparations.

A more specific method of stereoselectively preparing the compounds of formula (I) as set forth above in Reaction Scheme 1A is illustrated below in Reaction Scheme 1A2 for the preparation of the compound of formula (Ia), which is a compound of formula (I), where $R^1$ represents an oxygen-protecting group, preferably optionally substituted benzyl, and Ac represents acetyl:

REACTION SCHEME 1A2

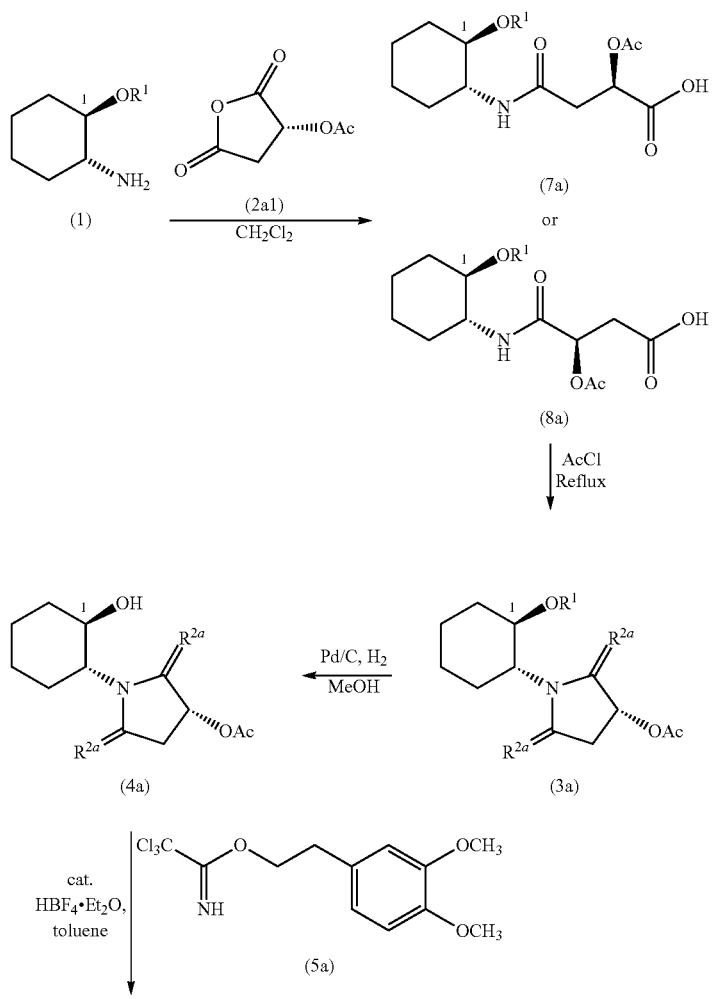

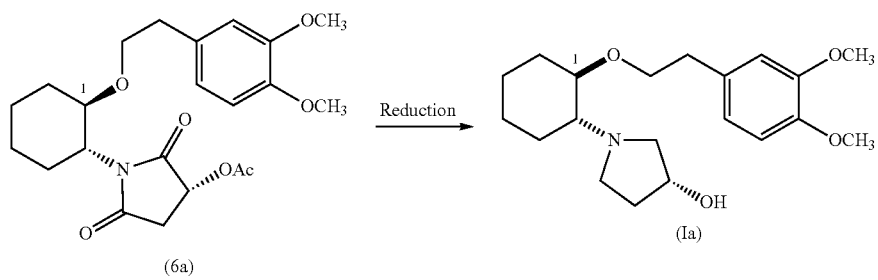

The specific experimental conditions and parameters for the above Reaction Scheme 1A2 are described in more detail below in the Preparations. It is also understood, in light of this disclosure, that the following compounds of formula (Ib), formula (Ic), formula (Id), formula (Ie), formula (If), formula (Ig) and formula (Ih), and their pharmaceutically acceptable salts, can be prepared in a similar manner as described above and below in the Preparations for compounds of formula (Ia) and its pharmaceutically acceptable salt by utilizing the appropriate starting materials and reagents:

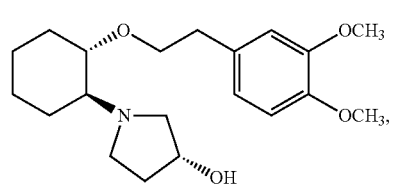
(Ib)

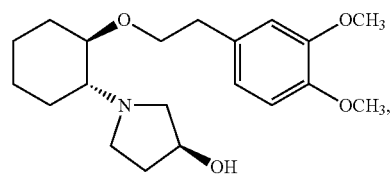
(Ic)

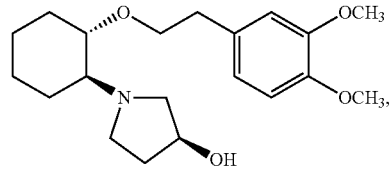
(Id)

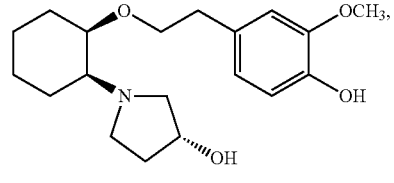
(Ie)

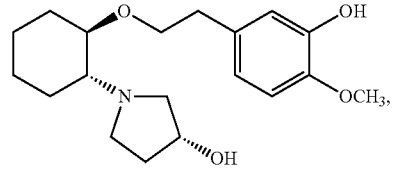
(If)

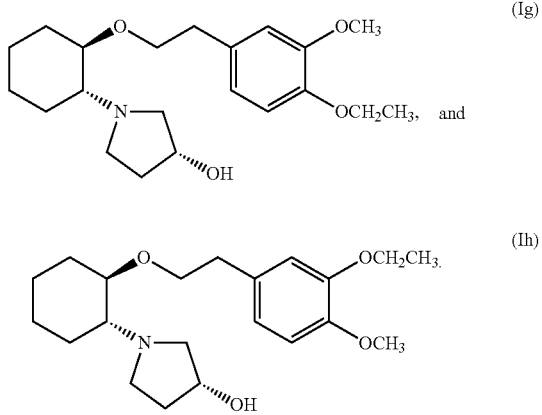

A more specific method of stereoselectively preparing the compounds of formula (I) as set forth above in Reaction Scheme 1B is illustrated below in Reaction Scheme 1B1 for the preparation of compounds of formula (I) where R is an oxygen protecting group; Ac is $C_2$-$C_5$acyl; each $R^{2a}$ is O or $H_2$ where at least one $R^{2a}$ in each structure is O; $R^3$, $R^4$ and $R^5$ are as defined above in the Summary of the Invention and Q represents a leaving group:

REACTION SCHEME 1B1

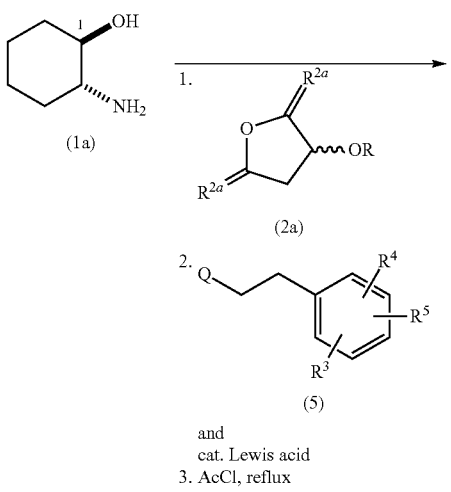

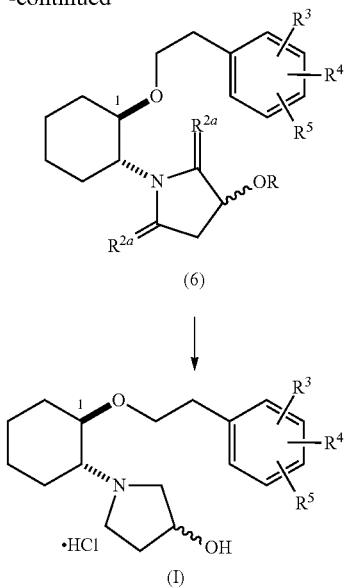

The starting material, trans-aminocyclohexanol (compound of formula (1a)), can be prepared from a mixture of cis- and trans-stereoisomers by standard resolution techniques or by methods known to one skilled in the art. In general, the method disclosed in Reaction Scheme 1B1 is a "one-pot" process of acylation, acetimidate ether coupling, and cyclization, i.e., the process does not require the isolation of intermediates from the reaction mixture and/or the removal of solvents, to give compound of formula (6), which is then subjected to standard reducing conditions to form the compound of formula (I). More specifically, the acylation was accomplished using 1.05 equivalents of the compound of formula (2a) at ambient temperature in a suitable solvent such as toluene, dichloromethane, or ethyl acetate. The addition of compound of formula (5), preferably trichloroacetimidate, and then a catalytic amount of a Lewis acid, preferably tetrafluoroboric acid etherate, yielded a mixture of components in which the desired material could be identified by HPLC. The reaction mixture was then treated with an $C_2$-$C_5$acyl halide, preferably acetyl chloride, and refluxed for 1 hour to give the imido ether of formula (6), which was isolated from the reaction mixture by standard isolation techniques, such as flash column chromatography. Subsequent reduction of the compound of formula (6) and treatment under standard acid addition salt formation, such as treatment with hydrogen chloride in diethyl ether and trituration in ethyl acetate, gave the salt, preferably the hydrochloride salt, of the compound of formula (I).

Alternatively, Reaction Scheme 1B may be performed as shown below in Reaction Scheme 1B2 where R is $C_2$-$C_5$acyl; each $R^{2a}$ is O or $H_2$ where at least one $R^{2a}$ in each structure is O; $R^3$, $R^4$ and $R^5$ are as defined above in the Summary of the Invention and Q represents a leaving group:

REACTION SCHEME 1B2

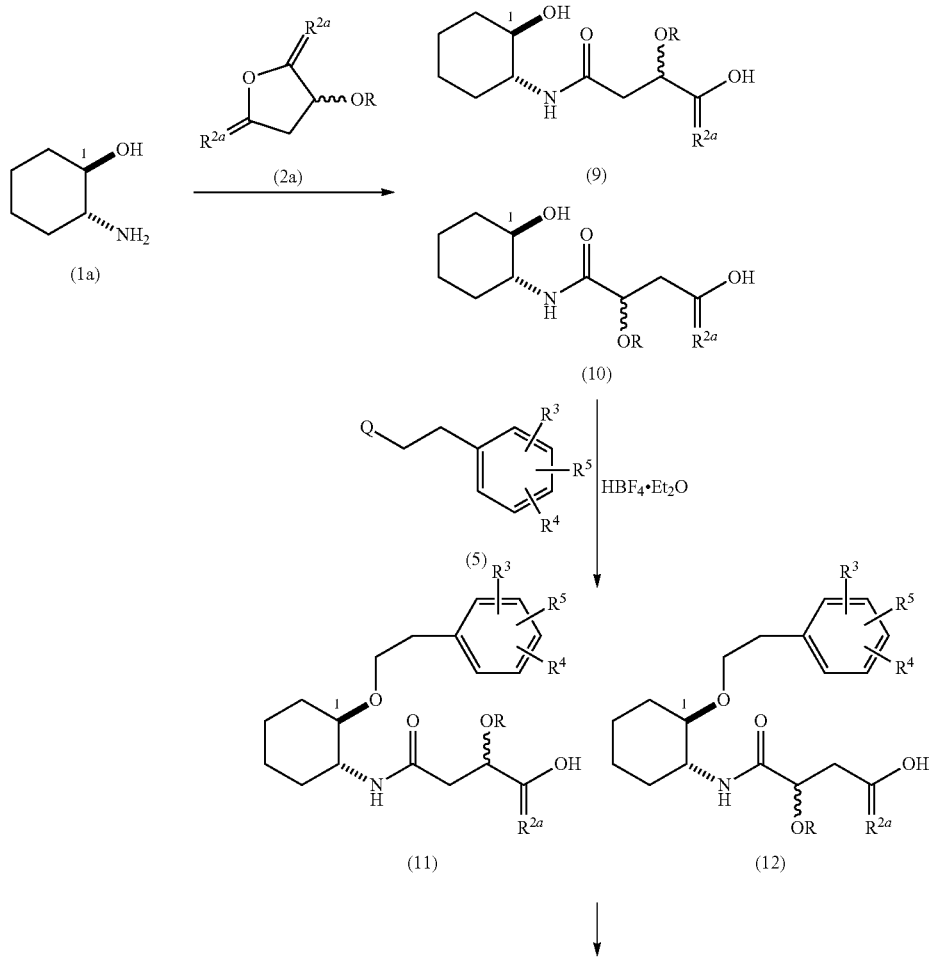

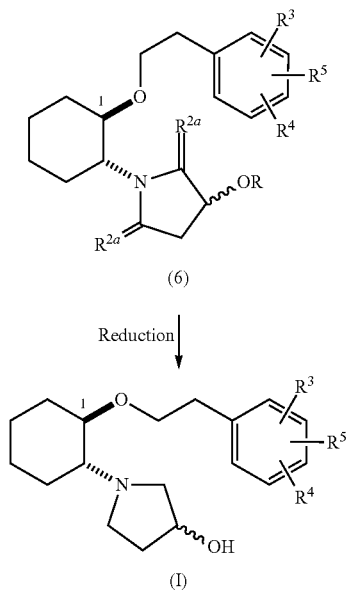

(6)

Reduction ↓

(I)

Briefly, the acylation of the starting material (1a) was accomplished by condensing the compound with the anhydride of formula (2a) under suitable condensation conditions, such as ambient temperature in dichloromethane, to give a mixture of the compounds of formula (9) and formula (10). The mixture of these compounds was then treated with a compound of formula (5), followed by the addition of a catalytic amount of a Lewis acid, preferably tetrafluoroboric acid etherate, under suitable conditions to yield a mixture of compounds of formula (11) and formula (12). The mixture of these compounds was then treated under suitable cyclization conditions, such as treatment with a cyclizing agent, such as acetyl chloride, and refluxed for 1 hour to give the compound of formula (6), which was isolated from the reaction mixture by standard isolation techniques, such as flash column chromatography. Subsequent treatment of the compound of formula (6) under standard reducing conditions provided the compound of formula (I), which was then treated under standard acid addition salt formation conditions, such as treatment with hydrogen chloride in diethyl ether and trituration in ethyl acetate, to give the salt, preferably the hydrochloride salt, of the compound of formula (I).

Compounds of formula (I) can also be stereoselectively prepared by another method of the invention as shown below in Reaction Scheme 1C where R is $C_2$-$C_5$acyl, R' is an optionally substituted alkylsulfonyl or an optionally substituted arylsulfonyl group, X is a halide, $R^3$, $R^4$ and $R^5$ are as defined above in the Summary of the Invention:

REACTION SCHEME 1C

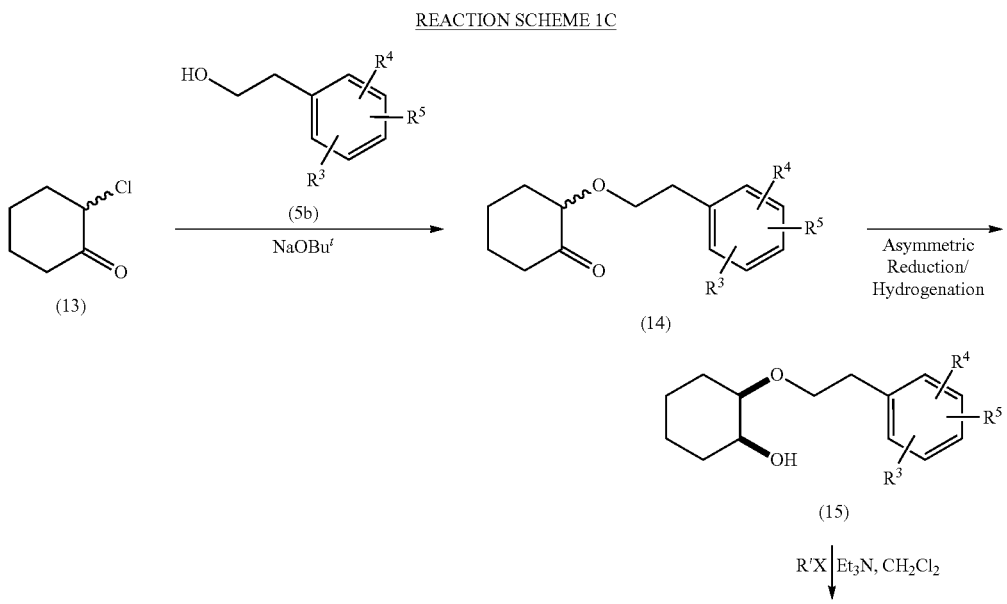

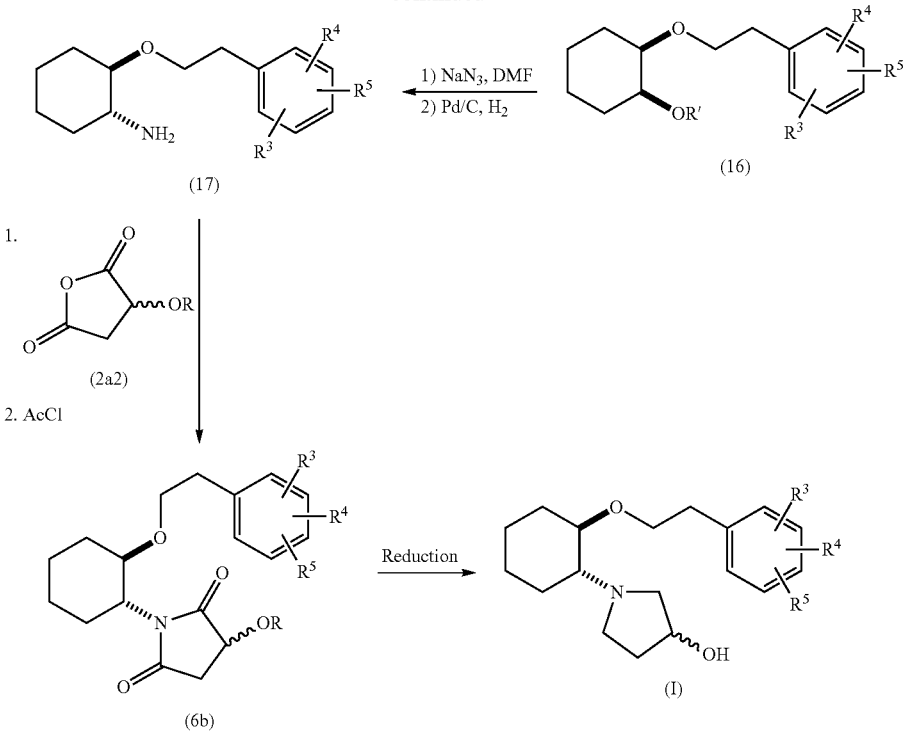

The starting material, 2-chlorocyclohexanone (13), is commercially available, for example, from Aldrich Chemical Co.

In general, 2-chlorocyclohexanone (13) was readily transformed into the corresponding keto-ether of formula (14) by reaction with the sodium alkoxide ion of 3,4-dimethoxyphenethyl alcohol of formula (5b) under suitable conditions. Asymmetric reduction using the process disclosed in U.S. Pat. No. 6,617,475 or the chiral ruthenium catalyst under Noyori's reaction conditions (see, e.g., Ohkmura, T. et al., *J. Org. Chem.* (1996), Vol. 61, pp. 4872) gave compound of formula (15). Compound of formula (15) was then converted into the compound (16) under suitable conditions such that —OR' becomes an activated leaving group, such as the treatment of the compound of formula (15) with a compound of the formula R'X, where R' is an optionally substituted alkylsulfonyl or an optionally substituted arylsulfonyl group and X is a halide, under basic conditions. The leaving group (—O—R') in compound of formula (16) may be, but is not limited to, an optionally substituted alkanesulfonate such as a trifluoromethanesulfonate group ($CF_3SO_3$—) or a mesylate group (MsO—), an optionally substituted arylsulfonate such as a benzenesulfonate group ($PhSO_3$—), a mono- or poly-substituted benzenesulfonate group, a mono- or poly-halobenzenesulfonate group, a 2-bromobenzenesulfonate group, a 2,6-dichlorobenzenesulfonate group, a pentafluorobenzenesulfonate group, a 2,6-dimethylbenzenesulfonate group, a tosylate group (TsO—) or a nosylate (NsO—), or other equivalent good leaving groups. The hydroxy group in the compound of formula (15) may also be converted into other suitable leaving groups according to procedures well known in the art. The leaving group may be any suitable leaving group on reaction with a nucleophilic reactant with inversion of stereochemical configuration known in the art, including but not limited to compounds disclosed in M. B. Smith and J. March in "March's Advanced Organic Chemistry", Fifth edition, Chapter 10, John Wiley & Sons, Inc., New York, N.Y. (2001). Treatment of the compound of formula (16) under nucleophilic displacement (SN2) conditions using sodium azide, followed by hydrogenation in the presence of a palladium catalyst provided the compound of formula (17). The compound of formula (17) was then condensed with substituted malic anhydride of formula (2a2) in dichloromethane to give the compound of formula (6b), which was then subjected to standard reducing conditions described herein to provide the compound of formula (I), which is then treated under standard acid addition salt formation conditions, such as treatment with hydrogen chloride in diethyl ether and trituration in ethyl acetate, to give the salt, preferably the hydrochloride salt, of the compound of formula (I).

The following Reaction Schemes provide a de novo synthesis of the pyrrolidinol ring in the compounds of formula (II) while retaining the cis relative configuration in the starting materials.

In general, compounds of formula (II) as set forth above in the Summary of the Invention can be prepared in a similar manner as described above in Reaction Scheme 1A and Reaction Scheme 1B using the following starting material, respectively:

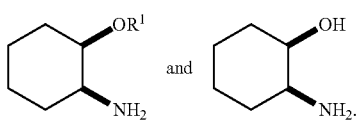

The same reagents and conditions that were employed to make the compounds of formula (I) in the foregoing Reaction Schemes may be used to make the compounds of formula (II) from the above starting materials. For example, compounds of formula (II) may be prepared as set forth in the following Reaction Scheme 2A wherein the cyclizing agent, the compounds of formula (2), and R, $R^1$, $R^2$, $R^{2a}$, $R^3$, $R^4$, $R^5$ and Q are defined as in Reaction Scheme 1A above:

REACTION SCHEME 2A

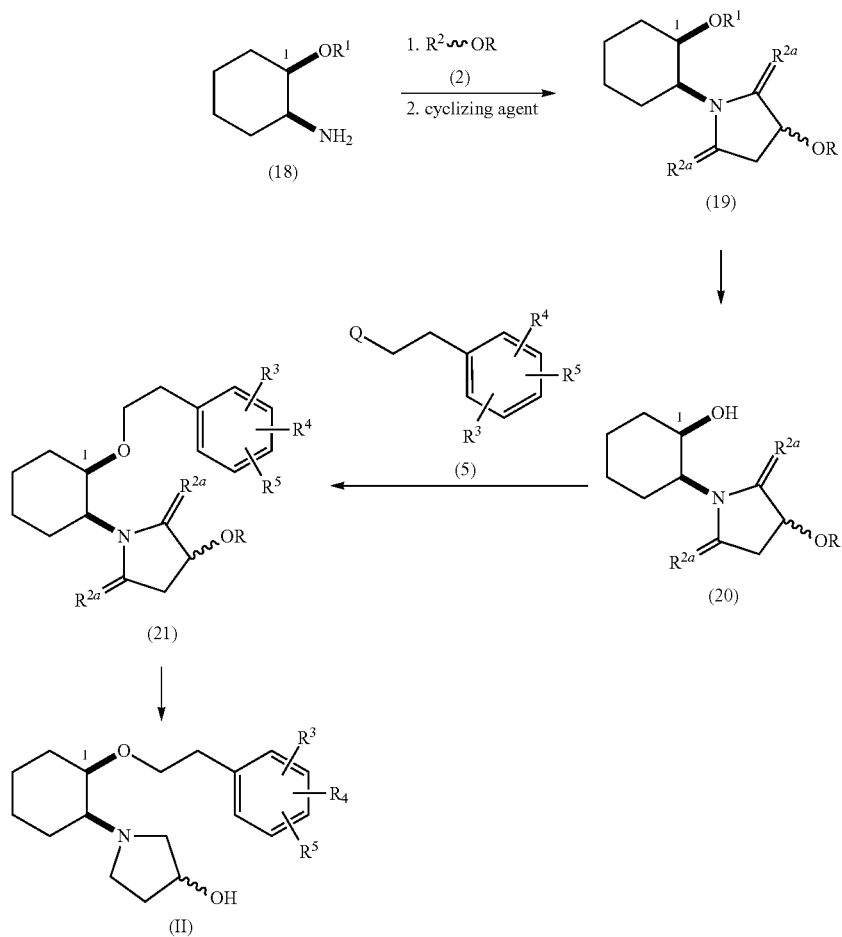

In general, compounds of formula (II) can be prepared as set forth above in Reaction Scheme 2A in a similar manner as the preparation of compounds of formula (I) as set forth above in Reaction Scheme 1A.

Alternatively, another general method of stereoselectively preparing the compounds of formula (II) is illustrated below in Reaction Scheme 2B wherein Q, R, $R^{2a}$, $R^3$, $R^4$ and $R^5$ are as defined above in Reaction Scheme 2A:

REACTION SCHEME 2B

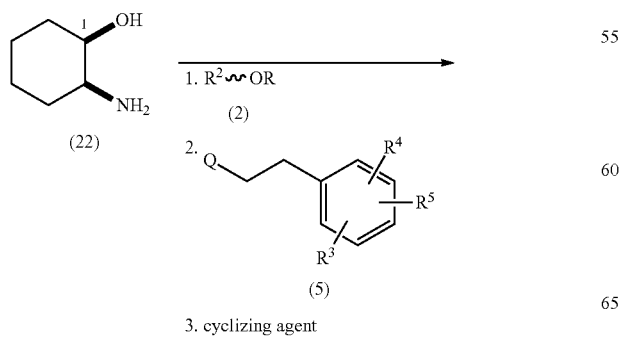

-continued

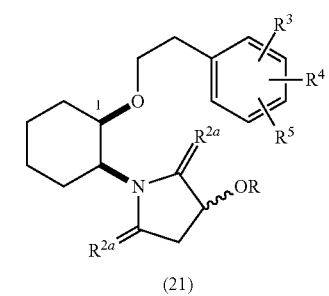

In general, compounds of formula (II) can be prepared by Reaction Scheme 2B above in a similar manner as the preparation of compounds of formula (I) in Reaction Scheme 1B above.

In both Reaction Scheme 2A and Reaction Scheme 2B, the "Q" in the compounds of formula (5) represents a good leaving group which results in the formation of a compound of formula (21) such that the cis relative configuration or spatial arrangement of the hydroxyl group on the carbon at the 1-position in the compound of formula (20) or the compound of formula (22) is retained in that of the compound of formula (21), resulting in the retention of the cis relative configuration or spatial arrangement of the amine and ether substituents on the cyclohexyl ring in the compounds of formula (II).

A more specific method of stereoselectively preparing the compounds of formula (II) as set forth in Reaction Scheme 2A above is illustrated below in Reaction Scheme 2A1 wherein R, $R^{2a}$, $R^3$, $R^4$, $R^5$, AcCl, $R^1$, and Q are as defined above for Reaction Scheme 1A1:

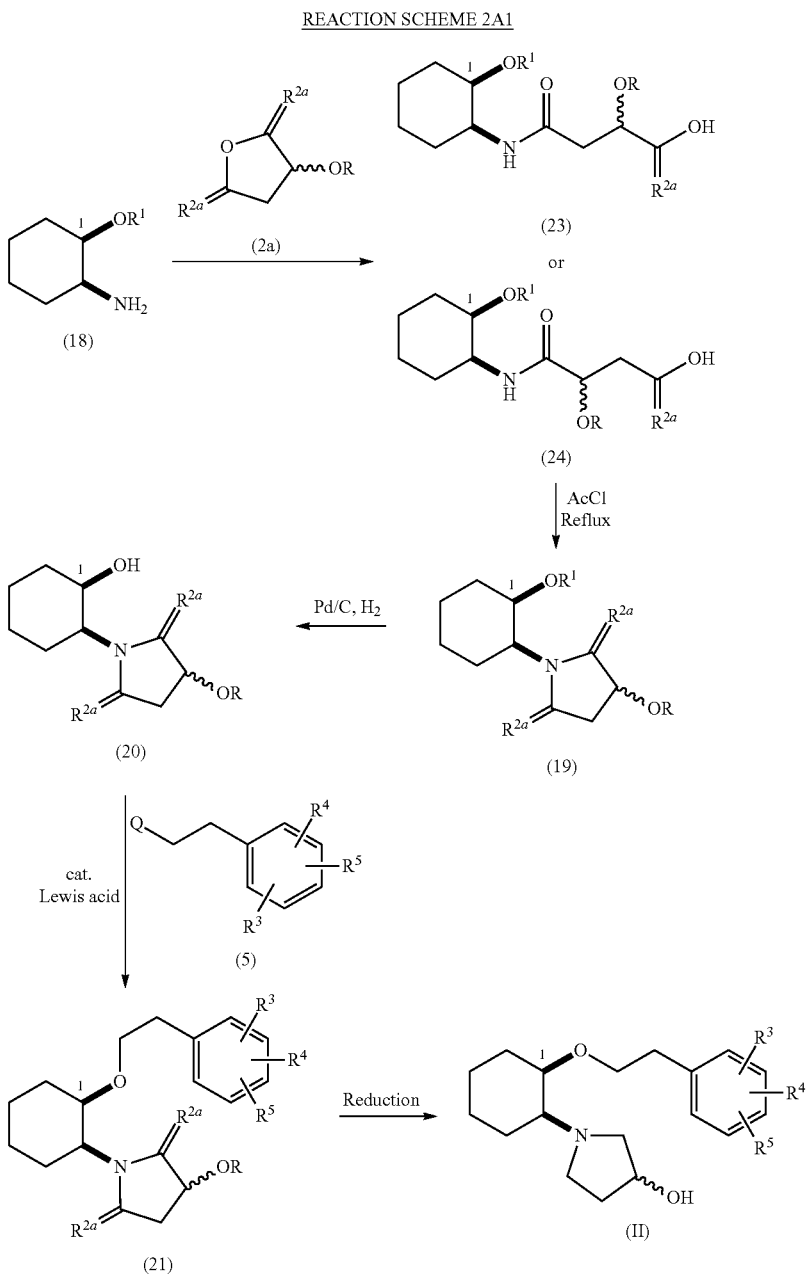

REACTION SCHEME 2A1

In general, compounds of formula (II) are prepared by the method disclosed above in Reaction Scheme 2A1 in the same manner as the compounds of formula (I) are prepared in Reaction Scheme 1A1.

Alternatively, the steps in the above Reaction Scheme may be performed without isolation of the intermediates and/or without removal of the solvent (i.e., without solvent exchange) to form the compound of formula (21), which can then be treated as set forth above to form the compound of formula (II).

A more specific method of stereoselectively preparing the compounds of formula (II) as set forth above in Reaction Scheme 2A is illustrated below in Reaction Scheme 2A2 for the preparation of the compound of formula (IIa), which is a compound of formula (II), where $R^1$ represents an oxygen-protecting group, preferably optionally substituted benzyl, and Ac represents acetyl:

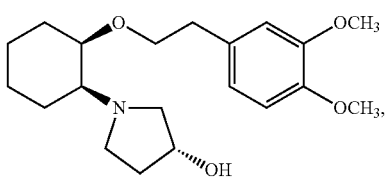
(IIb)

REACTION SCHEME 2A2

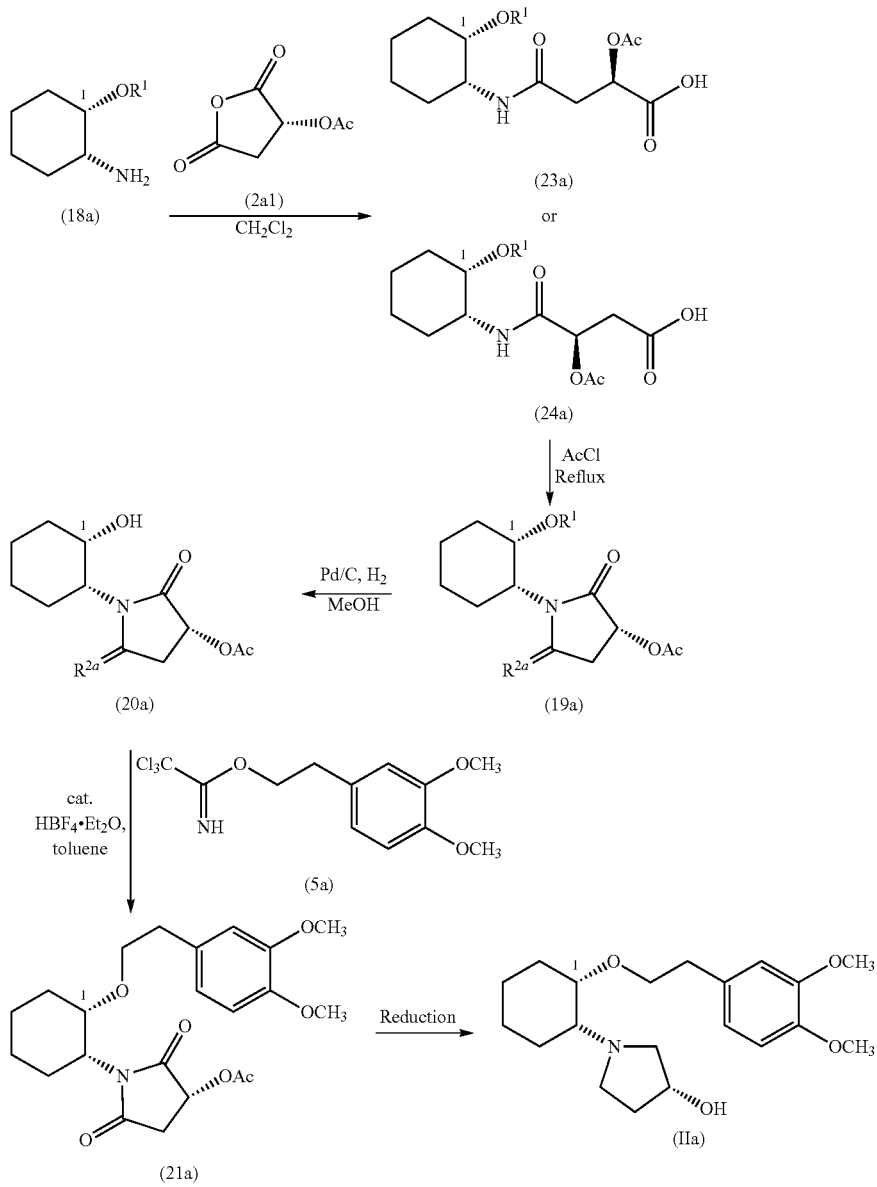

In general, the compound of formula (IIa) can be prepared in Reaction Scheme 2A2 above in a similar manner as the compounds of formula (I) are prepared in Reaction Scheme 1A2 above. It is understood that, in light of this disclosure, the following compounds of formula (IIb), formula (IIc) and formula (IId) can be prepared in a similar manner as described above by utilizing the appropriate starting materials and reagents:

-continued

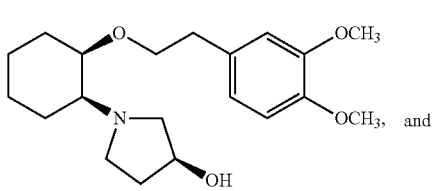
(IIc)

-continued

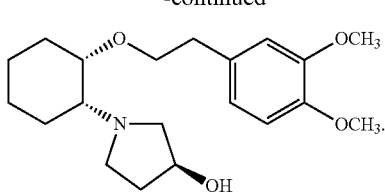
(IId)

A more specific method of stereoselectively preparing the compounds of formula (II) as set forth above in Reaction Scheme 2B is illustrated below in Reaction Scheme 2B1 for the preparation of compounds of formula (II) where R, Ac, $R^{2a}$, $R^3$, $R^4$, $R^5$ and Q are defined as above in Reaction Scheme 1B1:

REACTION SCHEME 2B1

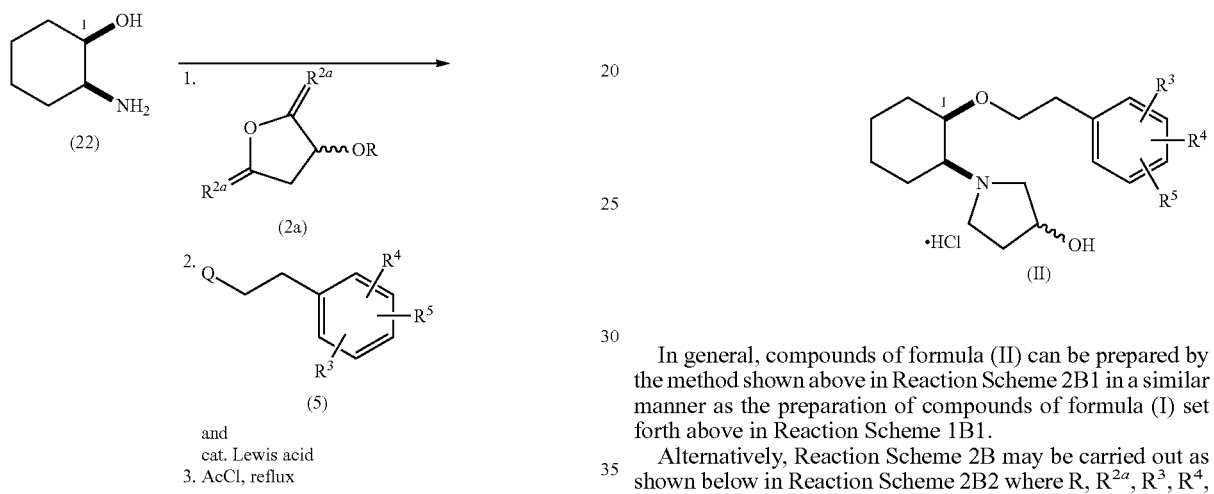

-continued

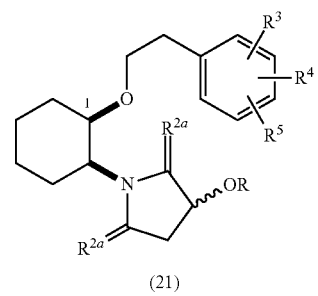
(21)

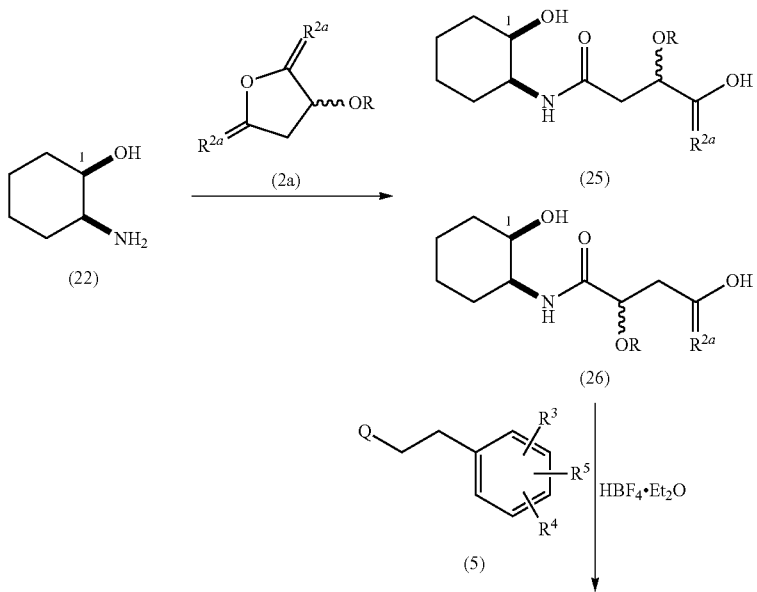
(II)

In general, compounds of formula (II) can be prepared by the method shown above in Reaction Scheme 2B1 in a similar manner as the preparation of compounds of formula (I) set forth above in Reaction Scheme 1B1.

Alternatively, Reaction Scheme 2B may be carried out as shown below in Reaction Scheme 2B2 where R, $R^{2a}$, $R^3$, $R^4$, $R^5$ and Q are defined as above in Reaction Scheme 1B2:

REACTION SCHEME 2B2

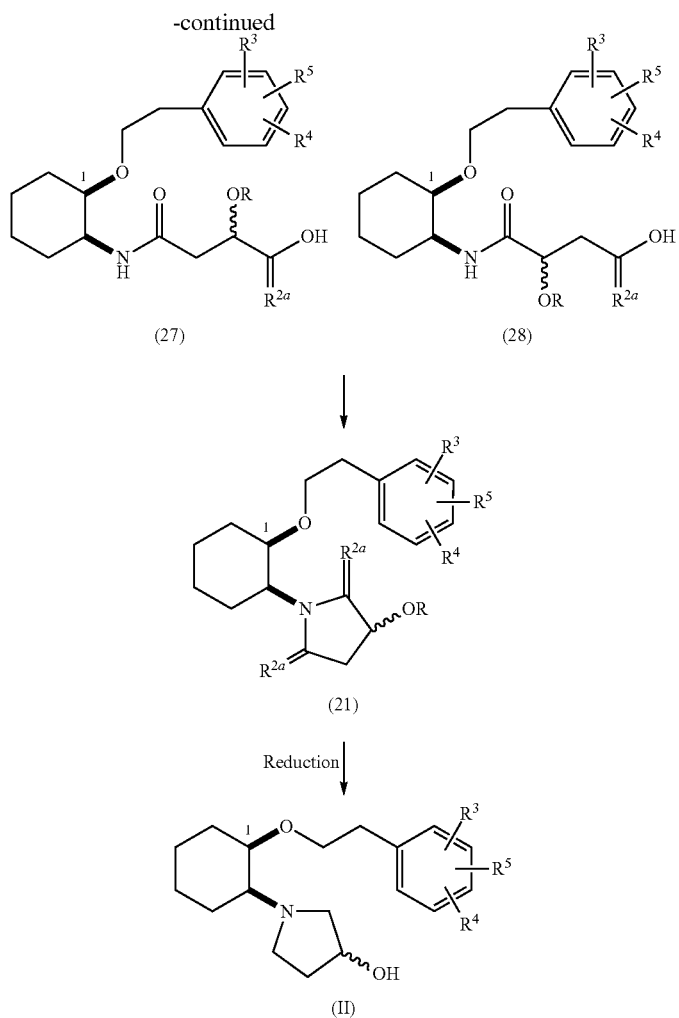

In general, compounds of formula (II) can be prepared as set forth above in Reaction Scheme 2B2 in a similar manner as the preparation of compounds of formula (I) set forth above in Reaction Scheme 1B2.

Compounds of formula (II) can also be stereoselectively prepared by another method of the invention as shown below in Reaction Scheme 2C where R is $C_2$-$C_5$ acyl, R' is an optionally substituted alkylsulfonyl or an optionally substituted arylsulfonyl group, $R^3$, $R^4$ and $R^5$ are as defined above in the Summary of the Invention:

REACTION SCHEME 2C

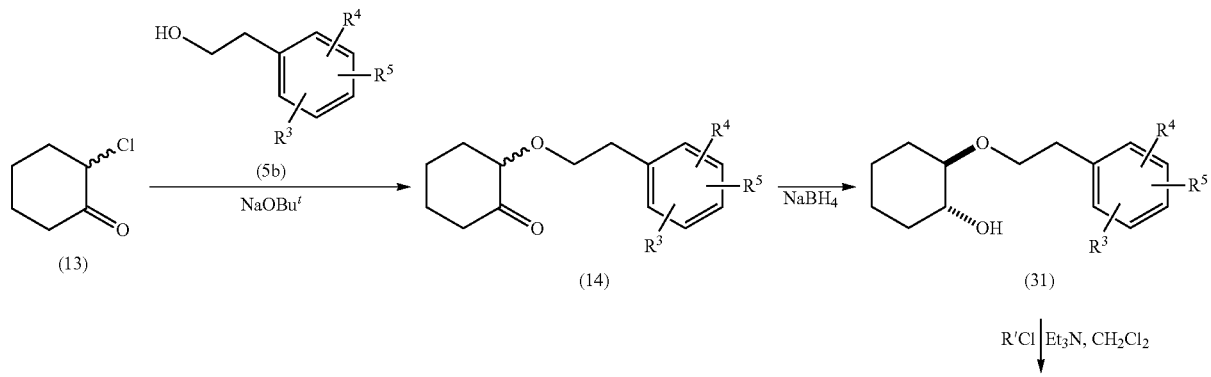

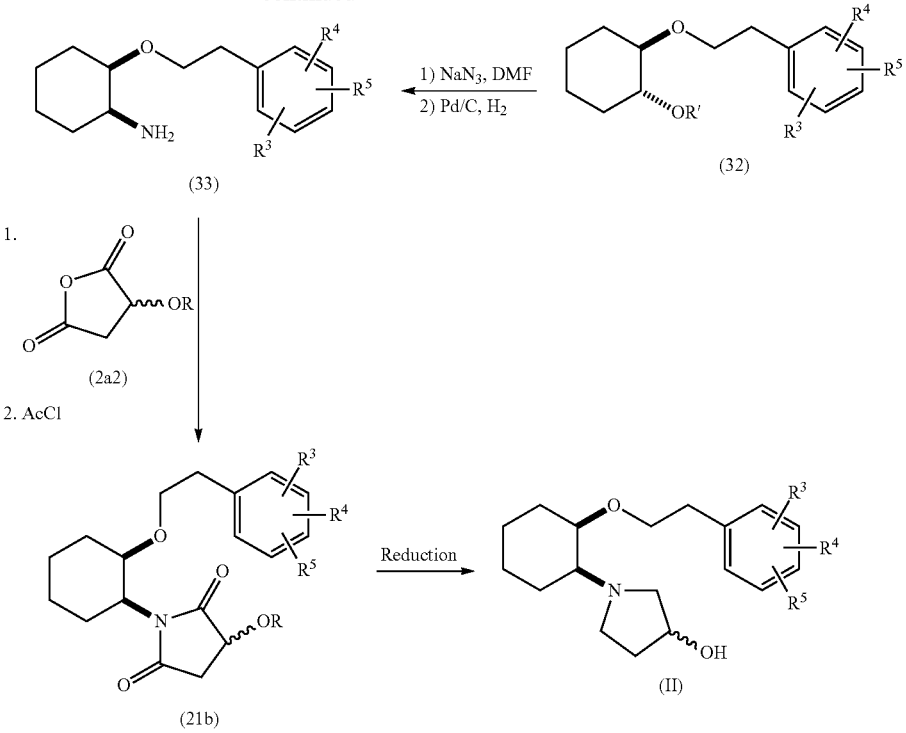

In general, compounds of formula (II) can be prepared by the method disclosed above for Reaction Scheme 2C in a manner similar to that described above for the preparation of compounds of formula (I) as set forth in Reaction Scheme 1C except that, instead of an asymmetric reduction step followed by hydrogenation to produce the corresponding intermediate of formula (15) in Reaction Scheme 1C, the compound of formula (14) in Reaction Scheme 2C above may be treated under standard reduction conditions, such as treatment with a reducing agent, preferably NaBH$_4$, to produce compound of formula (31), which is then converted into the activated compound of formula (32). Compound of formula (32) is then treated in a similar manner as the compound of formula (16) in Reaction Scheme 1C to produce the compound of formula (II).

The following preparations are offered by way of illustration and not by way of limitation. Unless otherwise specified, starting materials and reagents may be obtained from well-known commercial supply houses, e.g., Sigma-Aldrich Fine Chemicals (St. Louis, Mo.), and are of standard grade and purity; or may be obtained by procedures described in the art or adapted therefrom, where suitable procedures may be identified through the Chemical Abstracts and Indices therefor, as developed and published by the American Chemical Society (Washington, D.C.).

Preparation 1

2-(R)-Acetoxy-N-(2R-benzyloxycyclohexyl]succinamic acid (7a) or 3-(R)-acetoxy-N-(2R-benzyloxycyclohexyl)succinamic acid (8a)

To a stirred solution of (1R,2R)-2-benzyloxycyclohexylamine (1) (BASF, WO 96/23894, CAS Registry No. 216394-06-8, 0.80 g, 3.90 mmol) in anhydrous dichloromethane (10 mL) was added 2R-acetoxysuccinic anhydride (2a1) (781 mg, 4.94 mmol) in small portions. The reaction was left to stir at ambient temperature under inert atmosphere until total consumption of the starting material was observed by HPLC. When the reaction was deemed complete, the volatiles were removed under vacuum to give (7a)/(8a) as a white solid (1.45 g, quantitative yield); MS (ES+) 364.2 [M+H]$^+$, 386.2 [M+Na]$^+$, 727.4 [2M+H]$^+$, 749.4 [2M+Na]$^+$; MS (ES−) 362.1 [M]$^−$, 725.3 [2M]$^−$; $^1$H-NMR (400 MHz, CDCl$_3$) δ 1.12-1.41 (m, 4H), 1.58-1.61 (m, 1H), 1.73-1.76 (m, 1H), 2.02 (s, 3H, CH$_3$), 2.08-2.19 (m, 2H), 2.88 (d, 1H, J=5.6 Hz), 3.19-3.28 (m, 1H), 3.72-3.81 (m, 1H), 4.37-4.41 (m, 1H), 4.58-4.63 (m, 1H), 5.34-5.38 (m, 1H), 6.29 (d, 1H, J=7.6 Hz), 7.21-7.34 (m, 5H); $^{13}$C-NMR (100 MHz, CDCl$_3$) δ 20.72, 23.68, 23.93, 29.91, 30.68, 36.24, 52.99, 69.68, 69.82, 69.85, 78.84, 127.59, 127.63, 127.77, 127.80, 128.34, 128.39, 128.51, 138.42, 168.55, 169.60, 173.48.

Preparation 2

(3R)-1-((1R,2R)-2-benzyloxycyclohex-1-yl)-2,5-dioxopyrrolidin-3-yl acetate (3a)

2R- or 3R-Acetoxy-N-(2R-benzyloxycyclohexyl)succinamic acid (7a)/(8a) (1.40 g, 3.85 mmol) was dissolved in acetyl chloride (15 mL). The resultant homogenous solution was refluxed at 60° C. for 45 minutes. Volatiles were removed under vacuum and the resultant residue was further dried under high vacuum to give (3R)-1-((1R,2R)-2-benzyloxycyclohex-1-yl)-2,5-dioxopyrrolidin-3-yl acetate (3a) as a clear, pale yellow syrup; MS (ES+) 346.1 [M+H]$^+$, 363.2 [M+H$_2$O]$^+$, 368.1 [M+Na]$^+$; $^1$H-NMR (400 MHz, CDCl$_3$) δ 1.24-1.32 (m, 3H), 1.66-1.80 (m, 3H), 2.10 (s, 3H), 2.12-2.29 (m, 2H), 2.40-2.45 (m, 1H), 2.88-2.96 (m, 1H), 3.95-4.07 (m, 2H), 4.23-4.27 (m, 1H), 4.57-4.61 (m, 1H), 5.05 (br s, 1H), 7.18-7.20 (m, 2H), 7.23-7.31 (m, 3H); $^{13}$C-NMR (100 MHz, CDCl$_3$) δ 20.58, 23.90, 24.89, 27.87, 31.32, 35.39, 56.12, 66.78, 70.54, 75.64, 127.50, 128.27, 128.99, 138.83, 169.71, 173.33, 173.49.

Preparation 3

(3R)-1-((1R,2R)-2-Hydroxycyclohex-1-yl)-2,5-dioxopyrrolidin-3-yl acetate (4a)

To a solution of acetic acid (1R,2R)-benzyloxycyclohexyl-2,5-dioxo-pyrrolidin-3-(R)-yl ester (3a (1.1 g, 3.18 mmol) in MeOH was added 10% Pd—C (110 mg), and the reaction vessel was flushed twice with H$_2$. The reaction mixture was agitated at ambient temperature under H$_2$ (charged balloon). After 4 hours, the reaction mixture was filtered through a pad of Celite. The filtrate was concentrated in vacuo to give acetic acid 1R,2R-hydroxycyclohexyl-2,5-dioxopyrrolidin-3-(R)-yl ester (4a) as a white hygroscopic foam (0.82 g, 99% yield); MS (ES+) 256.1 [M+H]$^+$, 278.0 [M+Na]$^+$, 533.1 [2M+Na]$^+$; $^1$H-NMR (400 MHz, CDCl$_3$) δ 1.11-1.34 (m, 3H), 1.64-1.75 (m, 3H), 2.02-2.09 (m, 2H), 2.12 (s, 3H, CH$_3$), 2.22 (br s, 1H), 2.63 (dd, 1H, J=18.0 Hz, 4.8 Hz), 3.11 (dd, 1H, J=8.8 Hz, J=18 Hz), 3.82 (ddd, 1H, J=4.16 Hz, J=10.6 Hz, J=12.8 Hz), 4.16 (ddd, 1H, J=4.4 Hz, J=10.4 Hz, J=14.8 Hz), 5.34 (dd, 1H, J=8.8 Hz, J=4.8 Hz); $^{13}$C-NMR (100 MHz, CDCl$_3$) δ 20.52, 24.16, 24.98, 27.77, 35.03, 35.40, 58.44, 67.43, 68.40, 170.11, 173.89, 174.08.

Preparation 4

3,4-(Dimethoxyphenethoxy)trichloracetimidate (5a)

To a reaction flask was charged 3,4-dimethoxyphenethyl alcohol (50 mL), and the resultant mixture was adjusted to 12° C. (9-15° C.). Solid potassium hydroxide (5.0 g, 1.62 equiv), and methyltributylammonium chloride (75 wt % solution in water; 0.4 g, 0.02 equiv) were charged to the reaction flask. Under maximum agitation, trichloroacetonitrile (10.0 g, 1.26 equiv) was charged slowly to the reaction flask via an addition funnel, while the pot temperature was maintained <15° C. The reaction mixture was agitated at 12° C. (9-15° C.) for 1-4 hours. The reaction mixture was diluted with methyl tert-butyl ether (MTBE) (20 mL), then cooled to 3° C. (0-6° C.). Next, the MTBE layer was washed with water (3×20 mL) at 3° C. (0-6° C.). The MTBE solution was concentrated under reduced pressure to dryness at a maximum bath temperature of 40° C., and ethanol (55 mL) was added to the remaining residue and the mixture was agitated at 25° C. (22-28° C.) until a clear solution was achieved. The ethanolic solution was cooled to 0° C. (−3 to 3° C.) to allow product crystallization. The slurry was diluted with water (77 mL) and the mixture was agitated at 0° C. (−3 to 3° C.) for ~1 h. The slurry was filtered and rinsed with cold (0-6° C.) water (36 mL). The wet cake was dried under vacuum at ambient temperature (15-25° C.) until the moisture content (KF) was lower than 0.05% to give 3,4-(dimethoxyphenethoxy)trichloracetimidate (5a), as an off-white crystalline solid (90-95% yield); $^1$H-NMR (300 MHz, CDCl$_3$) δ 2.97 (t, 2H, J=7 Hz, CH$_2$), 3.81 & 3.79 (2 s, 6H, 2×OCH$_3$), 4.42 (t, 2H, J=7 Hz, CH$_2$O), 6.77-6.75 (m, 3H, Ar), 8.22 (br s, 1H, NH).

Preparation 5

Acetic acid 1R,2R-(3,4-dimethoxyphenethoxy)cyclohexyl}-2,5-dioxo-pyrrolidin-3R-yl ester (6a)

A solution of acetic acid 1R,2R-hydroxycyclohexyl-2,5-dioxopyrrolidin-3-(R)-yl ester (4a) (0.75 g, 3.08 mmol) in toluene (8 mL) was cooled to 0° C. Tetrafluoroboric acid diethyl ether complex (0.2 equiv, 87 μL) was charged to the flask and the mixture was agitated at ambient temperature for ~30 min. A solution of 3,4-(dimethoxyphenethoxy)trichloracetinnidate (5a) (1.05 g, 1.05 equiv) in toluene (5 mL) was added via a syringe over 15-20 min. The reaction mixture was agitated at ambient temperature until the reaction was complete. On completion, the reaction mixture was cooled to −10° C. and the precipitated trichloroacetamide was filtered. The cake was rinsed with cold toluene (10 mL), and the toluene filtrate was washed successively with water (15 mL) and brine (15 mL). The organic layer was dried (anhydrous MgSO$_4$), filtered, and concentrated under reduced pressure to give a light brown syrup. The crude product was purified by flash column chromatography (silica gel; EtOAc:hexane, 1:4 v/v) to give acetic acid 1R,2R-(3,4-dinnethoxyphenethoxy)cyclohexyl}-2,5-dioxo-pyrrolidin-3R-yl ester (6a) as a thick colorless syrup (0.92 g, 75% yield); MS (ES+) 420.2 [M+H]$^+$, 437.2 [M+H$_2$O]$^+$, 442.2 [M+Na]$^+$; $^1$H-NMR (400 MHz, CDCl$_3$) δ 1.10-1.33 (m, 3H), 1.61-1.75 (m, 3H), 1.91-2.02 (m, 1H), 2.07 (s, 3H), 2.17-2.20 (m, 1H), 2.34 (dd, 1H, J=5.2 Hz, J=18 Hz), 2.59-2.76 (m, 3H), 3.13 (ddd, 1H, J=5.6 Hz, J=8.8 Hz, J=14.4 Hz), 3.77-3.93 (m, 9H), 4.71 (br s, 1H), 6.46-6.67 (m, 2H), 6.77-6.79 (m, 1H); $^{13}$C-NMR (100 MHz, CDCl$_3$) δ 20.35, 23.85, 24.87, 28.04, 30.88, 35.07, 35.84, 55.66, 55.70, 55.72, 66.72, 68.81, 75.02, 110.95, 111.99, 112.52, 132.21, 147.09, 148.29, 169.54, 173.16, 173.57.

Preparation 6

Preparation of Acetic acid 1R,2R-(3,4-dimethoxyphenethoxy)cyclohexyl}-2,5-dioxo-pyrrolidin-3R-yl ester (6a) via One-pot Process (Acylation, Etherification, and Cyclization)

To a cold (0° C.) solution of 1R,2R-aminocyclohexanol (1a) (1.00 g, 8.68 mmol) in dichloromethane (17.4 mL) under nitrogen was added 2R-acetoxysuccinic anhydride (2a1) (1.44 g, 9.11 mmol). The reaction was allowed to warm to ambient temperature and stirred for 1.5 h. 3,4-(dimethoxyphenethoxy)trichloracetimidate (5a) (3.41 g, 10.4 mmol) was added in a single portion and the solution was subsequently cooled to 0° C. HBF$_4$ (359 μL, 54% in Et$_2$O, 2.60 mmol) was added and the resultant mixture was stirred for 2.5 h. Acetyl chloride (15 mL) was added via syringe, and the solution was raised to reflux for 1 h, and then allowed to cool to ambient temperature prior to removal of solvent in vacuo. The residue was taken up in ethyl acetate (25 mL) and water (25 mL), the organic layers were separated and the aqueous layer extracted with ethyl acetate (2×25 mL). The combined organic layers were washed successively with H$_2$O (25 mL) and brine (25 mL), dried with MgSO$_4$ (anhydrous), filtered, and the solvent was removed in vacuo. Flash column chromatography of the residue on silica gel (35% EtOAc/hexanes) yielded acetic acid 1R,2R-(3,4-dimethoxyphenethoxy)cyclohexyl}-2,5-dioxo-pyrrolidin-3R-yl ester (6a), as a viscous yellow oil (680 mg, 19% yield); MS (ES+) 420.1 [M+H]$^+$, 437.1 [M+H$_2$O]$^+$, 442.0 [M+Na]$^+$.

Preparation 7

Preparation of (3R)-1-[(1R,2R)-2-[2-(3,4-dinnethoxyphenyl)ethoxy]cyclohexyl]-3-pyrrolidinol (Compound of formula (Ia))

To a solution of acetic acid 1R,2R-(3,4-dimethoxyphenethoxy)cyclohexyl}-2,5-dioxo-pyrrolidin-3R-yl ester (6a) (0.5 g, 1.19 mmol) in anhydrous THF (2 mL) was added borane-THF complex solution (1M, 8.0 mL) under $N_2$. The reaction mixture was stirred at ambient temperature for 18 hours. The reaction mixture was cooled to 0° C. and quenched slowly by addition of a solution of MeOH (5.0 mL) saturated with HCl gas and concentrated under vacuum to give a pale yellow syrup. Trituration of the syrup in $Et_2O$ (10 mL) afforded the monohydrochloride salt of (3R)-1-[(1R,2R)-2-[2-(3,4-dinnethoxyphenyl)ethoxy]cyclohexyl]-3-pyrrolidinol (Ia) as an off-white solid (340 mg, 74% yield) with 79.5% HPLC purity; $^1$H NMR (400 MHz, $D_2O$): δ 7.05-7.02 (m, 2H), 6.94 (dd, 1H, J 2 Hz, 8 Hz), 4.43-4.38 (m, 1H), 4.11-4.04 (m, 1H), 3.89 (s, 3H), 3.87 (s, 3H), 3.69 (overlapping dt, 1H, J 6 Hz, 9 Hz), 3.50-3.40 (m, 1H), 3.31-3.01 (m, 5H), 2.97-2.79 (m, 2H), 2.37-2.30 (m, 1H), 2.10-1.70 (m, 5H), 1.45-1.12 (m, 4H).

Isomeric purity: 99.6% ee hydrochloride salt of (3R)-1-[(1R,2R)-2-[2-(3,4-dinnethoxyphenyl)ethoxy]cyclohexyl]-3-pyrrolidinol (Ia) vs hydrochloride salt of (3R)-1-[(1S,2S)-2-[2-(3,4-dinnethoxyphenyl)ethoxy]cyclohexyl]-3-pyrrolidinol (Ib)

Isomeric purity 4.02% of the hydrochloride salt of (3S)-1-[(1R,2R)-2-[2-(3,4-dimethoxyphenyl)ethoxy]cyclohexyl]-3-pyrrolidinol (Ic) observed.

Preparation 8

In a similar manner as set forth above in Preparation 1-Preparation 7, the following compounds of formula (I) are prepared:

(3R)-1-[(1S,2S)-2-[2-(3,4-dimethoxy-phenyl)ethoxy]cyclohexyl]-3-pyrrolidinol, (Compound of formula (Ib)), $^1$H NMR ($D_2O$, 400 MHz) δ 7.06-7.01 (m, 2H), 6.94 (dd, 1H, J=8, J=2), 4.43 (br s, 1H), 4.06 (overlapping dt, 1H, J=9, J=6), 3.87, 3.86 (two s, 2×3H), 3.75-3.67 (m, 1H), 3.52-2.80 (m, 8H), 2.38-2.30 (m, 1H), 2.12-1.70 (m, 5H), 1.47-1.10 (m, 4H);

(3S)-1-[(1R,2R)-2-[2-(3,4-dimethoxy-phenyl)ethoxy]cyclohexyl]-3-pyrrolidinol, (Compound of formula (Ic)), $^1$H NMR ($D_2O$, 400 MHz) δ 6.88-6.82 (m, 2H), 6.78-6.73 (m, 1H), 4.29 (br s, 1H), 3.91-3.83 (m, 1H), 3.71, 3.69 (two s, 2×3H), 3.58-3.47 (m, 1H), 3.40-2.94 (m, 6H), 2.80-2.62 (m, 2H), 2.22-2.10 (m, 1H), 2.03-1.55 (m, 5H), 1.32-0.95 (m, 4H); and (3S)-1-[(1S,2S)-2-[2-(3,4-dimethoxy-phenyl)ethoxy]cyclohexyl]-3-pyrrolidinol, (Compound of formula (Id)), $^1$H NMR ($D_2O$, 400 MHz) δ 7.06-7.01 (m, 2H), 6.95 (dd, 1H, J=8, J=2), 4.40 (br s, 1H), 4.12-4.03 (m, 1H), 3.88, 3.87 (two s, 2×3H), 3.73-3.66 (m, 1H), 3.50-2.80 (m, 8H), 2.37-2.30 (m, 1H), 2.10-1.73 (m, 5H), 1.45-1.10 (m, 4H).

Preparation 9

(1R,2R)-1-{2-[2-(4-Benzyloxy-3-methoxy-phenyl)-ethoxy]-cyclohexyl}-(3R)-2,5-dioxo-pyrrolidin-3-yl acetate A. To a solution of (3R)-1-((1R,2R)-2-hydroxylcyclohex-1-yl)-2,5-dioxopyrrolidin-3-yl acetate (4a) (13.5 g, 53.1 mmol) in anhydrous toluene (80 mL) at 0° C. under a nitrogen atmosphere was added $HBF_4.OEt_2$ (3.40 g, 21.2 mmol, 2.90 mL). The mixture was stirred for 15 minutes and a solution of 2-(4-benzyloxy-3-methoxyphenyl)ethyl-2,2,2-trichloroacetimidate (23.5 g, 58.4 mmol) in anhydrous toluene (100 mL) was added via an addition funnel over a period of 30 minutes. The solution was allowed to warm to ambient temperature and stirred for 3 hours. Water (100 mL) was then added and stirred for 15 minutes. 10% aqueous $NaHCO_3$ (10 mL) was also added slowly and stirred until no more bubbling was observed. The mixture was then transferred to a separatory funnel and the layers were separated. The organic phase was washed successively with 10% aqueous $NaHCO_3$ (3×150 mL), water (150 mL), and brine (100 mL). The organic phase was dried over $Na_2SO_4$, filtered, and concentrated. The residue was dissolved in toluene (200 mL) and cooled to −20° C. for 18 h to precipitate the trichloroacetamide by-product. The mixture was filtered and the filtrate was concentrated.

B. The above procedure was repeated with (3R)-1-((1R,2R)-2-hydroxylcyclohex-1-yl)-2,5-dioxopyrrolidin-3-yl acetate (30.5 g, 0.120 mol). The crude product from the two reactions were combined and purified by column chromatography (hexanes-EtOAc, 4:1, v/v). The product from the chromatography was dissolved in toluene (200 mL) and cooled to −20° C. for 48 hours to precipitate out the remaining trichloroacetamide by-product. The mixture was filtered and the filtrate was concentrated to afford (1R,2R)-1-{2-[2-(4-benzyloxy-3-methoxyphenyl)ethoxy]cyclohexyl}-(3R)-2,5-dioxopyrrolidin-3-yl acetate (49.5 g, 58% combined yield) as a light yellow oil; MS (ESI): 496.1 [M+H]$^+$, 518.1 [M+Na]$^+$.

Preparation 10

(1R,2R)-1-{2-[2-(4-Benzyloxy-3-methoxyphenyl)ethoxy]cyclohexyl}-(3R)-pyrrolidin-3-ol hydrochloride To a solution of (1R,2R)-1-{2-[2-(4-benzyloxy-3-methoxyphenyl)ethoxy]-cyclohexyl}-(3R)-2,5-dioxopyrrolidin-3-yl acetate (49.0 g, 100 mmol) in anhydrous THF (100 mL) under nitrogen was added slowly $BH_3$.THF (1.0 M solution in THF, 400 mmol, 400 mL). The solution was heated to 80° C. and stirred for 3 hours. The solution was cooled to ambient temperature and methanol (100 mL) was added slowly until no more bubbling was observed. The solution was concentrated and methanolic HCl (1.25 M solution in $CH_3OH$, 500 mL) was added. The solution was heated to 80° C. and stirred for 1 hour. The cooled solution was then concentrated to afford (1R,2R)-1-{2-[2-(4-benzyloxy-3-methoxyphenyl)ethoxy]cyclohexyl}-(3R)-pyrrolidin-3-ol hydrochloride (50.8 g, quantitative yield) as a yellow syrup. The crude product was used in the next step without further purification; $^1$H NMR (400 MHz, $CDCl_3$) δ 11.45 (br, s, 1H), 7.50-7.10 (m, 5H), 6.90-6.60 (m, 3H), 4.22 (br, s, 1H), 4.00-3.85 (m, 5H), 3.75-3.55 (m, 2H), 3.35-2.50 (m, 7H), 2.45-2.20 (m, 2H), 2.08 (br, s, 1H), 1.90-1.50 (m, 3H), 1.35-1.05 (m, 6H); MS (ESI): 426.2 [M+H]$^+$ Preparation 11

(3R)-1-[(1R,2R)-2-[2-(4-Hydroxy-3-methoxy-phenyl)ethoxy]cyclohexyl]-3-pyrrolidinol (Compound of formula (Ie))

A solution of compound (1R,2R)-1-{2-[2-(4-benzyloxy-3-methoxyphenyl)ethoxy]cyclohexyl}-(3R)-pyrrolidin-3-ol (50.3 g, 100 mmol) in methanol (250 mL) was transferred to a Parr shaker bottle that has previously been charged with Pd/C (10% wt/wt, 4.0 g) as a slurry in water. The bottle was placed on a Parr hydrogenator and evacuated. Hydrogen pressure (60 psi) was then applied and the vessel was shaken for 1 hour. The mixture was filtered through a pad of Celite and the filtrate was concentrated. The residue was dissolved in water (250 mL) and washed successively with ethyl acetate (3×200 mL) and chloroform (10×150 mL). The aqueous solution was saturated with NaCl and washed with dichloromethane (4×200 mL). The combined organic extract was concentrated and 5% aqueous NaHCO$_3$ (200 mL) was added to the residue. The suspension was stirred for 30 minutes and then extracted with ethyl acetate (8×250 mL). The combined organic extracts were dried over anhydrous Na$_2$SO$_4$, filtered, and concentrated to afford a yellowish powder. The powder was then triturated with ethyl acetate (3×50 mL) and subjected to high vacuum (oil pump) to afford (3R)-1-[(1R,2R)-2-[2-(4-hydroxy-3-methoxy-phenyl)ethoxy]cyclohexyl]-3-pyrrolidinol (15.6 g, 43% yield) as a white powder; $^1$H NMR (400 MHz, CDCl$_3$) δ 6.82 (d, 1H, J=8.0), 6.75 (br s, 1H), 6.70 (d, 1H, J=8.0), 4.30-4.20 (m, 1H), 3.87 (s, 3H), 3.78-3.70 (m, 1H), 3.56 (q, 1H), 3.33 (td, 1H, J=7.6, J=3.6), 2.97-2.89 (m, 1H), 2.84-2.75 (m, 3H), 2.65 (dd, 1H, J=10, J=5.2), 2.55-2.38 (m, 2H), 2.09-1.95 (m, 2H), 1.91-1.82 (m, 1H), 1.73-1.58 (m, 3H), 1.41-1.15 (m, 4H); $^{13}$C-NMR (100 MHz, CDCl$_3$) δ 23.25, 23.68, 27.59, 29.21, 34.42, 36.70, 48.84, 56.06, 59.93, 63.68, 69.83, 71.29, 79.59, 111.98, 114.60, 121.65, 131.35, 144.23, 146.67; IR: 3436 (O—H stretch), 1591, 1515, 1272, 1098, 1030, 851 cm$^{-1}$; MS (ESI) 336.2 (M+1)$^+$.

Preparation 12

(1R,2R)-1-{2-[2-(3-Benzyloxy-4-methoxy-phenyl)ethoxy]cyclohexyl}-2,5-dioxo-pyrrolidin-3-(R)-yl acetate To a chilled (0° C.) solution of (3R)-1-((1R,2R)-2-hydroxylcyclohex-1-yl)-2,5-dioxopyrrolidin-3-yl acetate (15.0 g, 58.7 mmol) in anhydrous dichloromethane (100 mL) was added tetrafluoroboric acid diethyl ether complex (3.2 mL). The resultant reaction mixture was stirred at 0° C. for 20 minutes before adding a solution of 2-(3-benzyloxy-4-methoxy-phenyl)ethyl-2,2,2-trichloroacetimidate (24.8 g, 61.6 mmol, 1.05 equiv.) in dichloromethane (100 mL) via an addition funnel over 30 minutes. The reaction mixture was stirred at 0° C. until the reaction was judged complete by HPLC analysis. The reaction mixture was quenched with water (250 mL). The organic layer was separated from the aqueous layer and subsequently washed with dilute NaHCO$_3$ (5% wt solution, 2×100 mL), and water (5×100 mL). The organic layer was dried (anhydrous MgSO$_4$), filtered, and concentrated under reduced pressure to ~100 mL solution. The solution was cooled at –20° C. for 24 hours and the precipitate (trichloroacetamide) was removed by filtration. The filtrate was further concentrated to a volume of ~40 mL. This process was repeated three times until the bulk of the by-product (trichloroacetamide) was removed. After the third filtration, the filtrate was concentrated in vacuo to give (1R,2R)-1-{2-[2-(3-benzyloxy-4-methoxy-phenyl)ethoxy]cyclohexyl}-2,5-dioxopyrrolidin-3-(R)-yl acetate as a pale yellow syrup (25 g, 86% yield).

Preparation 13

(3R)-1-[(1R,2R)-2-[2-(3-benzyloxy-4-methoxyphenyl)ethoxy]cyclohexyl]-3-pyrrolidinol hydrochloride To a solution of (1R,2R)-1-{2-[2-(3-Benzyloxy-4-methoxy-phenyl)ethoxy]cyclohexyl}-2,5-dioxopyrrolidin-3-(R)-yl acetate (42.0 g, 84.8 mmol) in anhydrous THF (300 mL) at 0° C. was added borane-THF complex solution (1.0 M, 297 mL, 3.5 mol equivalents) under N$_2$ via an addition funnel over a period of 60 minutes. The reaction mixture was heated to reflux for 60 minutes. The reaction mixture was cooled to 0° C. and quenched slowly by addition of methanol (~15 mL). The reaction mixture was concentrated under reduced pressure to remove the THF and to the residue was added methanolic-HCl solution (~1.25 M in methanol, 297 mL, 3.5 equivalents). The solution was then heated at 70-80° C. for 2 hours. The reaction mixture was cooled to ambient temperature and concentrated under reduced pressure to give (3R)-1-[(1R,2R)-2-[2-(3-benzyloxy-4-methoxy-phenyl)ethoxy]cyclohexyl]-3-pyrrolidinol hydrochloride as a colorless syrup (35.0 g, 89% yield). The sample was used directly without further purification in the next step.

Preparation 14

(3R)-1-[(1R,2R)-2-[2-(3-Hydroxy-4-methoxy-phenyl)ethoxy]cyclohexyl]-3-pyrrolidinol (Compound of formula (If))

To compound (3R)-1-[(1R,2R)-2-[2-(3-benzyloxy-4-methoxy-phenyl)ethoxy]cyclohexyl]-3-pyrrolidinol (35.0 g, 75.8 mmol) was added methanol (150 mL). This solution was transferred to a Parr bottle and Pd/C (10% wt/wt on activated carbon) was added portion-wise while maintaining a N$_2$ atmosphere through the reaction mixture. Hydrogen pressure (60 psi) was then applied and the vessel shaken for 3 hours, after which HPLC showed complete consumption of the starting material. The reaction mixture was filtered through a pad of Celite and the filtrate was concentrated to give (3R)-1-[(1R,2R)-2-[2-(3-hydroxy-4-methoxy-phenyl)ethoxy]cyclohexyl]-3-pyrrolidinol as a colorless syrup. The crude product was dissolved in 1 M aqueous HCl solution (450 mL) and washed with chloroform (8×250 mL). The aqueous layer was then saturated with solid NaCl (100 g) and the solution was extracted with dichloromethane (8×200 mL). The combined dichloromethane extracts were dried (anhydrous MgSO$_4$), filtered, and concentrated under reduced pressure to give 3R)-1-[(1R,2R)-2-[2-(3-hydroxy-4-methoxy-phenyl)ethoxy]cyclohexyl]-3-pyrrolidinol as a colorless syrup; $^1$H NMR (400 MHz, D$_2$O) δ 7.01 (d, H, J=8.0), 6.86-6.83 (m, 2H), 4.42-4.36 (m, 1H), 4.02 (overlapping dt, 1H, J=5.2, J=10.1), 3.85 (s, 3H), 3.67-3.55 (m, 1H), 3.46-2.81 (m, 7H), 2.77-2.70 (m, 1H), 2.34-2.27 (m, 1H), 2.11-1.74 (m, 5H), 1.41-1.10 (m, 4H); IR: 3439 (O—H stretch), 1592, 1510, 1098, 1022 cm$^{-1}$; MS (ESI) 336.1 (M+1)$^+$.

Preparation 15

In a similar manner as set forth above in Preparation 9-Preparation 14, but using the appropriately substituted starting materials, the following compounds of formula (I) were prepared:
(3R)-1-[(1R,2R)-2-[2-(4-ethoxy-3-methoxy-phenyl)ethoxy]cyclohexyl]-3-pyrrolidinol, (Compound of formula (Ig)); and
(3R)-1-[(1R,2R)-2-[2-(3-ethoxy-4-methoxy-phenyl)ethoxy]cyclohexyl]-3-pyrrolidinol (Compound of formula (Ih)).

Preparation 16

(3R)-1-[(1R,2R)-2-[2-(3,4-dimethoxyphenyl)ethoxy]cyclohexyl]-3-pyrrolidinol (Preparation of compound of formula (Ia) without solvent exchange)

A. To a stirred solution of (1R,2R)-2-benzyloxycyclohexylamine (1) (125 g, 0.609 mol) in toluene (1620 g) was added 2R-acetoxysuccinic anhydride (2a1) (129 g, 0.816 mol, 1.34 equiv.) in small portions as a solid. The reaction mixture was stirred at 65° C. under inert atmosphere. After 4 hours stirring, no starting material was observed by HPLC. The reaction mixture was cooled to 48-50° C. and acetyl chloride (107 g, 1.37 mol, 2.24 equiv.) was added. The mixture was heated to 60° C. giving a clear solution and was stirred at the latter temperature for further 3 hours. The reaction mixture was cooled to ambient temperature. After allowing to stand at ambient temperature for 16 hours, the excess of acetyl chloride was distilled off at ambient pressure. The distillation was stopped until the boiling point reached a temperature of ca. 105° C. From the reaction mixture was distilled 172 g (acetyl chloride and toluene) off to receive 1714 g of (3R)-1-((1R,2R)-2-benzyloxycyclohex-1-yl)-2,5-dioxopyrrolidin-3-yl acetate (3a) in toluene.

B. To a solution of (3R)-1-((1R,2R)-2-benzyloxycyclohex-1-yl)-2,5-dioxopyrrolidin-3-yl acetate (3a) in toluene (446 g, 0.151 mol) was added 10% Pd/C (6.3 g, 50 wt-% water wet), and the reaction vessel was flushed twice with $H_2$. The reaction mixture was agitated at 18° C. under $H_2$ (5 bar) for 8 hours and at 45° C. under $H_2$ (5 bar) for 15.5 hours. The progress of the reaction was monitored by HPLC. The reaction mixture was filtered, the filtrate was washed with toluene and the filtrate was concentrated in vacuo to give 3-(R)-1-[(1R,2R)-2-hydroxycyclohexyl]-2,5-dioxopyrrolidin-3-yl acetate (4a) as a white hygroscopic foam (46.0 g).

C. To a cooled (0° C.) solution of 3-(R)-1-[(1R,2R)-2-hydroxycyclohexyl]-2,5-dioxopyrrolidin-3-yl acetate (4a) (120.6 g) in 800 g toluene was added 12.5 g tetrafluoroboric acid diethyl ether. After addition the solution was allowed to warm up to 20° C. Then 171 g of 3,4-(dimethoxyphenethoxy) trichloracetimidate (5a) (0.54 mol) in toluene (600 g) was added over a period of 1 hour. The reaction mixture was allowed to stir for further 30 min until the reaction was judged to be complete by HPLC. On completion, the reaction mixture was cooled to −15° C. and the precipitated trichloroacetamide was filtered. The filtrate was washed with water (5×100 g). From the organic layer a part of the solvent was distilled off to receive a dry organic product solution of 3-(R)-1-{(1R,2R)-2-[2-(3,4-dimethoxyphenyl)ethoxy]cyclohexyl}-2,5-dioxo-pyrrolidin-3-yl acetate (6a). To the solution was added 10 g toluene to receive 471.5 g solution, which contains 29.9% of 3-(R)-1-{(1R,2R)-2-[2-(3,4-dinnethoxyphenyl)ethoxy]cyclohexyl}-2,5-dioxo-pyrrolidin-3-yl acetate (6a) (141 g).

D. To the cooled (0° C.) solution of 3-(R)-1-{(1R,2R)-2-[2-(3,4-dimethoxyphenyl)ethoxy]cyclohexyl}-2,5-dioxo-pyrrolidin-3-yl acetate (6a) (29.9% in toluene) was slowly added a solution of borane-THF complex (1 M, 3.5 mol eq., 1016 g) under $N_2$ over a period of 3.5 hours. The reaction mixture was heated at reflux for 1 h. The reaction mixture was cooled to 0° C. and slowly quenched by the addition of a methanolic-HCl solution (~2.5 M in methanol, 373 g). The solution was then heated at reflux for 2 hours (62-66° C.) and the hydrolysis of the borane complex was monitored by HPLC. The reaction mixture was cooled to ambient temperature and concentrated under reduced pressure to obtain (3R)-1-[(1R,2R)-2-[2-(3,4-dinnethoxyphenyl)ethoxy]cyclohexyl]-3-pyrrolidinol (Ia) as a pale yellow syrup. The crude product was dissolved in water (1192 g) and the organic layer was washed with a mixture of methylene chloride/chlorobenzene (1:1; v/v) 4 times. The aqueous layer was then saturated with solid NaCl (316 g) and the solution was extracted with dichloromethane (2×930 g). The combined organic layers were dried (anhydrous $MgSO_4$, 223 g, 8 h), filtered, and concentrated under reduced pressure to give (3R)-1-[(1R,2R)-2-[2-(3,4-dinnethoxyphenyl)ethoxy]cyclohexyl]-3-pyrrolidinol (Ia) as an off-white syrup, which solidified to a white foam upon drying under vacuum. The product was dissolved in isopropyl alcohol (279 g) at reflux, and then a part was distilled off (184.5 g) to receive 170.5 g product solution. To ⅔ of this solution (=114 g) isopropyl acetate (250 g) was added, then the solution was allowed to cool to 5° C. for 4 hours to form a crystalline solid which was filtered and dried under vacuum at ambient temperature for 48 hours to obtain 6.5 g of (3R)-1-[(1R,2R)-2-[2-(3,4-dimethoxyphenyl)ethoxy]cyclohexyl]-3-pyrrolidinol (Ia).

While the invention has been described and illustrated with reference to certain particular embodiments thereof, those skilled in the art will appreciate that various adaptatios, changes, modifications, substitutions, deletions or additions of procedures and protocols may be made without departing from the spirit and scope of the invention. It is intended, therefore, that the invention be defined by the scope of the claims which follow and that such claims be interpreted as broadly as is reasonable to one skilled in the art.

What is claimed is:

1. A method of making a compound of formula (I):

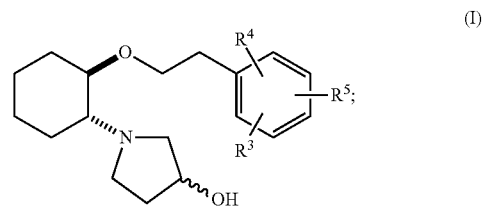

or a pharmaceutically acceptable salt thereof, as a single stereoisomer or as a mixture thereof;

wherein:

$R^3$, $R^4$ and $R^5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$; and $R^6$, $R^7$, $R^8$, and $R^9$ are each independently selected from hydrogen, acetyl, methanesulfonyl or $C_1$-$C_6$alkyl;

which method comprises:

a) a nucleophilic displacement step comprising treating a compound of formula (16):

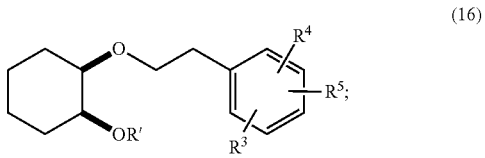

wherein —OR' is an activated leaving group and $R^3$, $R^4$ and $R^5$ are as defined above, with an azide under suitable nucleophilic displacement conditions and subsequent reduction conditions to form a compound of formula (17):

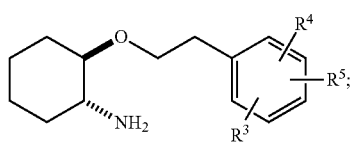

wherein $R^3$, $R^4$ and $R^5$ are as defined above;

b) reacting the compound of formula (17):

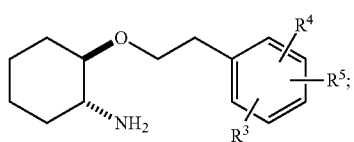

wherein $R^3$, $R^4$ and $R^5$ are as defined above, with a compound of formula (2a2):

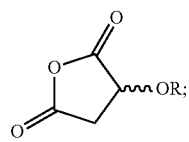

wherein R is H, $C_2$-$C_5$acyl or an oxygen-protecting group, under suitable condensation conditions to form a compound of formula (6b):

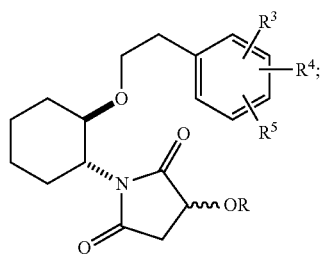

wherein R is H, $C_2$-$C_5$acyl or an oxygen-protecting group and $R^3$, $R^4$ and $R^5$ are as defined above; and c) reducing the compound of formula (6b) under suitable conditions to form a compound of formula (I), as set forth above; and d) optionally forming the pharmaceutically acceptable salt of the compound of formula (I) under suitable conditions.

2. The method of claim 1 further comprising a preparation step to form the compound of formula (16), wherein the preparation step comprises reacting a compound of formula (15):

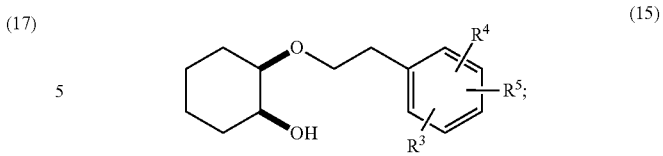

wherein $R^3$, $R^4$ and $R^5$ are as described above, with an activating agent under suitable conditions to form the compound of formula (16) as set forth above.

3. The method of claim 2 wherein the activating agent is an optionally substituted alkylsulfonyl halide or an optionally substituted arylsulfonyl halide.

4. The method of claim 2 further comprising an asymmetric reduction step to form a compound (15), wherein the asymmetric reduction step comprises treating a compound of formula (14):

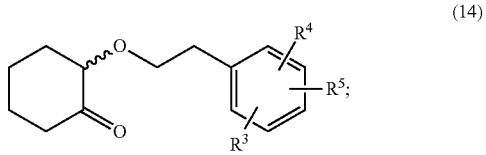

wherein $R^3$, $R^4$ and $R^5$ are as defined above, under asymmetric reduction/hydrogenation conditions to form the compound of formula (15) as set forth above.

5. The method of claim 4 further comprising an etherification step to form a compound of formula (14), wherein the etherification step comprises treating a compound of formula (13):

with a compound of formula (5b):

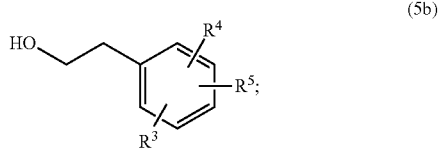

wherein $R^3$, $R^4$ and $R^5$ are as defined above, under suitable conditions to form the compound of formula (14), as set forth above.

6. The method of claim 1 wherein the pharmaceutically acceptable salt is an acid addition salt.

7. The method of claim 1 wherein the compound of formula (I) is a compound of formula (I) where $R^3$, $R^4$ and $R^5$ are independently hydrogen, hydroxy or $C_1$-$C_8$alkoxy; with the proviso that $R^3$, $R^4$ and $R^5$ cannot all be hydrogen at the same time.

8. The method of claim 7 wherein the compound of formula (I) is a compound of formula (Ia):

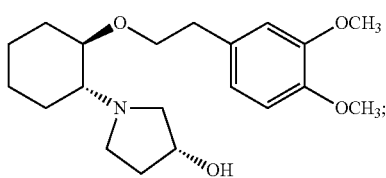
(Ia)
or a pharmaceutically acceptable salt thereof.
9. The method of claim 7 wherein the compound of formula (I) is selected from the group consisting of:
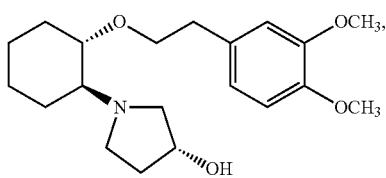
(Ib)
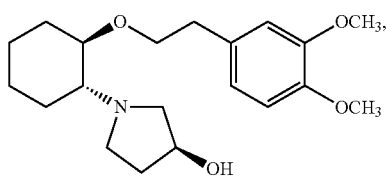
(Ic)
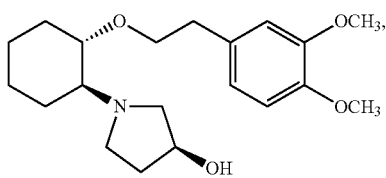
(Id)
-continued
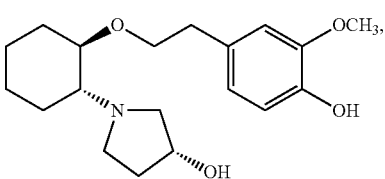
(Ie)
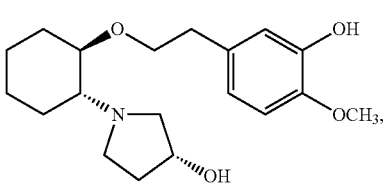
(If)
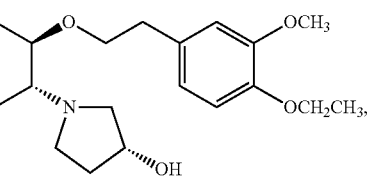
(Ig)
and
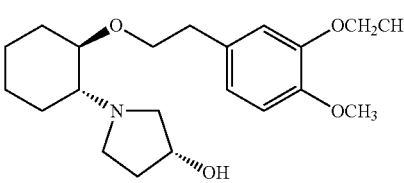
(Ih)
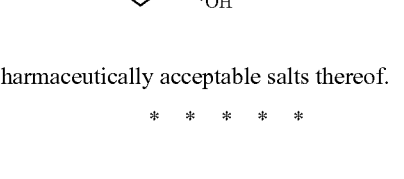
or pharmaceutically acceptable salts thereof.
* * * * *